(12) United States Patent
Zhang et al.

(10) Patent No.: US 8,946,254 B2
(45) Date of Patent: Feb. 3, 2015

(54) BIVALENT LIGANDS FOR THE TREATMENT OF NEUROLOGICAL DISORDERS

(71) Applicant: Virginia Commonwealth University, Richmond, VA (US)

(72) Inventors: Yan Zhang, Glen Allen, VA (US); Kurt F. Hauser, Midlothian, VA (US); Dana E. Selley, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/371,075

(22) PCT Filed: Jan. 10, 2013

(86) PCT No.: PCT/US2013/020966
§ 371 (c)(1),
(2) Date: Jul. 8, 2014

(87) PCT Pub. No.: WO2013/106528
PCT Pub. Date: Jul. 18, 2013

(65) Prior Publication Data
US 2014/0357656 A1   Dec. 4, 2014

Related U.S. Application Data

(60) Provisional application No. 61/584,906, filed on Jan. 10, 2012.

(51) Int. Cl.
*A61K 31/485* (2006.01)
*C07D 489/08* (2006.01)

(52) U.S. Cl.
CPC ............ *C07D 489/08* (2013.01); *A61K 31/485* (2013.01)

USPC .............................................. 514/282; 546/44

(58) Field of Classification Search
USPC .............................................. 514/282; 546/44
See application file for complete search history.

(56) References Cited

PUBLICATIONS

Yuan, Y. et al.: Design and synthesis of a bivalent ligand to explore the putative heterodimerization of the mu opioid recptor and the chemokine receptor CCR5. Organic & Biomol. Chem., vol. 10, pp. 2633-2646, 2012.*
Zhang et al.; "A bivalent ligand (KMN-21) antagonist for μ/κ heterodimeric opioid receptors"; Bioorganic & Medical Chemistry Letters, vol. 19, 2009, pp. 6978-6980.
Chen et al.; Heterodimerization and cross-desensitization between the μ-opioid receptor and the chemokine CCR5 receptor'; European Journal of Pharmacology, vol. 483, 2004, pp. 175-186.
Suzuki et al.; "Interactions of Opioid and Chemkine Receptors: Oligomerization of mu, kappa, and delta with CCR5 on Immune Cells"; Experimental Cell Researcy, vol. 280, 2002, pp. 192-200.
Rook et al.; "Bivalent β-Carbolines as Potential Multitarget Anti-Alzheimer Agents"; Journal of Medicinal Chemistry, vol. 53, 2010, pp. 3611-3617.

* cited by examiner

*Primary Examiner* — Charanjit Aulakh
(74) *Attorney, Agent, or Firm* — Whitham Curtis Christofferson & Cook, PC

(57) ABSTRACT

Bivalent ligands that contain two pharmacophores linked through a spacer, one of which interacts with the μ-opioid receptor (MOR) and the other of which interacts with the co-receptor CC chemokine receptor 5 (CCR5), are used for the treatment of neurological disorders such as those associated with AIDS.

10 Claims, 13 Drawing Sheets

BIVALENT LIGANDS FOR THE TREATMENT OF NEUROLOGICAL DISORDERS

BACKGROUND OF THE INVENTION

1. Field of the Invention

The invention generally relates to bivalent ligands used for the treatment of neurological disorders such as those associated with AIDS. In particular, the invention provides bivalent ligands that contains two pharmacophores linked through a spacer, one of which interacts with the g-opioid receptor (MOR) and the other of which interacts with the co-receptor CC chemokine receptor 5 (CCR5).

2. Background of the Invention

Since acquired immunodeficiency syndrome (AIDS) was identified three decades ago [69], the global prevalence of AIDS has stabilized at 0.8%, with over 33 million people infected with human immunodeficiency virus type-1 (HIV-1) as of 2007. Despite efforts to control the spread of this disease, the population of infected individuals continues to rise. After initial infection with HIV-1, neurovirulent strains targeting the co-receptor CC chemokine receptor 5 (CCR5) enter the central nervous system (CNS) within the first two weeks of infection and can occupy microglia, and to a lesser extent astroglia, to promote viral replication. Not only do these cells enhance pathogenesis by increasing the production of new virus, but their interactions with virus or shed viral proteins such as Tat and gp120 lead to activation and release of pro-inflammatory molecules such as oxyradicals and pro-inflammatory cytokines/chemokines, which, through bystander effects, cause neuronal damage and even death. Of the causes of HIV-1 infection, 10% of cases have been attributed to the contaminated needles of injection drug users (IDUs), and along with changes in risk behavior, the drug abusing population accounts for approximately ⅓ of HIV-1 infected individuals. Additionally, those with HIV-1 infection are more susceptible to abusing drugs. Co-morbid drug use of agents such as heroin, cocaine, and alcohol both accelerate progression to AIDS and complicate its treatment. Heroin abuse, in particular, has been shown to lead to a 4-fold increase in HIV-1 encephalitis (HIVE). Opioid drugs of abuse can synergistically increase both the inflammatory state of the CNS and neuronal damage/death through direct actions on μ-opioid receptor (MOR)-containing glia including astroglia, microglia, oligodendroglia, and glial precursors, and these coordinated responses create a cycle of inflammation whereby neuronal injury/death can occur. Opioids can also exert some direct effects on MOR-expressing neurons. Not only does opioid abuse influence inflammatory signaling, it also affects viral replication. MOR agonists including morphine, methadone, and DAMGO all increase the expression of CCR5, promoting replication of CCR5-utilizing strains, while these increases can be prevented with blockade of MOR by the inhibitors β-funaltrexamine, methylnaltrexone, and naltrexone.

SUMMARY OF THE INVENTION

The synergistic interactions of CCR5 and MOR, are thought to be mediated by direct physical interactions of these two receptors through protein-protein dimerization/oligomerization and result in altered downstream signaling as well as heterologous desensitization Therefore the presence of an opioid agonist through drug abuse or maintenance therapy could alter the effectiveness of antiretroviral medications targeting CCR5, such as the entry inhibitor maraviroc (MVC) which is used in combined antiretroviral therapy. Therefore, it may not be enough to target only CCR5 in the putative CCR5-MOR dimer/oligomer in drug abusing populations, but to interfere with the complex at multiple sites by inhibiting MOR as well. Furthermore, the use of drug abuse medications (e.g., methadone, buprenorphine/naloxone, and naltrexone) to prevent HIV infection in combination with antiretroviral medications (e.g., efavirenz, atazanavir, and maraviroc) immediately raises concerns of drug-drug interactions. It is therefore of great importance to develop new therapeutic strategies to target opioid abuse and HIV-1 comorbidities.

Provided herein are bivalent ligands useful for the treatment of neurological disorders caused or exacerbated by the interaction of the receptors MOR and CCR5. The bivalent ligands contain two pharmacophores that are linked through a spacer. One of the pharmacophores interacts with MOR and the other interacts with CCR5. The interaction of the pharmacophores with the receptors blocks direct physical interactions between the two receptors. As a result, deleterious conditions caused by or associated with MOR/CCR5 interactions are attenuated or eliminated. In one embodiment, the neurological disorders that are treated are those which are associated with AIDS. In other embodiments, the neurological disorders that are treated are those which are associated with opioid-using and/or opioid-addicted individuals, particularly those who are afflicted with AIDS. Advantageously, use of the bivalent ligands as therapeutics avoids drug-drug interactions stemming from using two separate pharmacophores.

It is an object of this invention to provide a bivalent ligand of Formula I,

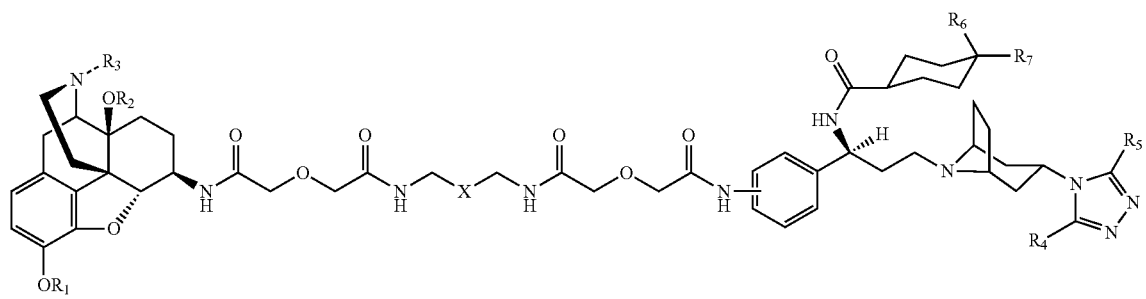

Formula I wherein $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;

$R_3$ may be present or absent and may be H; O; $C_{1-12}$alkyl; —$COOR_9$ where $R_9$ is $C_{1-12}$alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;

R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group; and X=a branched or unbranched, saturated or unsaturated carbon chain comprising from 1-20 carbon atoms, and may include a heteroatomic group;

as well as salts, hydrates, protonated and unprotonated and stereoisomeric forms thereof. In some embodiments, the bivalent ligand is

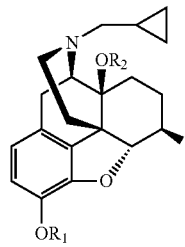
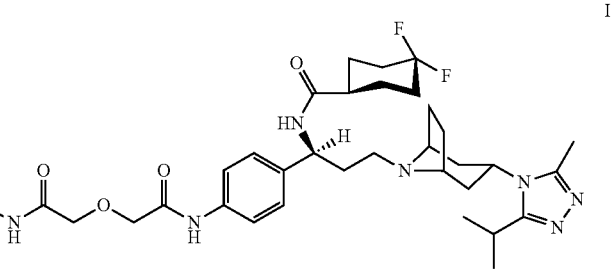

I

The invention also provides pharmaceutical composition comprising at least one bivalent ligand of Formula I

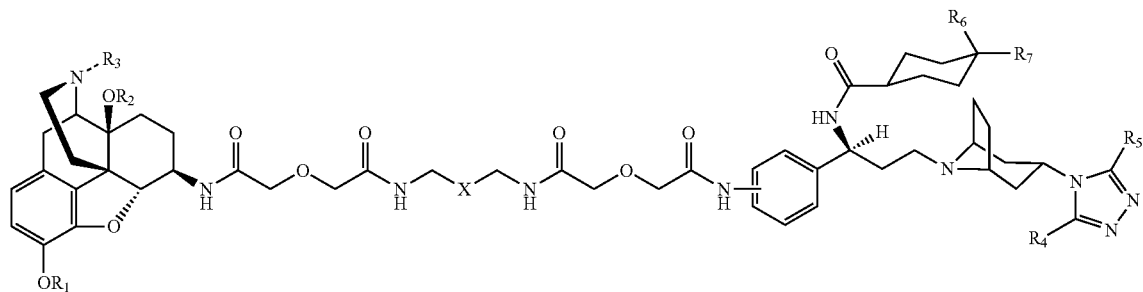

Formula I wherein $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;

$R_3$ may be present or absent and may be H; $H_2$; O; $C_{1-12}$alkyl; —$COOR_9$ where $R_9$ is $C_{1-12}$alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;

R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group;

X=a branched or unbranched, saturated or unsaturated carbon chain comprising from 1-20 carbon atoms, and may include a heteroatomic group;

as well as salts, hydrates, protonated and unprotonated and stereoisomeric forms thereof; and a physiologically compatible carrier. In one embodiment of the pharmaceutical composition, the at least one bivalent ligand is chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;

$R_3$ may be present or absent and may be H; $H_2$; O; $C_{1-12}$alkyl; —$COOR_9$ where $R_9$ is $C_{1-12}$alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;

R6 and R7 may be the same or different, and are independently selected from: H; halogen; a saturated or unsaturated, branched or unbranched, substituted or unsubstituted carbon

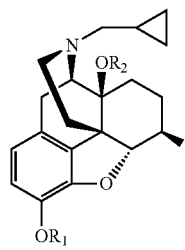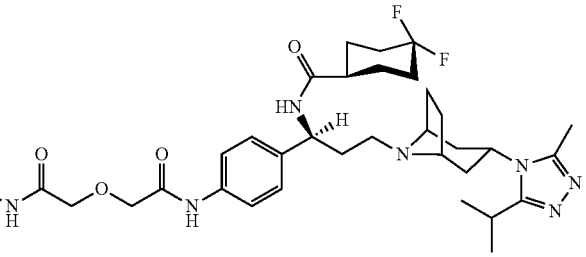

I

The invention also provides methods of treating or preventing a neurological disorder in a subject in need thereof. The methods comprise a step of administering to the subject a therapeutically effective amount of at least one bivalent ligand of Formula I, group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group; and Formula I

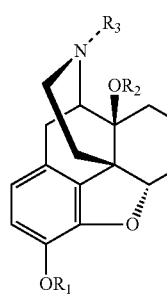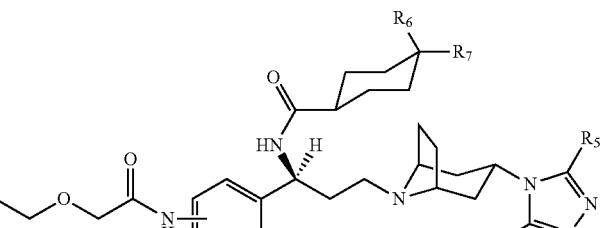

wherein $R_1$ and $R_2$ may be the same or different, and are independently selected from: H; a saturated or unsaturated, branched or unbranched, substituted or unsubstituted carbon group or X=a branched or unbranched, saturated or unsaturated carbon chain comprising from 1-20 carbon atoms, and may include a heteroatomic group; as well as salts, hydrates, protonated and unprotonated and stereoisomeric forms thereof. In one embodiment, the at least one bivalent ligand is

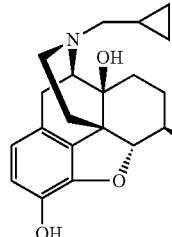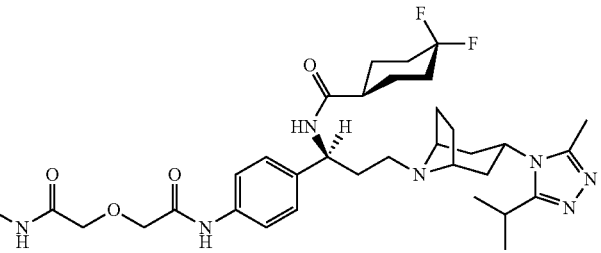

In some embodiments of the method of treatment, the neurological disorder is associated with an interaction between μ-opioid receptor (MOR) and CC chemokine receptor 5 (CCR5). In other embodiments, the neurological disorder is, for example, neurodegeneration, Alzheimer's disease; Parkinson's disease; and/or dementia. In yet other embodiments, the neurodegeneration is caused by bacterial infection, viral infection, and/or opioid use or addiction. In some embodiments, the immune system of the subject who is treated is compromised. In other embodiments, the subject is infected with human immunodeficiency virus (HIV). In yet other embodiments, the subject abuses or is addicted to opiates.

The invention also provides methods of preventing or treating neuroAIDS in a subject in need thereof. The method comprises a step of administering to the subject a therapeutically effective amount of at least one bivalent ligand of Formula I, $R_{11}$) is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;

R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic Formula I

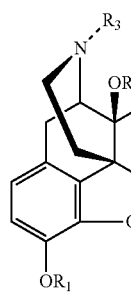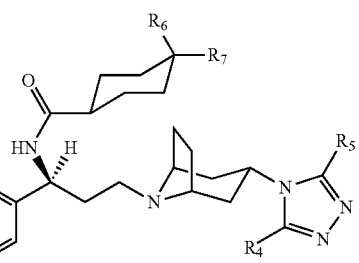

wherein $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;

$R_3$ may be present or absent and may be H; $H_2$; O; $C_{1-12}$alkyl; —$COOR_9$ where $R_9$ is $C_{1-12}$alkyl; $CR_{10}$ where ring system comprising 1, 2, 3, 4, or more rings with from 3 to 7 atoms per ring in the system, which may be fused to one or more atoms of the hexane ring; and a heteroatomic group; and X=a branched or unbranched, saturated or unsaturated carbon chain comprising from 1-20 carbon atoms, and may include a heteroatomic group; as well as salts, hydrates, protonated and unprotonated and stereoisomeric forms thereof. In some embodiments of treating neuroAIDS, the at least one bivalent ligand is

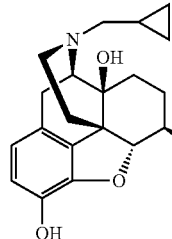
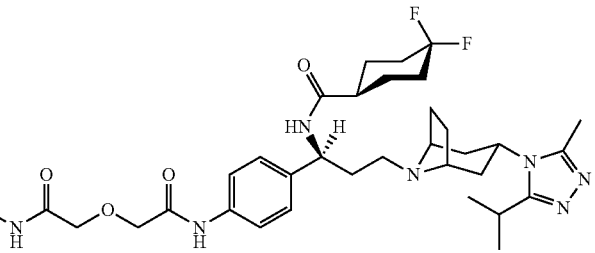

In some embodiments of the method to treat neuroAIDS, the subject abuses or is addicted to opiates.

The invention also provides methods of blocking entry of a human immunodeficiency virus (HIV) into an astrocyte. The methods comprise a step of exposing the astrocyte to at least one bivalent ligand of Formula I,

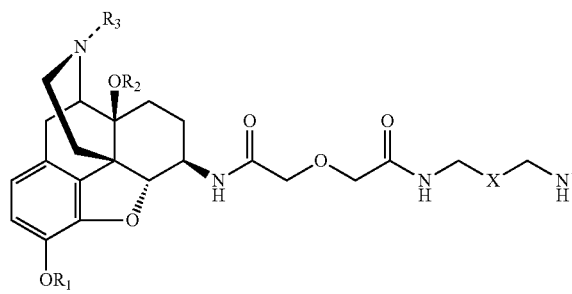
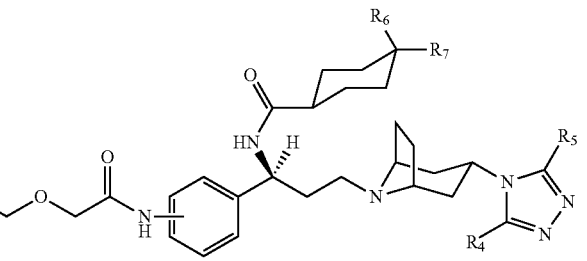

Formula I wherein $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;

$R_3$ may be present or absent and may be H; $H_2$; O; $C_{1-12}$alkyl; —$COOR_9$ where $R_9$ is alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;

R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group; and X=a branched or unbranched, saturated or unsaturated carbon chain comprising from 1-20 carbon atoms, and may include a heteroatomic group; as well as salts, hydrates, protonated and unprotonated and stereoisomeric forms thereof. In some embodiments, the step of exposing is carried out in the presence of an opiate. In some embodiments, the opiate is morphine.

MVC; p<0.05 vs. R5+M+MVC+naltrexone). B. Cellular localization of HIV-1 in astroglial cells infected with an R5-tropic HIV-1$_{Bal}$-Vpr-GFP reporter virus was readily detectable (arrows) by confocal microscopy. Cell nuclei are counterstained with DAPI. Incubation with the bivalent ligand (lower panel) inhibits viral entry. Images are optical sections from a single Z-plane with the acquisition parameters set to optimize X-, Y-, and especially Z-plane resolution.

Figure 4:
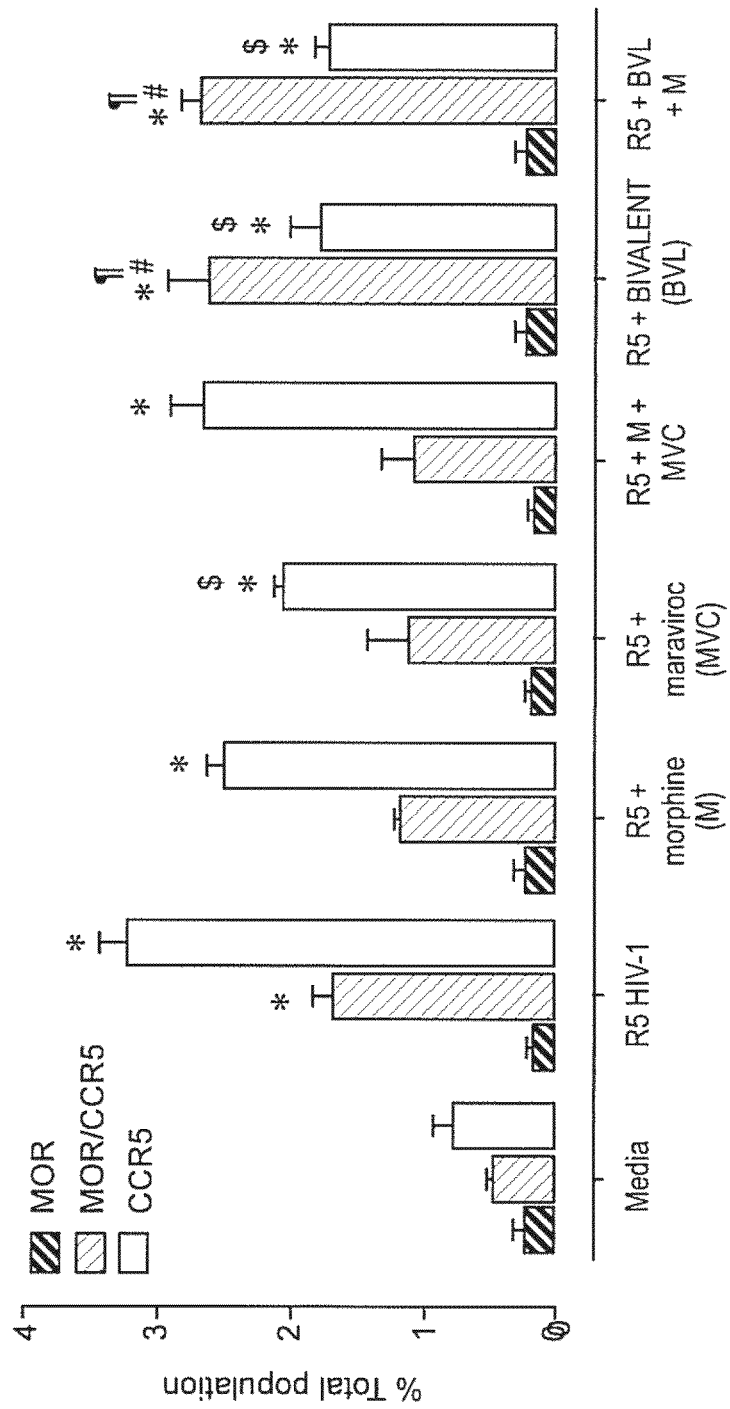

FIG. 4. Flow cytometric analysis of CCR5 and MOR immunofluorescence in primary human astrocytes. Graphs represent the data obtained from histograms of three independent experiments; values in each histrogram indicate the mean percentages of total cell population±SEM in which 488-green labeled CCR5, APC-red labeled MOR, or co-localization of both receptors could be detected. (*p<0.005 vs. un-infected cells; $^{\$}$p<0.05 vs. HIV-1; $^{\#}$p<0.05 vs. R5+morphine; $^{¶}$p<0.05 vs. R5+maraviroc; $^{\$}$p<0.05 vs. R5+morphine+MVC).

Figure 5:
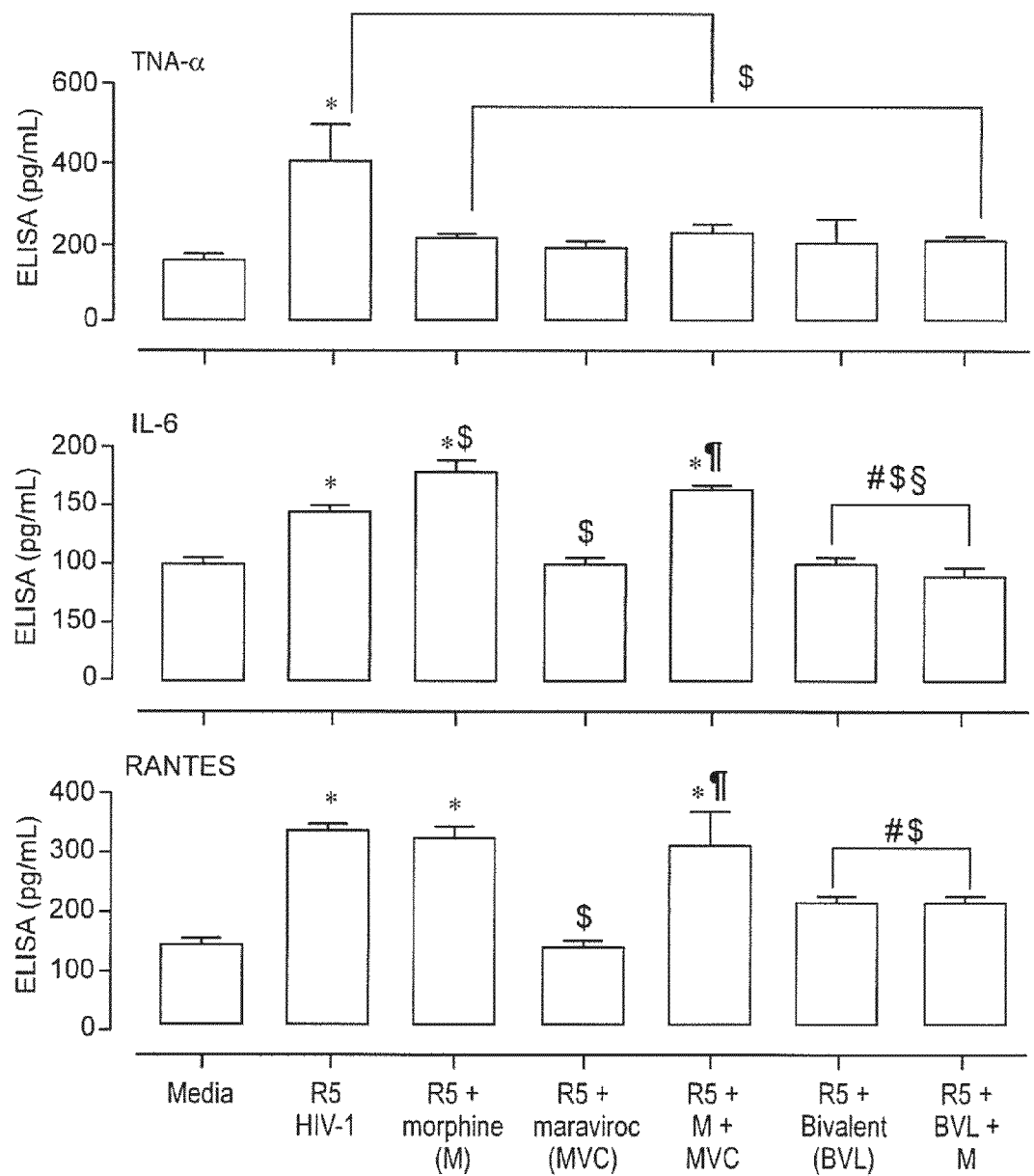

FIG. 5. Protein levels of TNF-α, IL-6, IL-1β and RANTES were measured by ELISA from supernatants of HIV-1 infected astroglia. Values are based on standard curves±SEM of 3 independent experiments at 18 h post-infection. (*p<0.005 vs. un-infected cells; $^{\$}$p<0.05 vs. HIV-1; $^{\#}$p<0.05 vs. R5+morphine; $^{¶}$p<0.05 vs. R5+maraviroc; $^{\$}$p<0.05 vs. R5+morphine+MVC).

Figure 6:
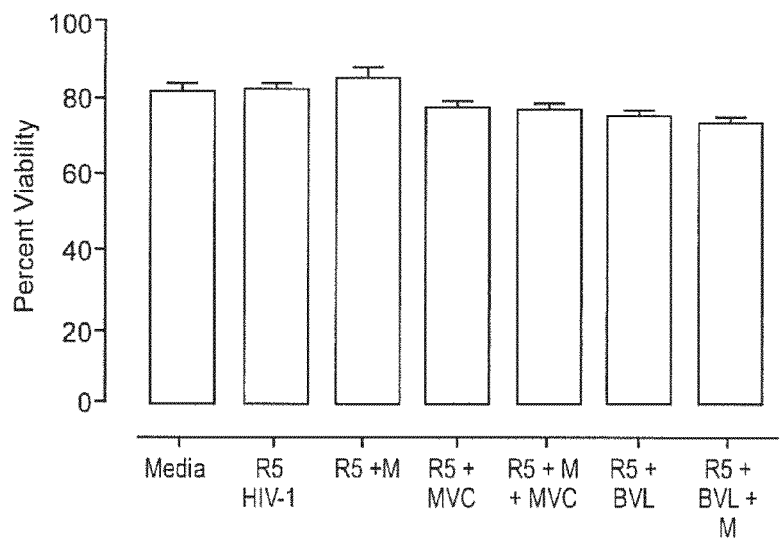

FIG. 6. HIV-1±morphine did not affect the viability of astroglial cells irrespective of pretreatment with viral inhibitors. Human astrocytes were infected with the R5 tropic HIV-1 (50 pg/ml), exposed with maraviroc (MVC; 100 nM) or the bivalent ligand (BVL: 100 nM) with or without morphine (M; 500 nM). Cell viability, assessed by the measurement of both live and dead cells using dual (green/red) fluorescence labeling with AOPI, was unaffected by infection at 24 h following continuous exposure. Data are percent viability±SEM from three independent experiments.

Figure 7:
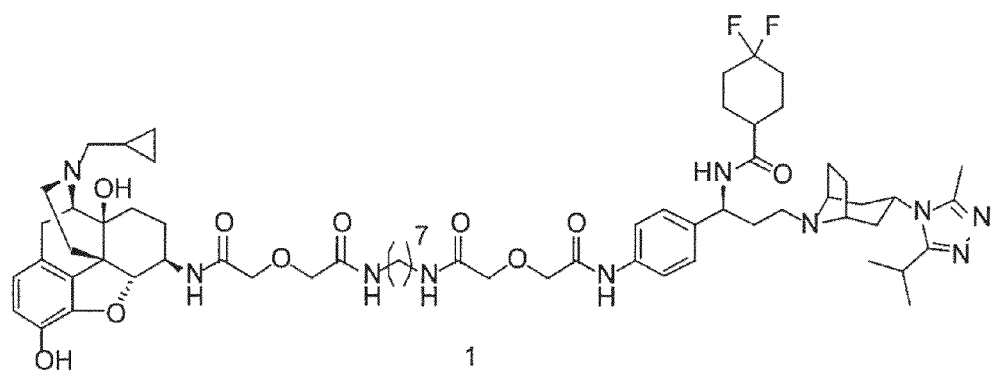
Figure 7:
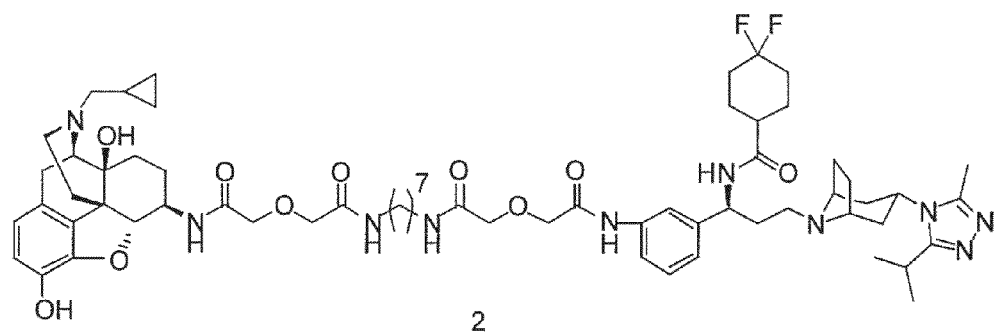

FIG. 7. Structures of bivalent compounds 1 (VZMC1) and 2 (VZMC5).

Figure 8:
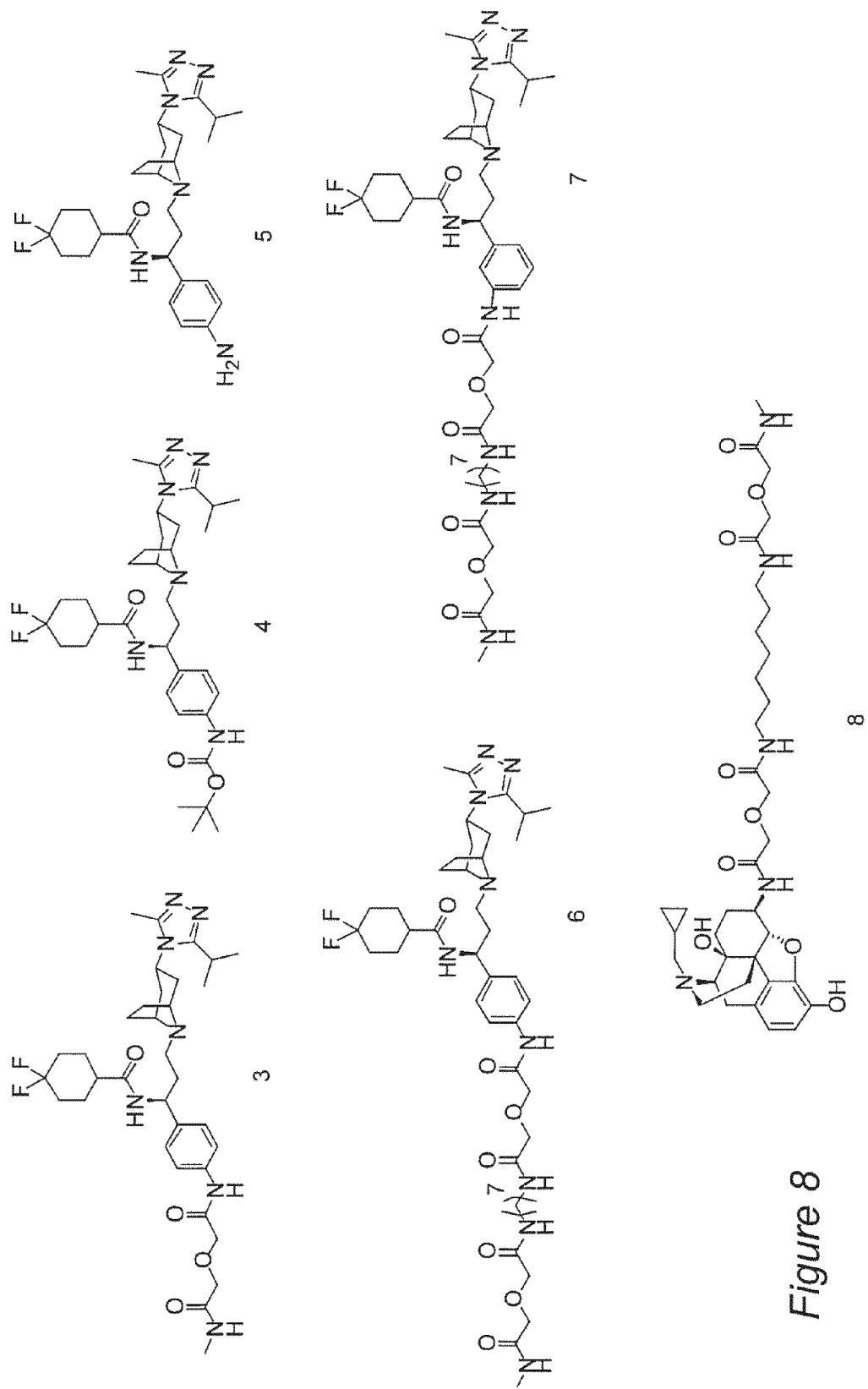

FIG. 8. Structure of various control compounds.

Figure 9:
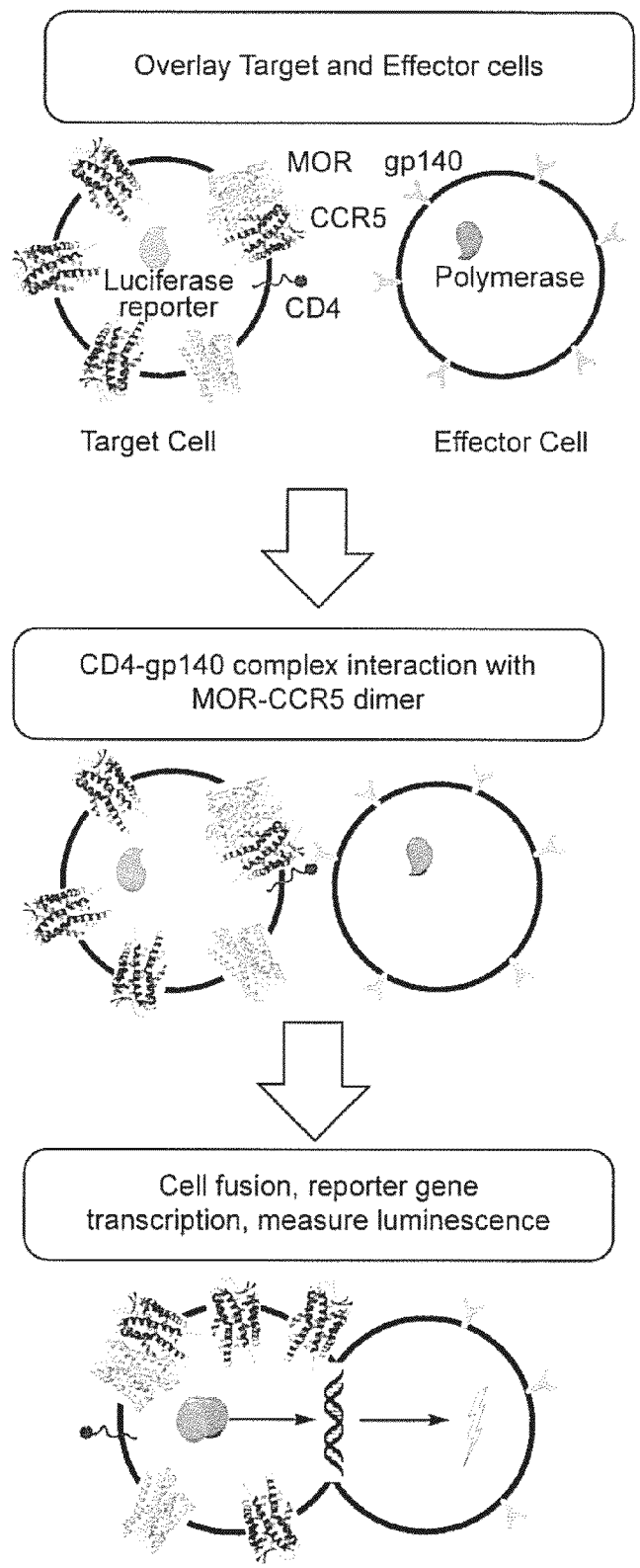

FIG. 9. Cell fusion assay used to mimic HIV invasion without using live virus.

Figure 10:
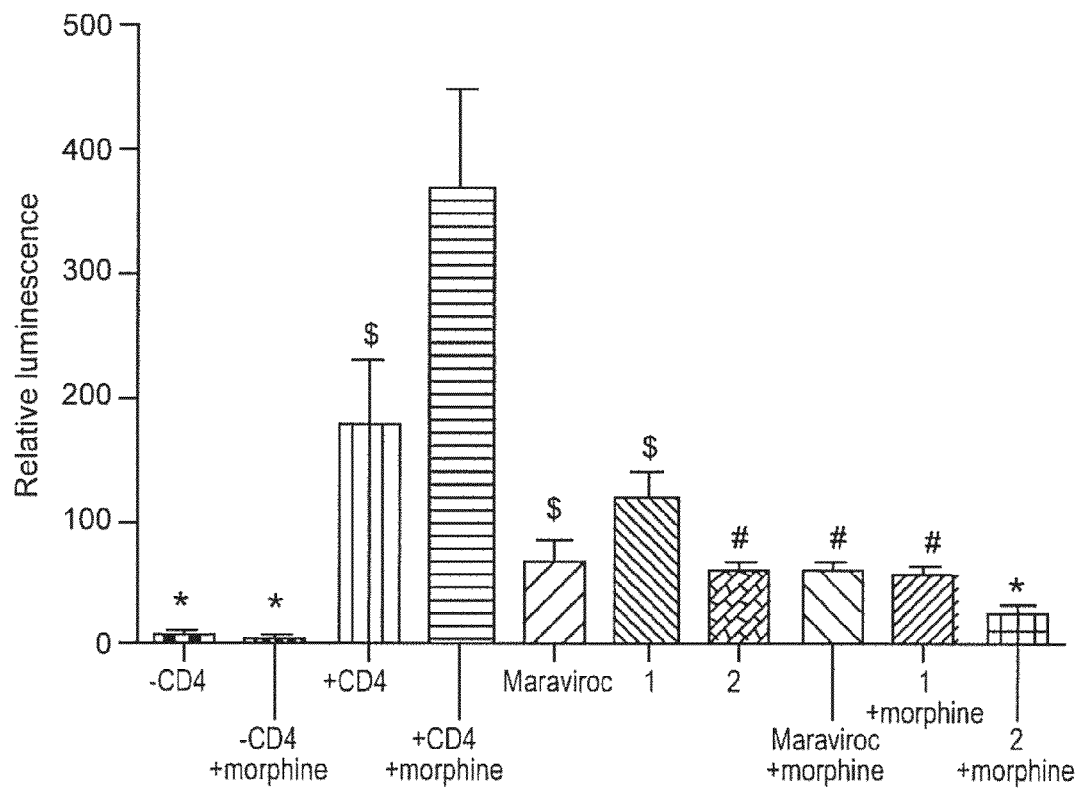

FIG. 10. Cell fusion assay based upon luminescene from expressed luciferase reporter gene. For morphine stimulation, 300 nM was added. 100 nM Maraviroc, 3000 nM 1, and 10000 nM 2 was used. Values are representative of 4 assays run. (*p<0.001 vs.+CD4+morphine; $^{\$}$p<0.05 vs.+CD4+morphine; $^{\#}$p<0.01 vs.+CD4+morphine).

Figure 11:
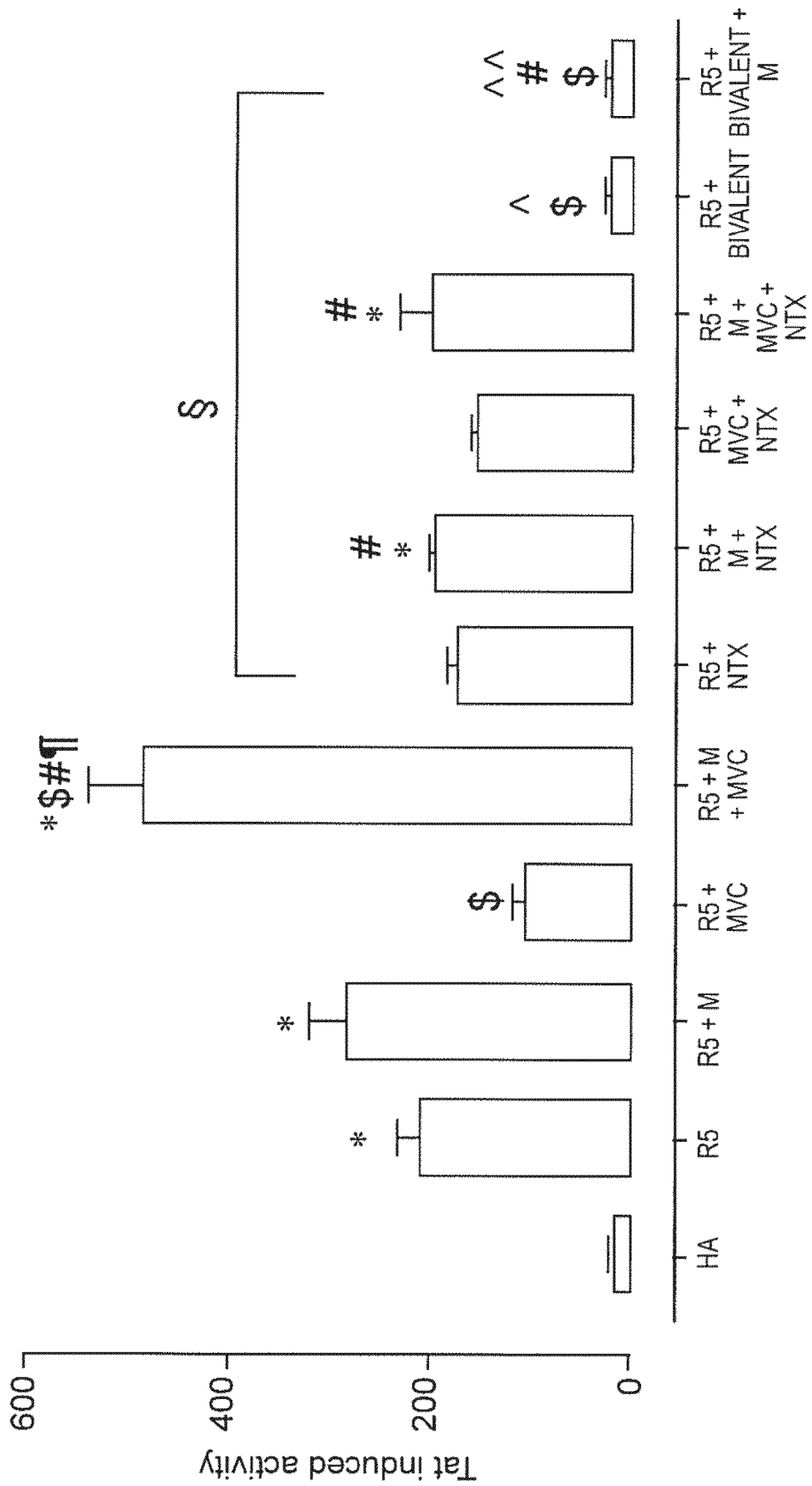

FIG. 11. HIV-1$_{SF162}$ infectivity in human glial was determined based on the relative amount of Tat protein expressed by the virus using a luciferase based assay. (HA) human astrocytes, (R5) HIV-1$_{SF162}$, (M) morphine at 500 nM, (MVC) maraviroc at 100 nM, (bivalent) compound 1 at 100 nM, and (NTX) naltrezone at 1500 nM. Values are absorbance±SEM of 3 independent experiments at 18 h post-infection (*p<0.005 vs. un-infected cells; $^{\$}$p<0.05 vs. R5 HIV-1; $^{\#}$p<0.05 vs. opioid; $^{¶}$p<0.05 vs. maraviroc (MVC); $^{\$}$p<0.05 vs. morphine+MVC; $^{\wedge}$p<0.05 vs. MVC+NTX; $^{\wedge\wedge}$p<0.05 vs. morphine+MVC+NTX; $^{\Omega}$p<0.05 vs. bivalent).

Figure 12:
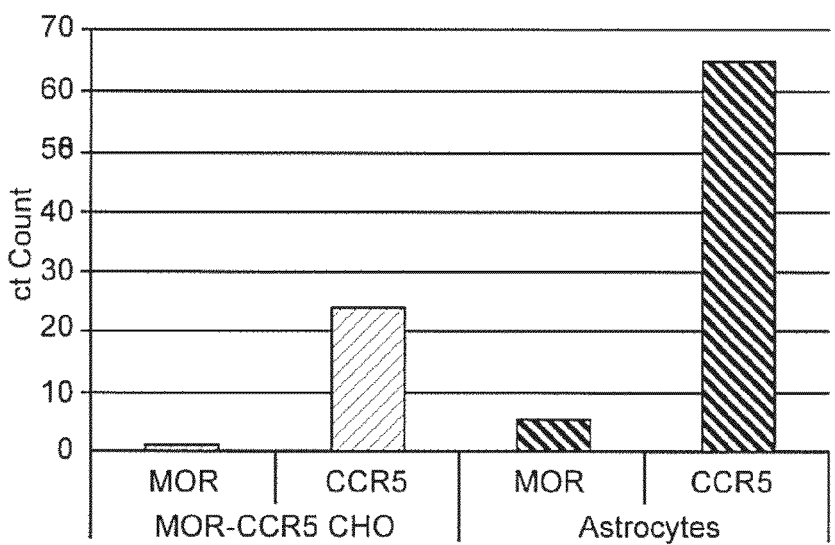

FIG. 12. mRNA levels of MOR and CCR5 in the CCR5-MOR CHO cell line and in two lots of primary human astrocytes.

Figure 13:
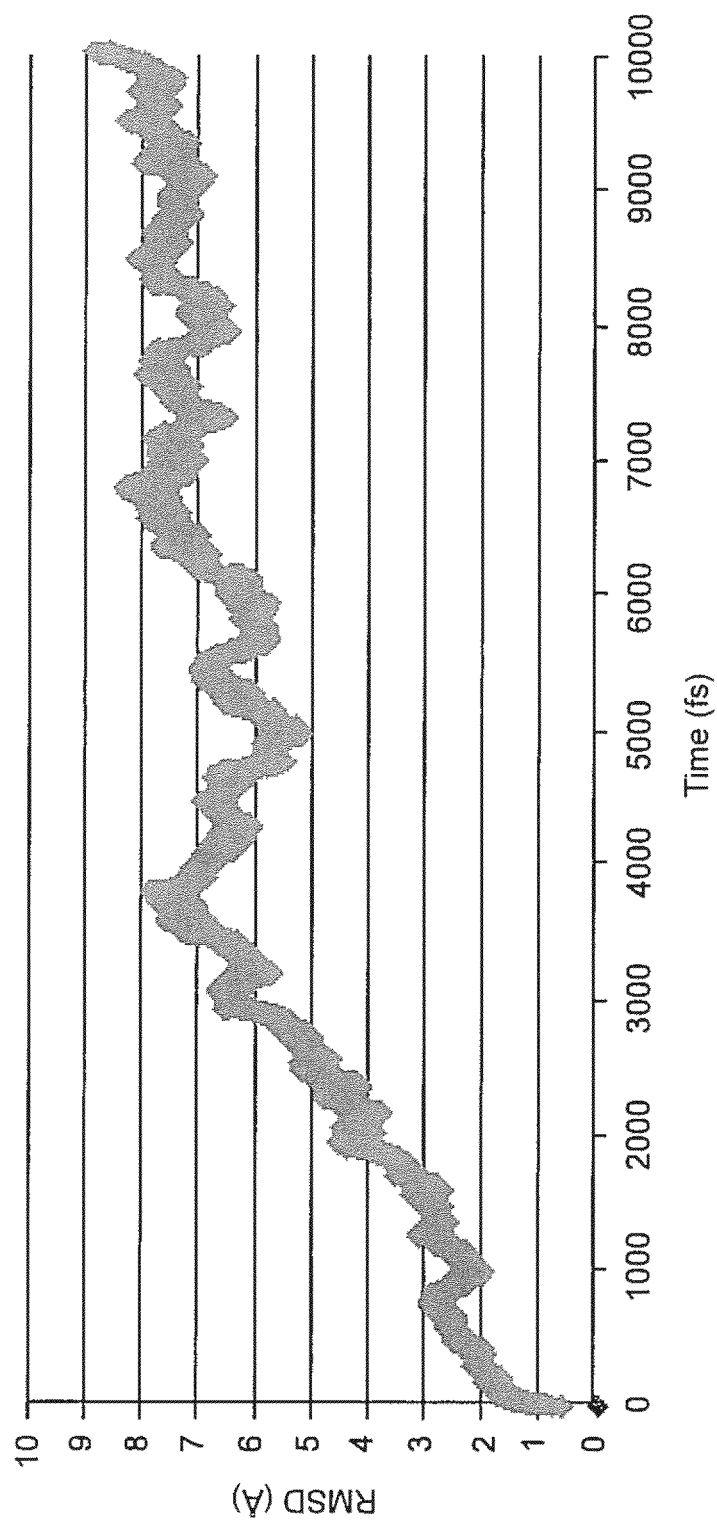

FIG. 13. CCR5-MOR heterodimer RMSD from initial molecular dynamics study after a total of 10 ns of production.

Figure 14:
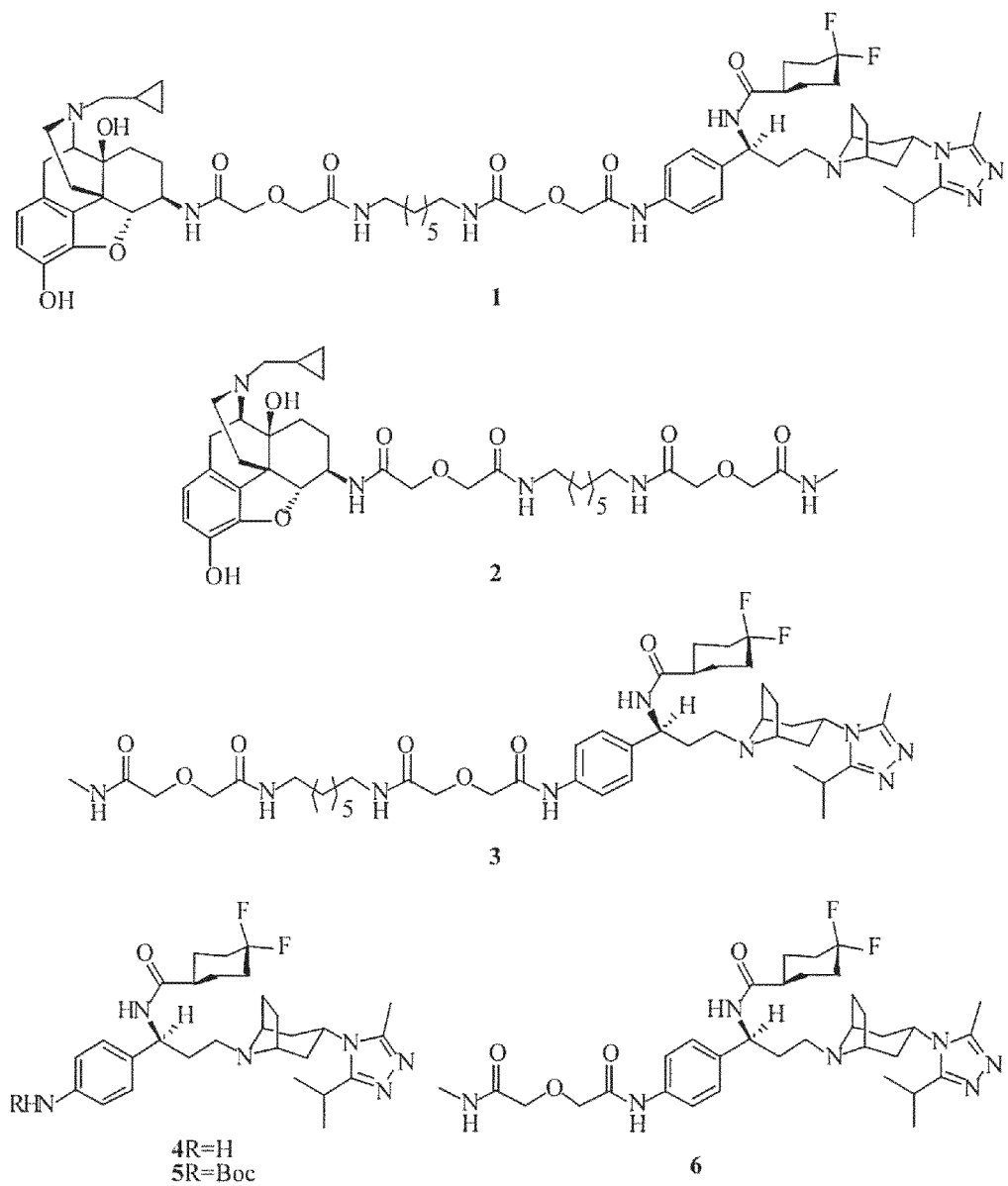

FIG. 14. Chemical structures of bivalent ligand (1), monovalent ligands (2, 3, 6), and maraviroc analogues, 4 and 5.

Figure 15:
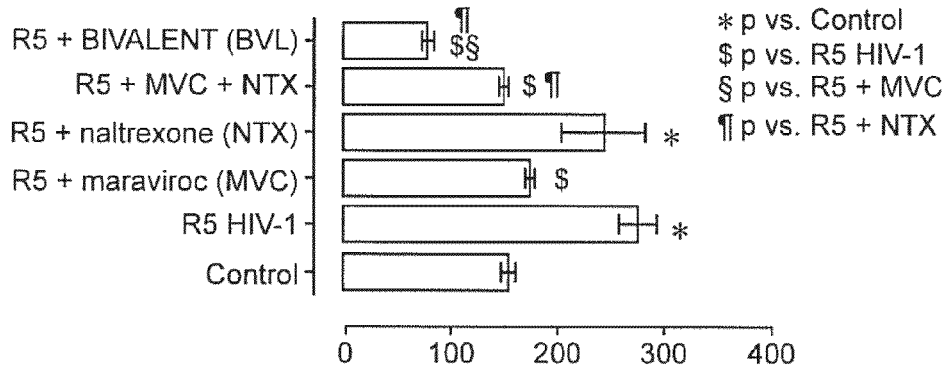

FIG. 15. HIV-1$_{SF162}$ infectivity in human astrocytes (HA) was determined based on the relative amount of Tat protein expressed by the virus using a luciferase based assay. Dose response effect was first studied for each compound (not shown). Values are absorbance±SEM of three independent experiments at 18 h post-infection [Maraviroc (MVC), 100 nM; naltrexone (NTX), 1.5 µM; bivalent ligand 1, 100 nM; *p<0.005 vs. uninfected cells (control); $^{\$}$p<0.05 vs. R5 HIV-1; $^{\$}$p<0.05 vs. R5+MVC; $^{¶}$<0.05 vs. R5+NTX].

Figure 16:
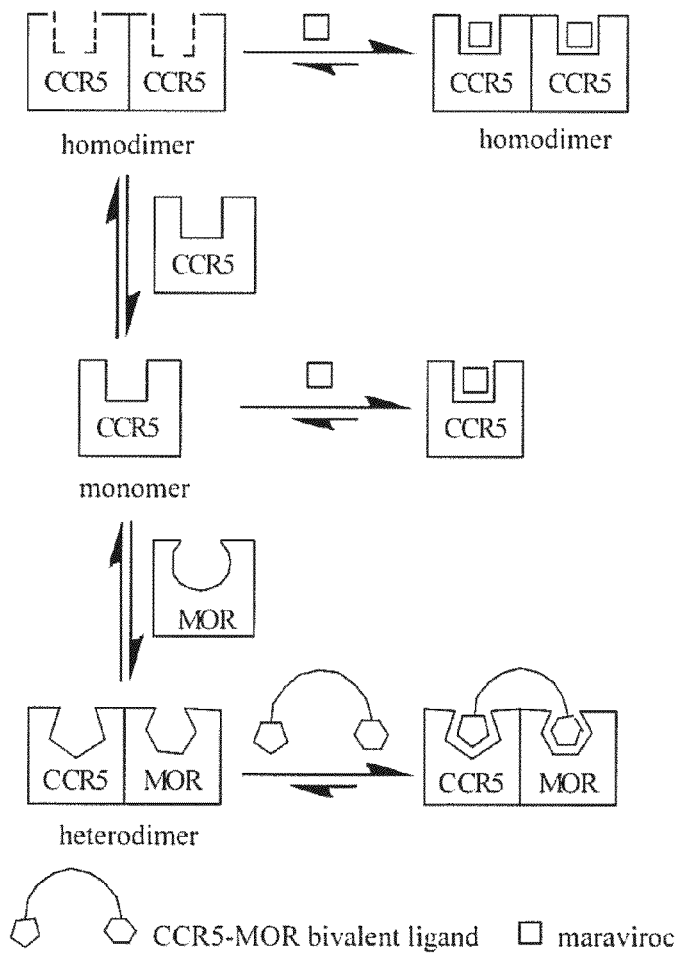

FIG. 16. Schematic illustration of the proposed mechanism for the "functional selectivity" of bivalent ligand 1 and maraviroc in the radioligand binding assay, $Ca^{2+}$ flux inhibition assay, and HIV-1 invasion assay. The CCR5 receptor may exist as monomer or form homodimers in the monocloned receptor expressed assays while the CCR5 and the MOR may exist as heterodimers in the human astrocytes and the CCR5 binding pocket in the heterodimer might accommodate the bivalent ligand preferably.

DETAILED DESCRIPTION

Bivalent ligands useful for the treatment of neurological disorders caused or exacerbated by the interaction of the receptors MOR and CCR5 are provided. Data presented herein showed that the CCR5 ligand maraviroc inhibits HIV-1 entry into astrocytes, while morphine negates the effects of maraviroc leading to a significant increase in viral entry. However, utilizing maraviroc in the form of a naltrexone-maraviroc bivalent ligand has a more potent inhibitory effect on R5-tropic viral entry in astrocytes than maraviroc alone. Significantly, the inhibitory effects of the bivalent compound were not compromised by morphine. Moreover, exposure to maraviroc or the bivalent compound decreased the release of pro-inflammatory cytokines and restricted HIV-1-dependent increases in CCR5 expression. The results suggest that opiate abuse limits the antiretroviral effects of maraviroc, thus likely accelerating brain neuropathogenesis.

In addition, the bivalent compounds are potent inhibitor in both an artificial cell fusion assays mimicking HIV invasion and in native HIV invasion assays using live virus. Importantly, in the native cell HIV invasion assay maraviroc was unable to inhibit HIV infection in the presence of morphine in primary human astrocytes. However, an exemplary bivalent compound was a more potent inhibitor than maraviroc in primary human astrocytes with and without morphine (3.3-fold higher virus inhibition than maraviroc without morphine, and 7-fold higher virus inhibition than maraviroc with morphine). Thus, targeting the CCR5-MOR heterodimer using the bivalent ligands is an efficacious antiviral treatment to treat neuroAIDS.

The use of the bivalent ligands as therapeutics advantageously avoids drug-drug interactions which frequently occur when two separate pharmacophores are utilized together. Also, by providing a single, effective agent, dosing and compliance with treatment regimens are facilitated. The bivalent ligands have been shown to readily cross the blood-brain-barrier, and to be highly effective in disrupting MOR/CCR5 interactions. Thus, the coordinated blockade of MOR and CCR5, using the novel bivalent compounds described herein, is a viable therapeutic strategy, especially in drug-abusing HIV-infected populations.

Without being bound by theory, it is believed that the binding of one of the two ligands to its receptor in effect increases the local concentration of the other ligand, thereby increasing its chances of "finding" its cognate receptor and binding thereto. Thus, the tethering or attachment of the two ligands to each other insures that both receptors will or are likely to be blocked and unable to interact with one other.

The bivalent ligands are based on and are derivatives or variants of the MOR ligand naltrexone and the CCR5 ligand maraviroc, and have generic formula I:

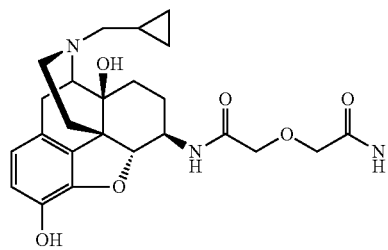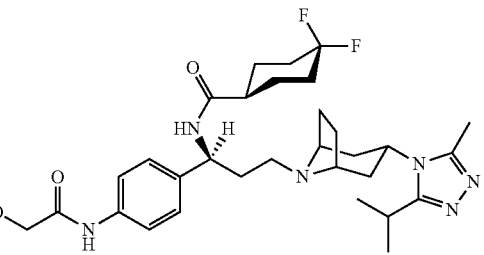

wherein $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; $SO_4^{-2}$;

$R_3$ may be present or absent and may be H; $H_2$; O; alkyl; —$COOR_9$ where $R_9$ is $C_{1-12}$alkyl); $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen (e.g. F, Cl, Br, etc.); a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be bonded (fused) to an N or C atom of the triazole ring, and may or may not be aromatic; or a heteroatomic group such as $COO^-$, $NO_2^-$, $NO_3^-$, $SO_3^-$, or $SO_4^{2-}$;

R6 and R7 may be the same or different, and are independently selected from: H; halogen (e.g. F, Cl, Br, etc.); a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be bonded to an N or C atom of the hexane ring, and may or may not be aromatic; or a heteroatomic group such as $COO^-$, $NO_2^-$, $NO_3^-$, $SO_3^-$, $SO_4^{2-}$; and X=a branched or unbranched, saturated or unsaturated carbon chain comprising from about 1 to about 20 carbon atoms, and may include a heteroatomic group such as $COO^-$, $NO_2^-$, $NO_3^-$, $SO_3^-$, or $SO_4^2$; as well as salts, hydrates and protonated and unprotonated and charged forms thereof. Stereoisomers of the structure are also contemplated.

Examples of suitable or polycyclic saturated or unsaturated homo- or heterocyclic ring system comprising 1, 2, 3, 4, or more rings with from 3 to 7 atoms per ring in the system, which may or may not be aromatic include but are not limited to: pyrolyl, pyranyl, cyclopropyl, cyclobutyl, cyclohexanyl, etc.

Examples of suitable saturated or unsaturated, branched or unbranched, substituted or unsubstituted carbon groups or chains comprising from 1-20 carbon atoms include but are not limited to: methyl, ethyl, n-propyl, isopropyl, n-butyl, allyl, etc.

Examples of suitable $C_1$-$C_{20}$ branched or unbranched, saturated or unsaturated carbon chains include but are not limited to: methyl, ethyl, n-propyl, isopropyl, n-butyl, allyl, etc.

In one embodiment, the bivalent ligand has the chemical formula depicted in Formula I:

Diseases and conditions that can be treated using the pharmacological agents described herein include but are not limited to neurological disorders which result from or are associated with the interaction of the receptors MOR and CCR5. Such diseases/disorders include but are not limited to: neurodegeneration of any type e.g. those caused by bacterial or viral infections such as those described below for HIV; Alzheimer's disease; Parkinson's disease; dementia; drug (opioid) abuse and/or addiction, opioid use and/or addiction in those being treated for pain; etc.

In some embodiments, the diseases or conditions are associated with individuals whose immune systems are compromised, e.g. as a result of medical treatments (e.g. chemotherapy, etc.), as a result of disease such as human immunodeficiency virus infection/acquired immunodeficiency syndrome (HIV/AIDS), as a result of one or more genetic disorders or mutations, as a result of environmental insult or challenges (e.g. poor nutrition, excessive stress, pollutants, etc.), or due to advancing age.

In some embodiments, the diseases are neurological diseases associated with (co-morbid with) HIV/AIDS, a disease of the human immune system caused by the human immunodeficiency virus (HIV). In some embodiments, the patients that are treated are HIV positive but have not yet developed symptoms of the disease (i.e. are asymptomatic) and/or are in the very early stages of the disease. In other embodiments, the patients/subjects have "full-blown" AIDS. HIV-associated neurocognitive disorders (HAND), which includes a spectrum of syndromes (including: asymptomatic neurocognitive impairment (ANI), minor neurocognitive disorder (MND), the more severe HIV associated dementia (HAD) may be treated.

Accordingly, conditions that may be treated using the bivalent ligands of the invention in this context include but are not limited to: so-called neuroAIDS, neurodegeneration, Alzheimer's disease, Parkinson's disease, dementia, pain management, AIDS, HIV infection, drug (opioid) abuse and addiction, and others. See, for example, the website located at www.ninds.nih.gov/disorders/aids/detail_aids. AIDS-related disorders of the nervous system may be caused directly by the HIV virus, by certain cancers and opportunistic infections (illnesses caused by bacteria, fungi, and other viruses that would not otherwise affect people with healthy immune systems), or even by toxic effects of the drugs used to treat symptoms. Also included are AIDS dementia complex (ADC), or HIV-associated dementia (HAD), symptoms of which may include encephalitis (inflammation of the brain), behavioral changes, and a gradual decline in cognitive function, including trouble with concentration, memory, and attention; progressive slowing of motor function and loss of dexterity and coordination, as well as milder cognitive complaints such as HIV-associated neurocognitive disorder (HAND). In addition, central nervous system (CNS) lymphomas (e.g. those associated with the Epstein-Barr virus), may be treated, as may symptoms thereof, including headache, seizures, vision problems, dizziness, speech disturbance, paralysis, and mental deterioration. Symptoms of cryptococcal meningitis are seen in about 10 percent of untreated individuals with AIDS and in other persons whose immune systems have been severely suppressed by disease or drugs. It is caused by the fungus *Cryptococcus neoformans*, which is commonly found in dirt and bird droppings. The fungus first invades the lungs and spreads to the covering of the brain and spinal cord, causing inflammation. Symptoms include fatigue, fever, headache, nausea, memory loss, confusion, drowsiness, and vomiting, and may be treated using the agents and methods described herein. Similarly, cytomegalovirus (CMV) infections e.g. CMV encephalitis, and symptoms thereof may be treated. Symptoms of CMV infection include weakness in the arms and legs, problems with hearing and balance, altered mental states, dementia, peripheral neuropathy, coma, and retinal disease. CMV infection of the spinal cord and nerves can result in weakness in the lower limbs and some paralysis, severe lower back pain, and loss of bladder function, as well as pneumonia and gastrointestinal disease. In addition, neurological symptoms of herpes virus infections may be treated, examples of which include herpes zoster virus e.g. encephalitis and myelitis (inflammation of the spinal cord). Other forms of neuropathy, or nerve damage and pain may also be treated, e.g. peripheral neuropathy (damage to the peripheral nerves); distal sensory polyneuropathy; neurosyphilis, e.g. the result of an insufficiently treated syphilis infection, with symptoms that include weakness, diminished reflexes, unsteady gait, progressive degeneration of the joints, loss of coordination, episodes of intense pain and disturbed sensation, personality changes, dementia, deafness, visual impairment, and impaired response to light; progressive multifocal leukoencephalopathy (PML), caused by the John Cunningham (JC) virus, which infects multiple brain sites and destroys cells that make myelin, symptoms of which include various types of mental deterioration, vision loss, speech disturbances, ataxia (inability to coordinate movements), paralysis, brain lesions, compromised memory and cognition, seizures and coma. Individuals treated for HIV may also experience other conditions that may be treated by the agents and methods of the invention, such as anxiety disorder, depressive disorders, increased thoughts of suicide, paranoia, dementia, delirium, cognitive impairment, confusion, hallucinations, behavioral abnormalities, malaise, and acute mania, from a variety of causes (e.g. the virus itself, or the medications used to treat the disease). In addition symptoms of toxoplasma encephalitis (cerebral toxoplasmosis), caused by the parasite *Taxoplasma gondii*, may be treated, including encephalitis, fever, severe headache that does not respond to treatment, weakness on one side of the body, seizures, lethargy, increased confusion, vision problems, dizziness, problems with speaking and walking, vomiting, and personality changes. Symptoms associated with vacuolar myelopathy may also be treated, e.g. weak and stiff legs and unsteadiness when walking, AIDS dementia, etc.

In yet other embodiments, the disease that is treated is multiple sclerosis, particularly since low dose naltrexone has been suggested for use in such treatment. In fact, and disease or conditions for which naltrexone and/or maraviroc are used or suggested for use may be treated using the bivalent ligands described herein.

In some embodiments, the individuals who are treated already exhibit gross, observable and usually measurable symptoms of neurological damage. In such instances, the methods may include a step of identifying individuals suitable for receiving treatment using known neurological examination techniques and other tests such as blood tests, viral and/or bacterial culture, etc. Patients identified as positive for symptoms and deemed candidates for treatment.

However, in some embodiments, the individuals who can benefit form receiving the agents described herein do not yet display overt symptoms of disease but are known to be at risk of developing neurological disorders. For example, a person would be a candidate for prophylactic treatment even prior to the emergence of overt symptoms of neurological disease or distress might include one who is: known to be HIV positive, or is known to abuse or be addicted to opiates, or is going to undergo chemotherapy other immuno-compromising procedure, or a person known to have any other disease or condition (e.g. a genetic predisposition) toward developing a compromised immune system and/or neurological damage or neurodegeneration.

The individuals who are treated using the agents and methods of the invention are generally mammals, and usually but not always are humans, since veterinary applications of this technology are also contemplated. The individuals may be adults or juveniles (e.g. children).

The present invention also provides compositions for use in preventing and/or treating neurological disorders and/or dysfunction. The compositions include one or more substantially purified bivalent ligands as described herein, and a pharmacologically (physiologically) suitable carrier. The preparation of such compositions is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. In subjects who are HIV positive, anti-viral medications may be administered together with the bivalent ligands of the invention, either separately in different preparations, or together in the same preparation. The final amount of bivalent ligand in the formulations may vary. However, in general, the amount in the formulations will be from about 1-99%.

The bivalent ligand compositions (preparations) of the present invention may be administered by any of the many suitable means which are well known to those of skill in the art, including but not limited to by injection (e.g. intravenous, intraperitoneal, intramuscular, subcutaneous, intra-aural, intraarticular, into the spinal column, intracranial, and the like); by inhalation; orally; intravaginally, intranasally, topically (by absorption through epithelial or mucocutaneous linings e.g., nasal, oral, vaginal, rectal, gastrointestinal mucosa, and the like); as eye drops; via sprays, etc. In preferred embodiments, the mode of administration is by injection. In addition, the compositions may be administered in conjunction with other treatment modalities such as substances that boost the immune system, various chemotherapeutic agents, antibiotic agents, and the like.

Also provided herein are methods of preventing, treating or reversing the symptoms of neurological disorders. In some embodiments, the neurological disorders that are treated are associated with HIV infection. The methods involved administering to a subject (patient) in need thereof a therapeutically effective amount of one or more of the bivalent ligands described herein. The exact dosage that will be administered, as well as the mode and frequency of administration, will vary from subject to subject, with guidance being provided by clinical trials data. However, in general, because the two chief components of the bivalent ligand are already known, it is believed that a dose in the range of from about from 1 mg to about 600 mg per day, more specifically from about 10 mg to about 100 mg range, is administered, for example, about 1, 2, 3, or 4 times per day, unless administered intravenously in which case the dosage is adjusted accordingly to achieve suitable biologically active and effective levels of the agent(s) in the subject's bloodstream. In some embodiments, the dose is adjusted to match or approximate or overlap, on a molar basis, typical doses of maraviroc, for which the FDA approved dose is 300 mg twice daily, and/or naltrexone for which the FDA approved dose is 50 to 150 mg per day, although due to the higher activity of the bivalent ligand, less is generally required to achieve the same level of efficacy.

Also provided are methods of blocking entry of a human immunodeficiency virus (HIV) into an astrocyte. Astrocytes are also known collectively as astroglia, and are characteristic star-shaped glial cells in the brain and spinal cord. The methods comprise a step of exposing the astrocyte to one or more of the bivalent ligands as described herein, in a quantity sufficient to block HIV entry. By "blocking" we mean that entry of an HIV into an astrocyte (which would otherwise possibly or likely be infected by the HIV) is prevented entirely, or at least slowed, compared to (relative to) a control situation in which the HIV freely attaches to and enter the astrocyte. "Blocking" can also mean that, if multiple HIVs are attempting to infect an astrocyte, then fewer of them are successful than would be the case if the bivalent compound(s) were not present. In some embodiments, the method is carried out or occurs in the presence of an opiate such as morphine.

The agents of the invention may also be used as research tools, e.g. to characterize and study dimerization between the mu opioid receptor (MOR) and the chemokine CCR5 receptor, as well as the role of dimerization in neurological disorders. Further, the agents may be used to study the neurological disorders themselves, e.g. neuro-AIDS, neurodegradation, dementia, etc., thereby improving the understanding of role of the receptors in neurological disorders, and accelerating the development of treatment methods.

EXAMPLES

Example 1

Design and Synthesis of an Exemplary Bivalent Ligand

1

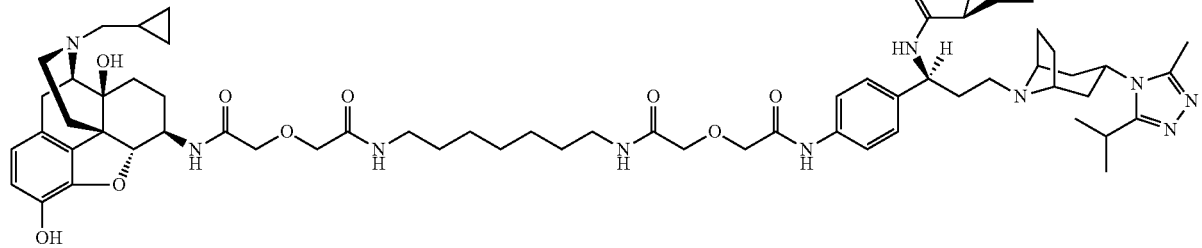

A bivalent ligand 1 was designed and synthesized as the first molecular probe to study the biological and pharmacological mechanisms of the putative mu opioid receptor and chemokine receptor CCR5 heterodimers.

Abstract

The bivalent ligand approach has been utilized not only to study the underlying mechanism of G protein-coupled receptors dimerization and/or oligomerization, but also aimed to enhance ligand affinity and/or selectivity for potential treatment of a variety of diseases by targeting on this process. Substance abuse and addiction have made both the prevention and the treatment of human immunodeficiency virus (HIV) infection more difficult to tackle. It has been extensively studied that morphine, a mu opioid receptor (MOR) agonist, can accelerate HIV infection through up-regulating the expression of the chemokine receptor CCR5, a well-known co-receptor for HIV invasion to the host cells. Meanwhile, two research groups have described the putative MOR/CCR5 heterodimers in their independent studies. The design and synthesis of an exemplary bivalent ligand and its biological and pharmacological processes for the putative MOR/CCR5 dimerization phenomenon are described herein. The developed bivalent ligand thus contains two distinct pharmacophores linked through a spacer; ideally one of which will interact with the MOR and the other with the CCR5. Naltrexone and Maraviroc were selected as the exemplary pharmacophores to generate such a bivalent probe. The overall reaction route to prepare this bivalent ligand was convergent and efficient, and involved sixteen steps with moderate to good yields. The preliminary biological characterization showed that the bivalent compound 1 retained the pharmacological characteristics of both pharmacophores towards the MOR and the CCR5 respectively, which tentatively validated our original molecular design.

Introduction

Since acquired immunodeficiency syndrome (AIDS) was identified three decades ago, the global prevalence of AIDS has become stable at 0.8%, with over 33 million people infected with human immunodeficiency virus (HIV) in 2007. There are almost 16 million people who are injecting drug users (IDUs) worldwide and nearly 10% of HIV infection was attributed to injecting drug use through contaminated needles. Statistics showed IDUs account for approximately 13% of the total HIV infection in thirty-four US states during 2004 to 2007. Not only driving HIV transmission among IDUs, the abused substances, such as opioids, cocaine, and alcohol also accelerate the progression of AIDS and complicate the treatment of this disease. Moreover, HIV infection seems to increase drug addiction vulnerability as well. Needle-exchange programs (NEPs) have shown appreciable outcome on reducing HIV prevalence among IDUs for over a decade. The current available treatment for opioid-dependent HIV patients also adopts opioid substitution therapy (OST), i.e. methadone, buprenorphine and buprenorphine/naloxone, into HIV management. Although opioid maintenance therapy have shown to improve patients adherence and promising outcome for HIV treatment, the adverse drug-drug interaction between methadone, buprenorphine and antiretroviral agents compromise the overall effects. New agents and remedies are still highly demanded for the treatment of these patients.

Figure 1:
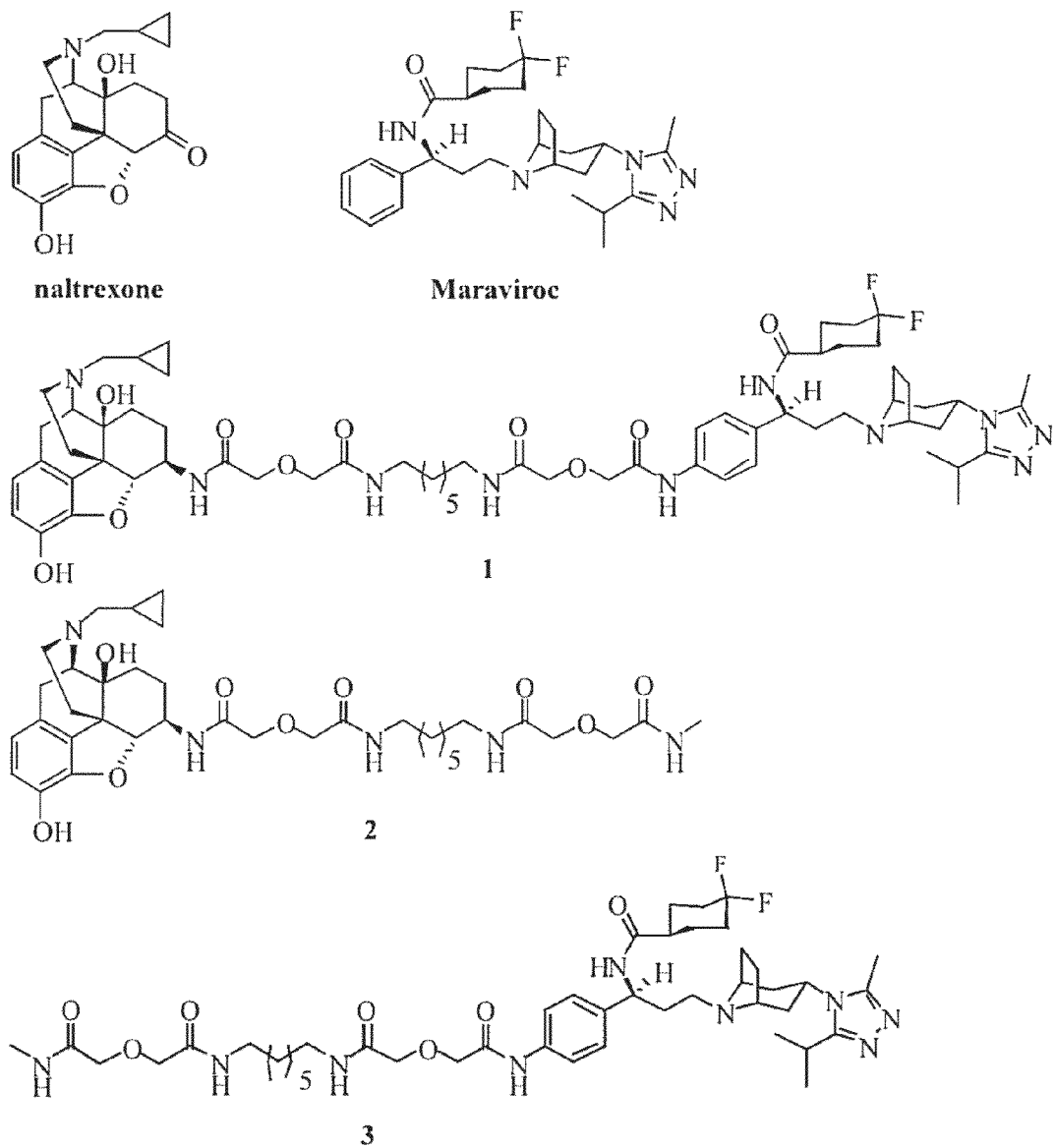
FIG. 1. Chemical structures of naltrexone, Maraviroc, designed bivalent (1) and monovalent ligands (2, 3).

Opiates and alcohol abuse/addiction liability is mainly associated with the mu opioid receptor (MOR), which is also involved in different immunomodulatory activities induced by opioids. The chemokine receptor CCR5 was identified as a major co-receptor for HIV in 1996, and is largely expressed on activated memory CD45RO$^-$ T cells, monocyte/macrophages, dendritic cells, granulocyte precursors, and natural killer cells. Despite fundamental studies, a chemical probe that is capable of interacting with both receptors simultaneously has never been developed to facilitate the study of the biological and pharmacological process of MOR/CCR5 dimerization. Herein, we report the design, synthesis and testing of a bivalent ligand 1 (FIG. 1).

Bivalent Ligand Rational Design

Receptor antagonists serve as important pharmacological probes to uncover the probable involvement of a receptor mechanism. Therefore, it seemed ideal to build a bivalent ligand containing a MOR-antagonist moiety as well as a CCR5-antagonist one, linked through an appropriate spacer. Naltrexone (FIG. 1) was selected as the moiety to interact with the MOR based on the following considerations: first, naltrexone has been successfully used to investigate the dimerization of opioid receptors previously; second, it represents an ideal treatment for alcohol and opiate addiction and has been successfully used to treat alcoholism clinically. Maraviroc (FIG. 1) is the only CCR5 antagonist that has been approved for HIV treatment by the FDA so far and thus became our first of choice as the CCR5 pharmacophore. Meanwhile, both of these two ligands showed high affinity and reasonable selectivity toward the MOR and the CCR5 respectively.

It has been proved that the loci for tethering two pharmacophores through a spacer affect the binding affinities of the resulted bivalent ligands. In addition, the overall chemical modification of these two pharmacophores for spacer attachment should also be designed from a synthetic point of view, that is, chemical reactions should be readily accomplished. Thus, based on previous successful cases, the C6-position of naltrexone was selected as the attaching locus after transforming its carbonyl group to the 6β-amino group (FIG. 1). Whereas the discovery process of Maraviroc revealed that both of the difluorocyclohexyl moiety and the exo-1,2,4-triazole substituted tropane core are essential to its potent antiviral activity and weak hERG inhibition. Additionally, an interactive docking study of Maraviroc to a rhodopsin-based CCR5 homology model demonstrated the interactions between Glu283 and the tropane core, as well as Ile198 and the difluorocyclohexyl moiety within the proposed binding pocket. Hence, the para-position of the phenyl ring in Maraviroc was first chosen as the linking site to avoid severe impacts to the above interactions. Since EDCI/HOBt mediated coupling reaction between carboxylic acid and amine can be easily accomplished, an amino group was then chosen as the functional group on this para-phenyl ring to hook Maraviroc up with the spacer. Thus, pharmacophore 6 (Scheme 1) was designed as the precursor of the CCR5 antagonist.

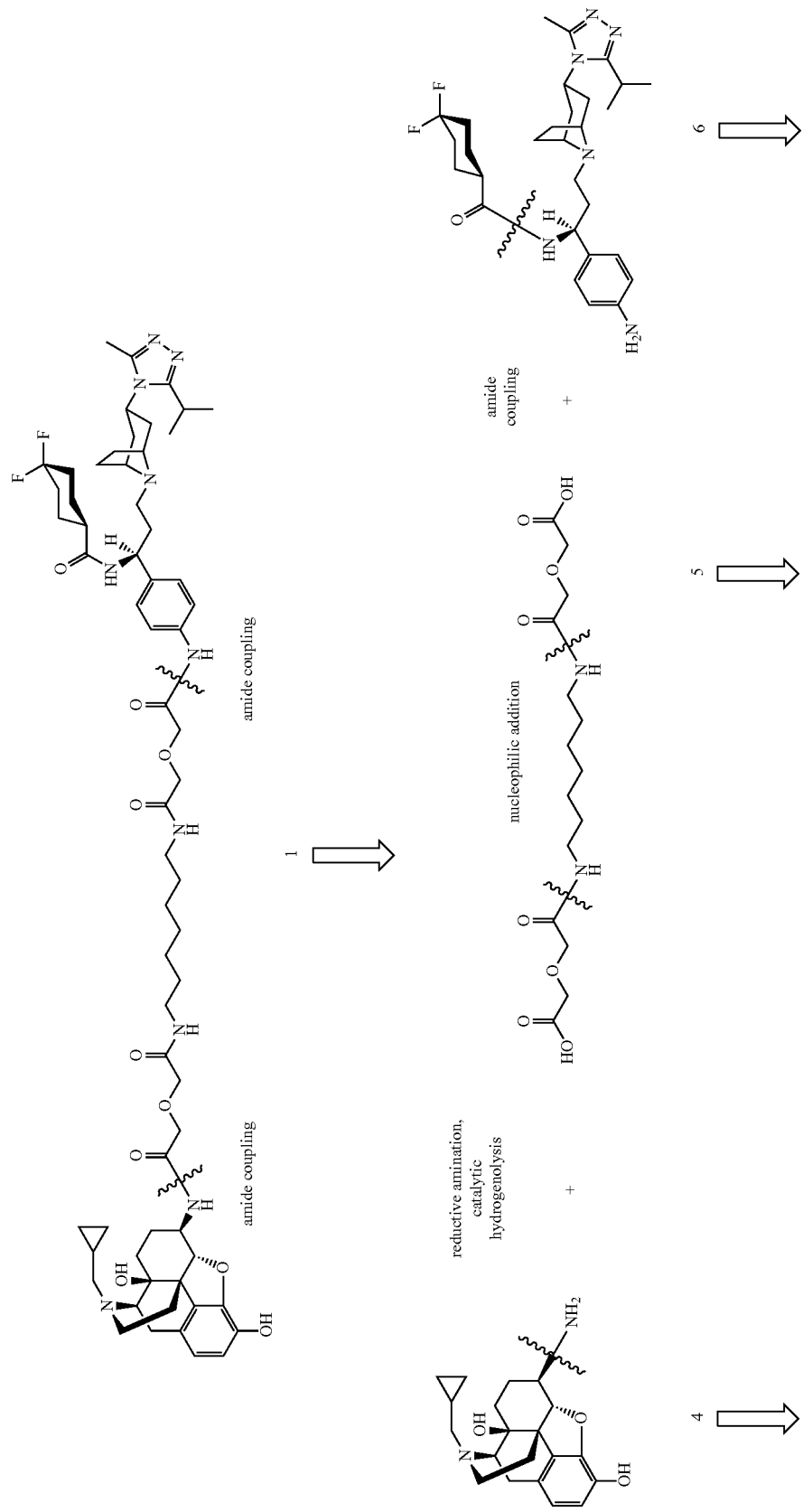

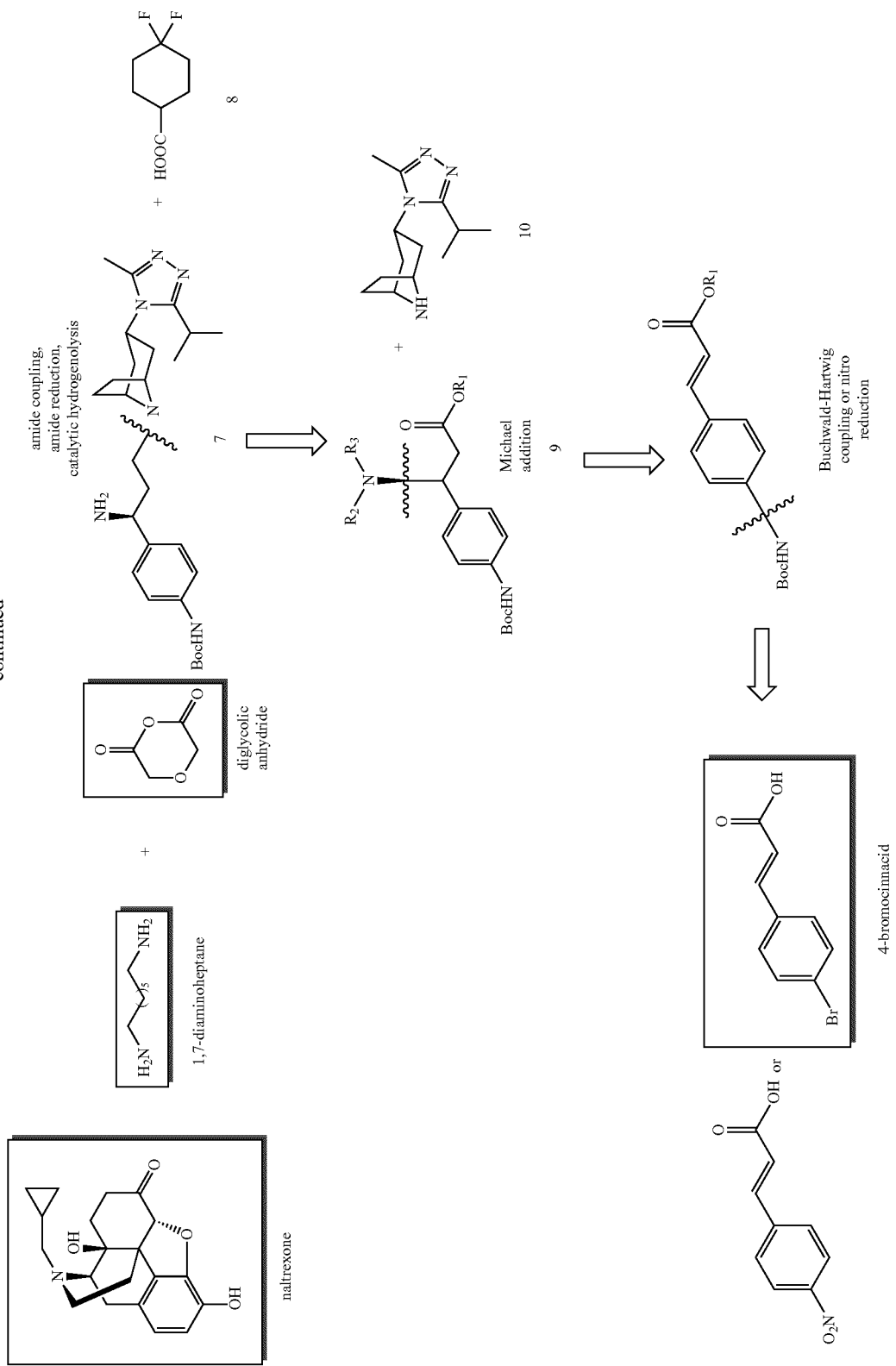

Several studies indicated that a spacer with 16 to 22 atoms might be beneficial for targeting GPCR dimers, ideally with 21 atoms when both pharmacophores are antagonists of their respective receptors. Therefore, the 21-atom-spacer was adopted as an initial lead in the current study. The design rationale of such a spacer is to keep a favorable balance between hydrophobicity and hydrophilicity as well as to possess a reasonable rigidity, high stability and low toxicity. Hence, one alkyldiamine moiety and two diglycolic units were employed to build up the spacer. Monovalent ligands 2 and 3 (FIG. 1) were also designed as controls to clarify the potential effects of the spacer to the binding affinity and potency of the bivalent ligand.

Chemistry and Biological Studies

The retrosynthetic analysis of bivalent ligand 1 revealed three major fragments, 6β-naltrexamine 4, diacid spacer 5, and the CCR5 antagonist precursor 4-NH$_2$-Maraviroc 6 (Scheme 1). Among them, 6β-naltrexamine 4 can be conveniently prepared from naltrexone following the reported procedure, whereas nucleophilic reaction of 1,7-diaminoheptane with diglycolic anhydride can readily afford the diacid spacer 5. Similarly to Maraviroc, retrosynthetic analysis of 6 identified three key fragments: a 4,4-difluorocyclohexanecarboxylic acid 8, a β-phenylalanine ester 9, and a triazole-substituted tropane 10 (Scheme 1). As the preparation of difluoro acid 8 appeared to be challenging, a strategy that enables a later introduction of this fragment was sought. In order to avoid the tedious reduction-oxidation procedure as well as to improve the overall yields, an amide coupling strategy instead of reductive amination was postulated to generate 7 by coupling 9 with 10. Several papers have reported the highly stereoselective introduction of an amino group through Michael addition with lithium (R)—N-benzyl-N-α-methylbenzylamide in high yields. Hence, the same method was adopted to prepare fragment 9. Two cinnamic acids are commercially available to synthesize the substrate 11 for a later Michael addition: 4-nitrocinnacid and 4-bromo-cinnacid. However, the conversion of the nitro group to the amino group poses an issue for the overall synthetic route since other functional groups, such as double bond, ester, benzyl, and amide, are present in the same molecule and reducing agents such as Na$_2$S and SnCl$_2$ are not environment-friendly. Therefore, 4-bromocinnacid was chosen as the starting material.

The overall synthesis of the precursor 6 is illustrated in Schemes 2 and 3. The carboxylic group protection was performed by refluxing 4-bromocinnacid in isopropanol with a few drops of concentrated sulfuric acid to give a moderate yield of 12. The bromide 12 was then converted to aniline 13 using Lithium hexamethyldisilazide (LHMDS) catalyzed by Pd$_2$(dba)$_3$ and P(t-Bu)$_3$, which upon heating with di-tert-butyl dicarbonate furnished compound 14 in a good yield. The diastereoselective Michael addition of 14 was achieved with lithium (R)—N-benzyl-N-α-methylbenzylamide prepared in situ. The stereoselectivity was confirmed by comparing with the literature reported data. The following saponification of the conjugate adduct 15 gave acid 16, which was then coupled with 3-(3-isopropyl-5-methyl-4H-1,2,4-triazol-4-yl)-exo-8-azabicyclo[3.2.1]octane 10 through HOBt/EDCI method to yield 17. The reduction of 17 with either BH$_3$.THF or LiAlH$_4$ at ambient temperature did not give any amide reduced product 18. Heating 17 with BH$_3$-THF resulted a mixture of complexes, with the loss of Boc and/or two benzyl groups. The steric hindrance generated by the two benzyl groups might complicate the reduction process. Hence, the catalytic hydrogenolysis of 17 with 10% Pd/C was conducted to produce intermediate 19 instead. Although reaction of 19 with BH$_3$.THF did afford compound 7, the majority of the product formed a complex with tetrahydrofuran (1:1), which requires acid to release the free amine. However, Boc group may be sensitive to such acidic conditions. Replacement of BH$_3$.THF with LiAlH$_4$, which only needs water to decompose the intermediate formed after the reaction,[47] provided 7 in a reasonable yield (Scheme 2). Reaction of 7 with 4,4-difluorocyclohexanecarboxylic acid 8 was mediated by HOBt/EDCI and the coupling product 20 was subsequently converted to the CCR5 antagonist precursor 6 with TFA/DCM (1:10) at ambient temperature (Scheme 3).

Scheme 2. Synthesis of intermediate 7[a]

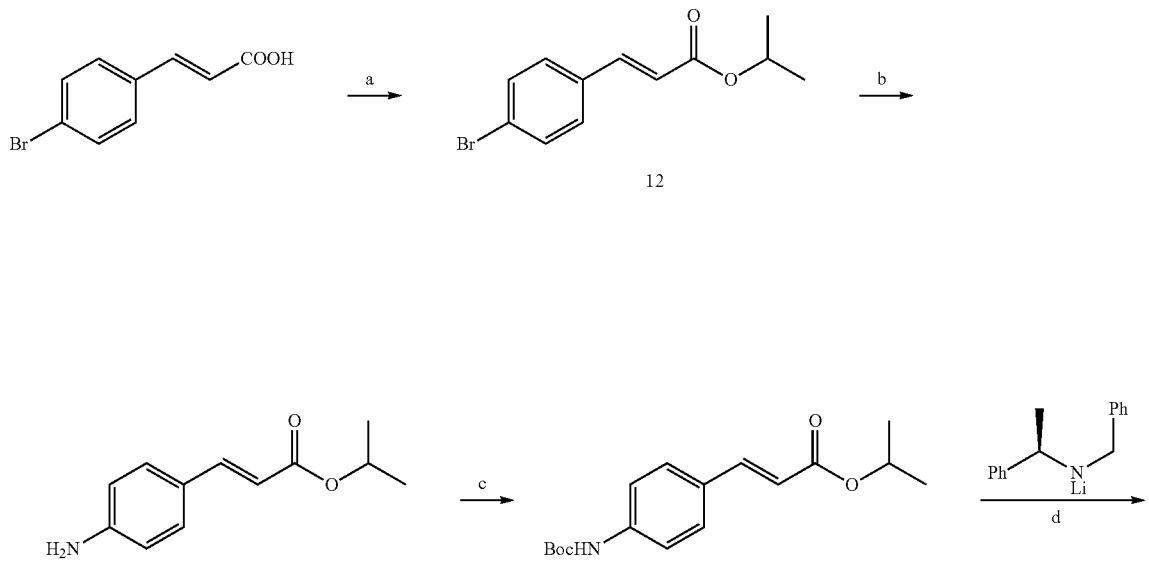

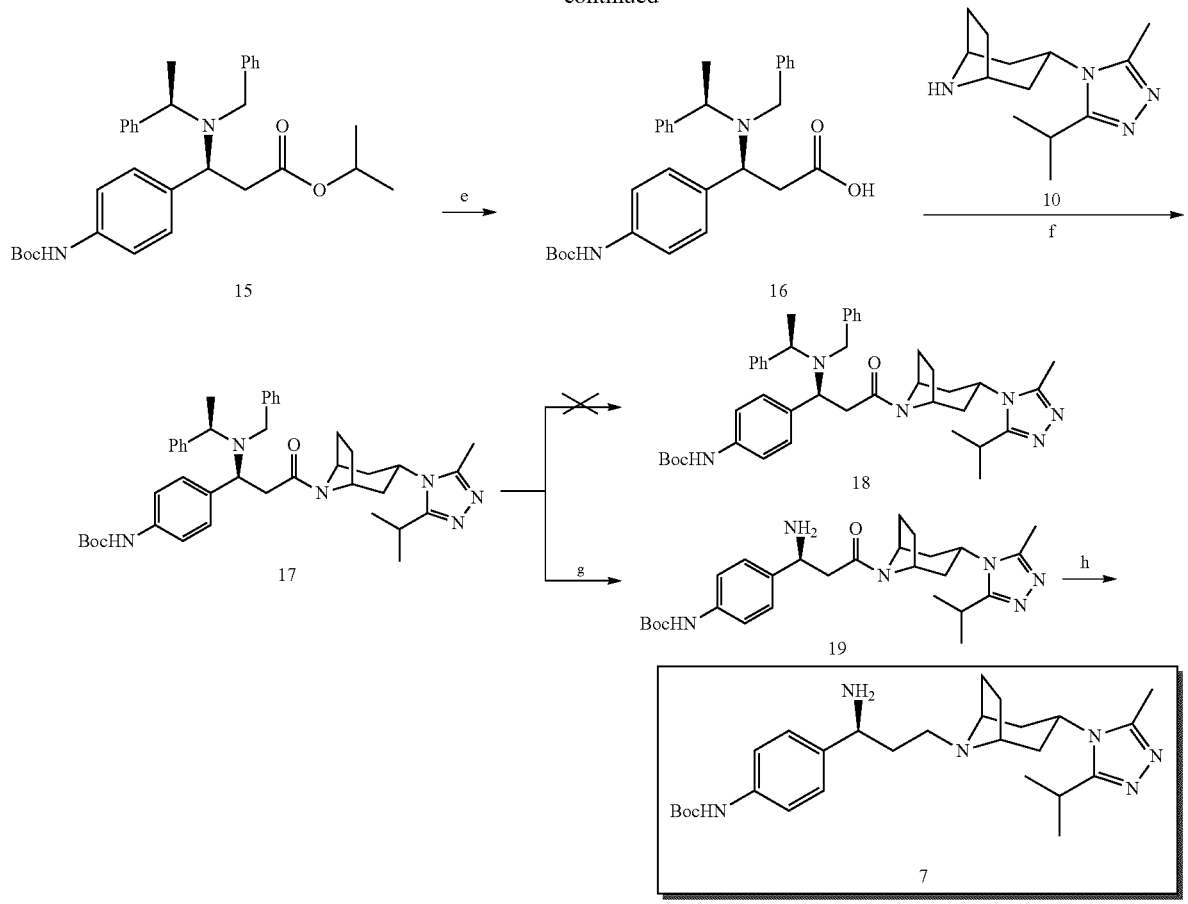

*Regents and conditions: (a) i-PrOH, H₂SO₄ (conc.), reflux, 80%; (b) i) LHMDS, Pd₂(dba)₃, P(t-Bu)₃, Toluene, rt; ii) 1N HCl, rt, 90%; (c) Boc₂O, THF, reflux, 85%; (d) THF, -78° C.; (e) LiOH, MeOH/H₂O (2/1), reflux, 85% two steps; (f) EDCI, HOBt, TEA, 10, 4Å MS, DCM, 0° C. to rt, 73%; (g) 10% Pd/C, 60 psi, MeOH, 84%; (h) i) LiAlH₄, THF, 0° C. to rt; ii) H₂O, NaOH, 71%

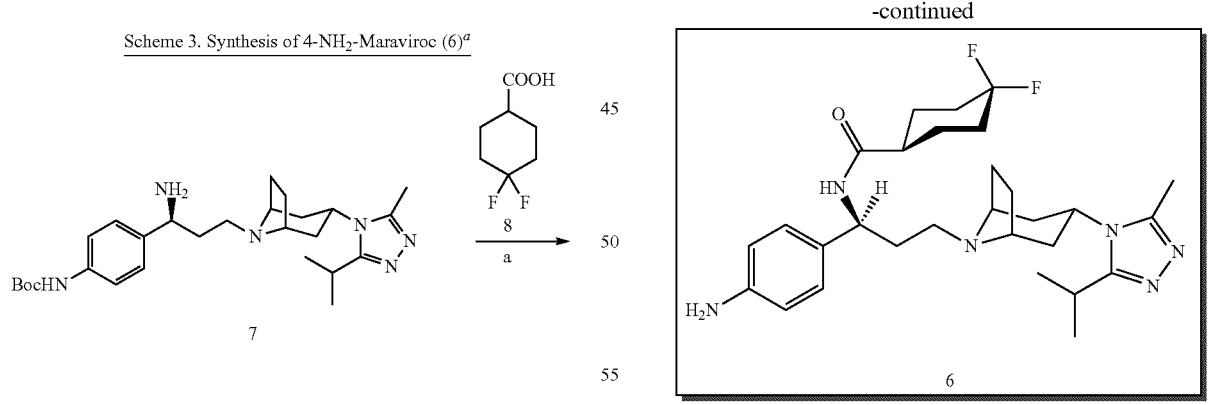

(a) EDCI, HOBt, TEA, 8, 4Å MS, DCM, 0° C. to rt, 85%;
(b) CF₃COOH, DCM, 0° C. to rt, 95%.

Then the bivalent ligand 1 was prepared following a linear synthetic route as shown in Scheme 4. Reaction of 1,7-diaminoheptane with 0.9 equivalent of benzyl chloroformate under ice-water bath generated mono-Cbz protected intermediate 21, which was further condensed with diglycolic anhydride to give compound 22. Intermediate 23 was prepared by coupling 22 with 4 (6β-naltrexamine[39]) utilizing HOBt/EDCI method.

Hydrogenation-deprotection of 23 with 10% Pd/C catalyst yielded amine 24. Condensation of 24 with a second molecule of diglycolic anhydride provided acid 25, which was then coupled with the CCR5 antagonist precursor 6 via HOBt/EDCI mediation to furnish bivalent ligand 1. Monovalent ligand 2 was conveniently synthesized by coupling the intermediate 24 with 26[30b] via HOBt/EDCI peptide coupling method (Scheme 5).

Scheme 4. Synthesis of ligand 1[a]

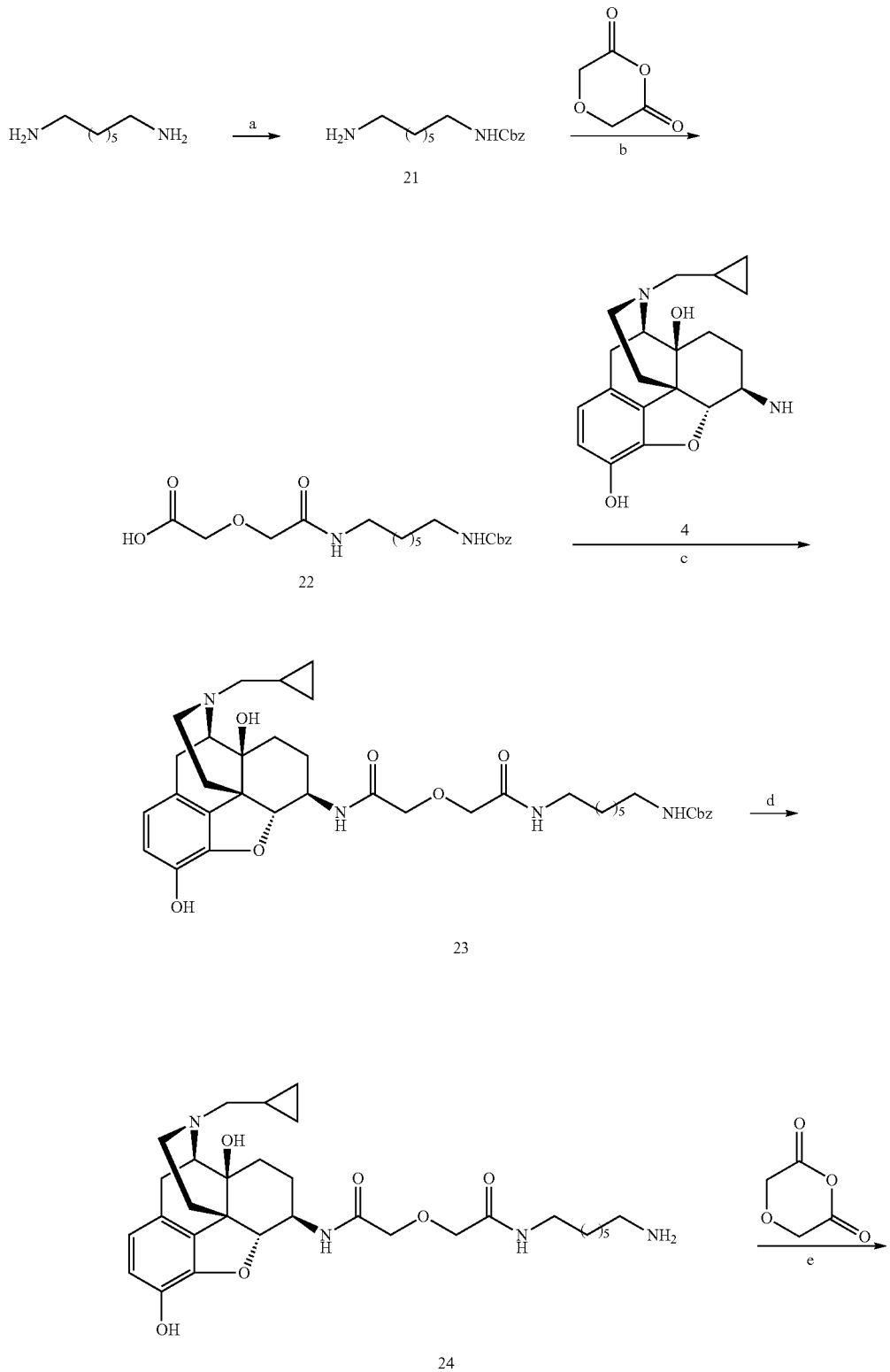

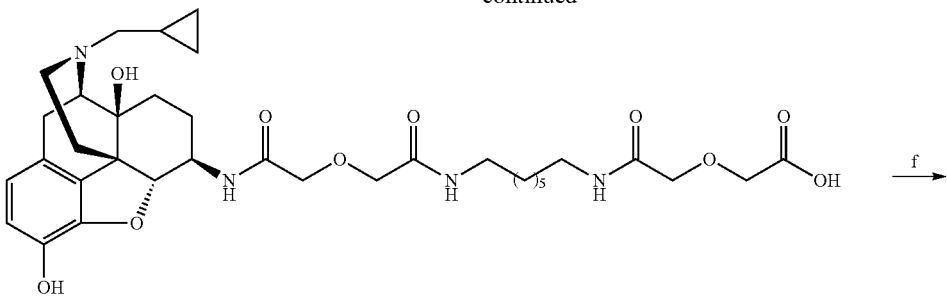

25

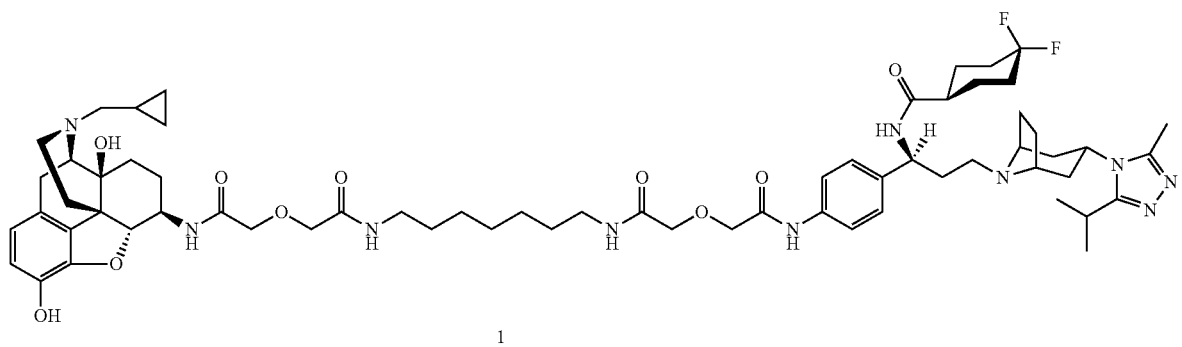

1

<sup>a</sup>Regents and conditions: (a) CbzCl, DCM, MeOH, 5° C., 32%; (b) THF, diglycolic anhydride, rt, 85%; (c) EDCI, HOBt, TEA, 4·2HCl, 4Å MS, DMF, 0° C. to rt, 76%; (d) 10% Pd/C, 60 psi, MeOH, 99%; (e) DMF, diglycolic anhydride, rt, 82%; (f) EDCI, HOBt, TEA, 6, 4Å MS, DMF, 0° C. to rt, 50%.

Scheme 5. Synthesis of monovalent ligand 2<sup>a</sup>

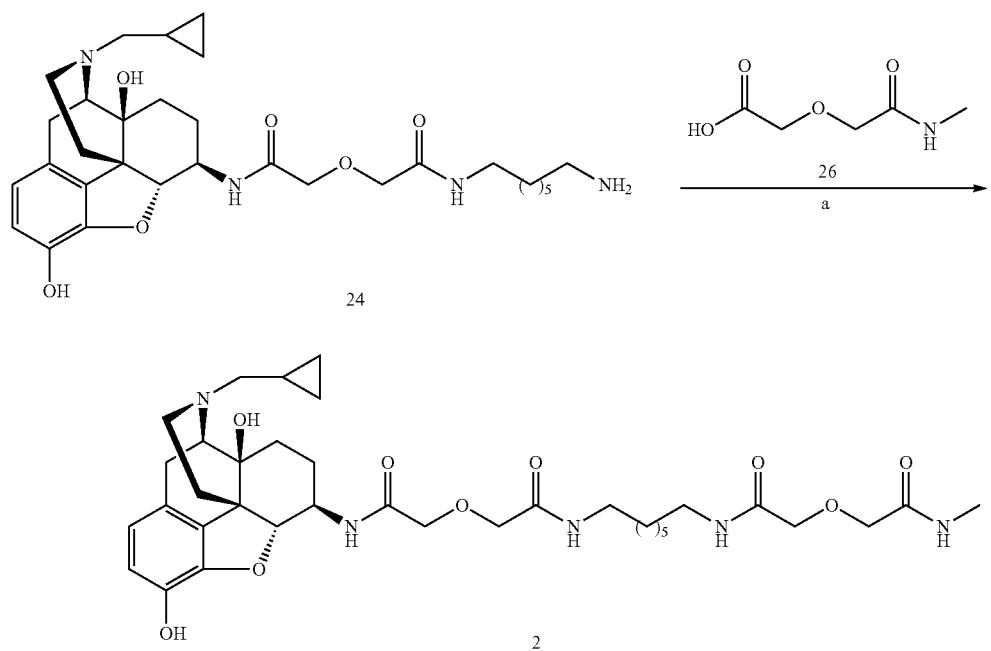

<sup>a</sup>Regents and conditions: (a) EDCI, HOBt, TEA, 26, 4Å MS, DMF, 0° C. to rt, 65%.

From an efficient synthesis perspective, monovalent ligand 3 was prepared according to Scheme 6, considering it only involved three steps and all the reactions can be simply monitored by UV. Thus, HOBt/EDCI-mediated coupling of 22 with precursor 6 afforded intermediate 27, which underwent catalytic hydrogenolysis to yield amine 28. Monovalent ligand 3 was then obtained by coupling 28 with 26 employing HOBt/EDCI method.

Scheme 6. Synthesis of monovalent ligand 3[a]

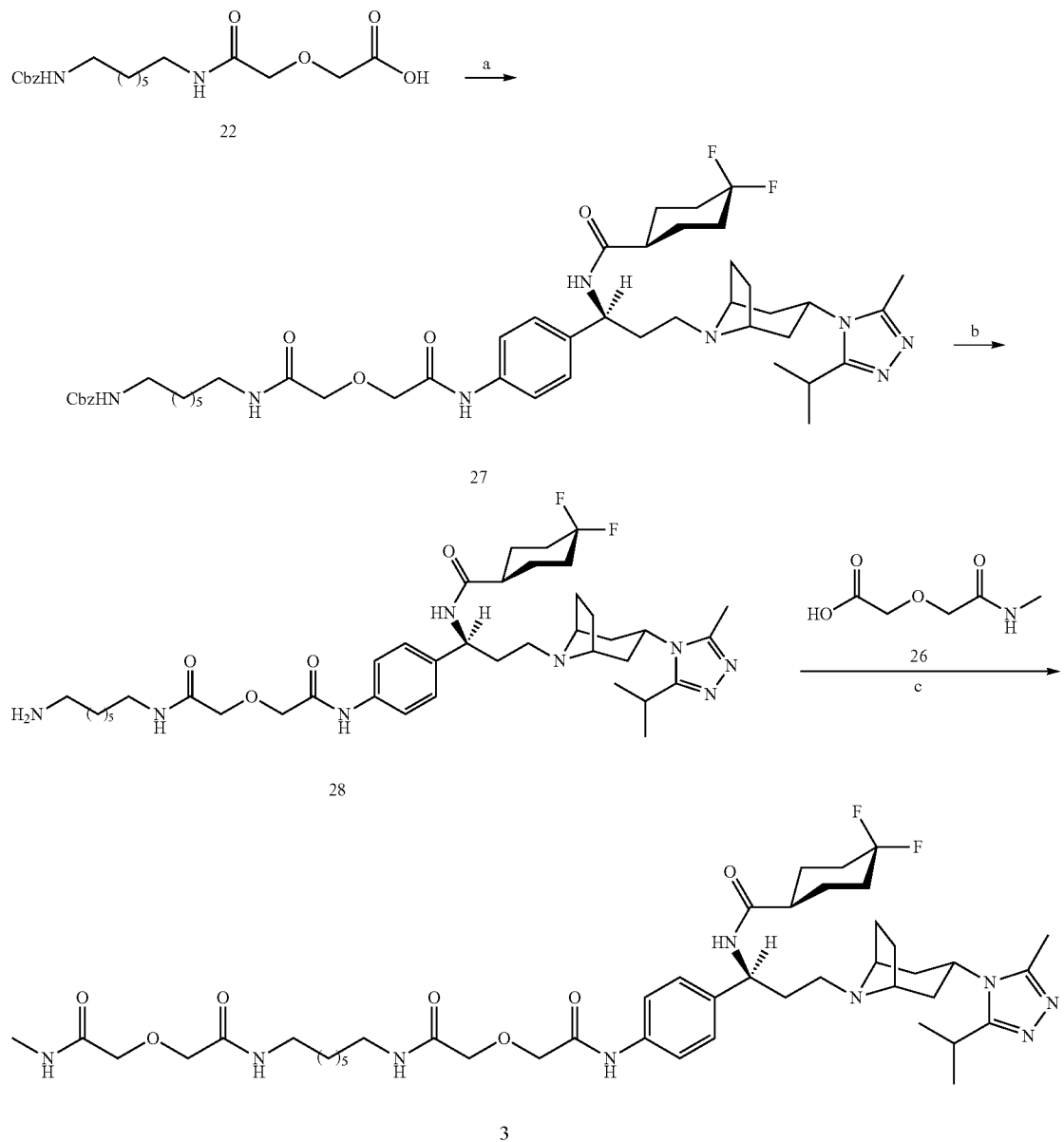

[a]Regents and conditions: (a) EDCI, HOBt, TEA, 6, 4Å MS, DMF, 0° C. to rt, 72%; (b) 5% Pd/C, 60 psi, MeOH, 51%; (c) EDCI, HOBt, TEA, 26, 4Å MS, DMF, 0° C to rt, 81%

All three ligands were then further characterized for their binding affinity and functional activities preliminarily. In a calcium mobilization assay with CCR5/MOLT-4 cells, compound 1 showed no agonism and its antagonist property indicated by its calcium flux inhibition $IC_{50}$ value as 231±88 nM. Compared with the calcium flux inhibition $IC_{50}$ value of Maraviroc under the same experimental condition, which was 1.57±0.32 nM, apparently the introduction of the long chain spacer seemed to be influential to the binding affinity of compound 1 to the receptor CCR5, as indicted by its significant decrement on functional activity of calcium flux inhibition. This was further supported by the even lower functional property of the control compound 3, of which the calcium flux inhibition $IC_{50}$ value was 833±150 nM. A couple of reasons could lead to such results. First, the bulkiness of the spacer might influence the binding affinity to the receptor directly. Second, the substitution position of the spacer on the tailing aromatic ring system of Maraviroc might not be the most suitable one in preventing serious steric hindrance effect on the binding affinity. Currently the syntheses of new ligands with spacer attached at different position of this tailing ring system are underway.

Similarly, in $^{35}$S-GTP[γS] binding assays in MOR—CHO cells, compound 1 showed very little apparent agonism ($E_{max}$=11.7±1.2%) compared to the full agonist DAMGO (100±9.2%, $EC_{50}$=13.7±1.6 nM), while its binding affinity to the mu opioid receptor as indicated by $K_i$ value was 51.8±7.9 nM, which was lower than naltrexone's binding affinity ($K_i$ value was 0.71±0.08 nM) under the same experimental condition. Correspondingly the control compound 2 also showed somewhat lower binding affinity as indicted by the $K_i$ value of 9.18±3.44 nM.

These preliminary biological activity results supported our original molecular design that the bivalent ligand did reserve the original antagonist property from both pharmacophores while its relatively lower affinity to the each corresponding receptor compared to the parent pharmacophores, which was not unusual based on previous reports, certainly requires more extensive structural modification and further syntheses effort.

Conclusions

In conclusion, a bivalent ligand with 21-atom spacer (spacers of 15-25 atoms and most preferably 16-22 atoms are preferred) was designed and synthesized as a molecular probe to study the biological and pharmacological mechanisms of the putative heterodimerization between the mu opioid receptor and the chemokine receptor CCR5. The overall 16-step synthetic route was efficient and convergent with reasonable yields. The biological data from the calcium mobilization assay and MOR—CHO binding assay showed that the bivalent ligand 1 retained the characteristics of its pharmacophores, antagonizing MOR and/or CCR5 respectively.

EXPERIMENTAL

Synthesis
General Methods

All reagents were purchased from Sigma-Aldrich or as otherwise stated. TLC analyses were carried out on Analtech Uniplate F254 plates. Chromatographic purification was accomplished on silica gel columns (230-400 mesh, Merck). Melting points were obtained with a Fisher scientific micro melting point apparatus without further correction. All IR spectra were recorded on a Nicolet iS10 FT-IR Instrument. Proton (400 MHz) and Carbon-13 (100 MHz) nuclear magnetic resonance (NMR) spectra were acquired at ambient temperature with tetramethylsilane as the internal standard on a Bruker Ultrashield 400 Plus spectrometer. MS analysis was performed on an Applied Bio Systems 3200 Q trap with a turbo V source for TurboIonSpray. HPLC analysis of the final compounds was achieved on Varian ProStar 210 system on Microsorb-MV 100-5 C18 column (250 mm×4.6 mm) at 254 (1 & 3) or 210 (2) nm eluting with acetonitrile (0.1% TFA)/water (50/50) at 1 mL/min over 10 min. Elemental analysis of the final compounds was conducted in Atlantic Microlab, Inc.

General Procedure for Amide Coupling

On an ice-water bath, a solution of acid in either DCM or DMF (3 mL), was added EDCI (1.5 eq), HOBt (1.5 eq), molecular sieves, and TEA (4.0 eq) with $N_2$ protection. After 15 min, a solution of amine (1.0 eq) in DMF or DCM (1 mL) was added dropwise. The resulted mixture was allowed to warm up to ambient temperature gradually. After completion of the reaction as monitored by TLC, the reaction mixture was filtered through celite. When DMF was used as the reaction solvent, the filtrate was concentrated in vacuum to remove DMF and the residue was then purified with column chromatography to afford the coupling product, whereas when DCM was the solvent, the filtrate was washed with brine, dried over $Na_2SO_4$, concentrated and the crude product was purified by either crystallization or column chromatography.

Bivalent Ligand 1

The title compound was prepared according to the general amide coupling procedure by reacting acid 25 with amine 6 in DMF for 7 days. The crude product was purified by column chromatography using $CH_2Cl_2$/MeOH (10/1) as eluent to give 87 mg white solid, in 50% yield. $^1$H NMR (400 MHz, $CD_3OD$): δ 7.60 (d, J=8.56 Hz, 2H), 7.33 (d, J=8.56 Hz, 2H), 6.67 (d, J=8.08 Hz, 1H), 6.62 (d, J=8.20 Hz, 1H), 5.03 (t, J=7.38 Hz, 1H), 4.58 (d, J=7.64 Hz, 1H), 4.39 (m, 1H), 4.20 (s, 2H), 4.12 (s, 2H), 4.05 (s, 2H), 4.04 (s, 2H), 3.74 (m, 1H), 3.43 (m, 2H), 3.28-3.23 (m, 5H), 2.90-2.74 (m, 3H), 2.50 (s, 3H), 2.48-2.41 (m, 2H), 2.41-2.32 (m, 2H), 2.30-2.20 (m, 2H), 2.19-2.05 (m, 4H), 2.04-1.69 (m, 15H), 1.68-1.46 (m, 8H), 1.37 (m, 6H), 1.34 (d, J=6.84 Hz, 6H), 0.94 (m, 1H), 0.64-0.58 (m, 2H), 0.29 (m, 2H); $^{13}$C NMR (100 MHz, $CD_3OD$): δ 176.63, 171.70, 171.55, 171.50, 170.10, 161.47, 161.43, 143.77, 143.44, 140.34, 138.06, 137.93, 128.22, 121.89, 120.63, 120.43, 119.03, 92.56, 71.99, 71.79, 71.62, 71.58 (×2), 63.99, 60.76, 60.24, 57.25, 52.46, 52.40, 49.51, 49.30, 44.31, 43.69, 40.06, 38.17, 36.74, 36.08, 35.89, 33.88 ($J^{13}C$-$^{19}F$ 23 Hz), 31.20, 30.34, 30.31, 29.95, 28.03, 27.84, 27.82, 27.29, 27.19, 27.07, 27.00, 26.76, 25.17, 23.91, 22.06, 15.72, 12.45, 3.93. IR v (Diamond, $cm^{-1}$): 3275, 1652, 1532, 1128, 1107. mp 158.5-160° C. Anal. Calcd for $C_{64}H_{92}F_2N_{10}O_{11}$: C, 63.24; H, 7.63; N, 11.52. Found: C, 63.15; H, 7.57; N, 11.28. MS (ESI) found 1198.4 $(M+H)^+$, 1220.5 $(M+Na)^+$.

Monovalent Ligand 2

The title compound was prepared according to the general amide coupling procedure by reacting acid 26 with amine 24 in DMF for 8 h. The crude product was purified with chromatography using $CH_2Cl_2$/MeOH (20/1) as eluent to give 32 mg white solid, in 65% yield. $^1$H NMR (400 MHz, DMSO-$d_6$): δ 9.03 (brs, 1H), 8.22 (d, J=8.44 Hz, 1H), 8.04-7.96 (m, 3H), 6.59 (d, J=8.08 Hz, 1H), 6.53 (d, J=8.12 Hz, 1H), 4.90 (brs, 1H), 4.60 (d, J=7.80 Hz, 1H), 3.95 (s, 2H), 3.94 (s, 2H), 3.91 (m, 4H), 3.57-3.48 (m, 1H), 3.19-3.09 (m, 4H), 3.01-2.99 (m, 2H), 2.66 (d, J=4.68 Hz, 3H), 2.63-8 (m, 2H), 2.40-2.29 (m, 2H), 2.32-2.09 (m, 1H), 1.99 (dt, J=3.43 Hz, $J_2$=11.92 Hz, 1H), 1.84-1.75 (m, 1H), 1.48-1.42 (m, 6H), 1.33-4 (m, 8H), 0.86 (m, 1H), 0.48 (m, 2H), 0.13 (m, 2H); $^1$H NMR (400 MHz, $CD_3OD$): δ 6.67 (d, J=8.12 Hz, 1H), 6.60 (d, J=8.12 Hz, 1H), 4.56 (d, J=7.56 Hz, 1H), 4.10 (s, 2H), 4.09 (s, 2H), 4.08 (s, 2H), 4.06 (s, 2H), 3.82-8 (m, 1H), 3.30 (q, J=7.34 Hz, 4H), 3.18-3.13 (m, 2H), 2.82 (s, 3H), 2.73-2.64 (m, 2H), 2.48-2.40 (m, 2H), 2.32-2.25 (m, 1H), 2.18 (dt, J=3.04 Hz, 11.81 Hz, 1H), 1.94 (m, 1H), 1.60-1.58 (m, 6H), 1.48-1.32 (m, 8H), 0.95 (m, 1H), 0.56 (On, 2H), 0.19 (m, 2H); $^{13}$C NMR (100 MHz, $CD_3OD$): δ 172.10, 171.51, 171.43, 171.38, 143.71, 141.88, 132.49, 125.45, 120.06, 118.55, 92.89, 71.68, 71.57, 71.53, 71.45, 71.41, 63.72, 60.27, 52.45, 48.88, 45.38, 45.24, 40.02, 31.98, 31.22, 30.35, 29.99, 27.84, 25.87, 25.46, 23.52, 10.29, 4.45, 4.21. IR v (Diamond, $cm^{-1}$): 3291, 1652, 1544, 1124. mp 74-76° C. Anal. Calad for $C_{36}H_{55}N_5O_{10}$: C, 60.23; H, 7.72; N, 9.76. Found: C, 60.22; H, 7.74; N, 9.57. MS (ESI) ml. found 701.0 $(M+H)^+$, 722.9 $(M+Na)^+$.

Monovalent Ligand 3

The title compound was prepared according to the general amide coupling procedure by reacting acid 26 with amine 28 in DMF overnight. The crude product was purified with chromatography using $CH_2Cl_2$/MeOH (8/1) as eluent to give 106 mg white solid, in 81% yield. $^1$H NMR (400 MHz, $CD_3OD$): δ 7.60 (d, J=8.52 Hz, 2H), 7.33 (d, J=8.56 Hz, 2H), 5.03 (t, J=7.32 Hz, 1H), 4.44-4.35 (m, 1H), 4.20 (s, 2H), 4.12 (s, 2H), 4.02 (m, 4H), 3.42 (m, 2H), 3.30-3.20 (m, 5H), 2.78 (s, 3H), 2.50 (s, 3H), 2.47-0 (m, 2H), 2.39-2.30 (m, 1H), 2.30-2.17 (m, 2H), 2.15-2.03 (m, 4H), 2.02-5 (m, 2H), 1.90-1.65 (m, 10H), 1.60-5 (m, 4H), 1.40-1.30 (m, 12H); $^{13}$C NMR (100 MHz, CD$_3$OD): δ 176.61, 172.13, 171.68, 171.46, 170.08, 161.42, 152.61, 140.33, 138.08, 128.22, 121.89, 71.97, 71.77, 71.48, 71.44, 60.71, 60.22, 52.40, 44.55, 43.70, 40.07, 40.03, 36.75, 36.10, 33.86 (J $^{13}$C-$^{19}$F 23 Hz), 30.38, 30.35, 29.99, 27.86, 27.20 (J$^{13}$C-$^{19}$F 9 Hz), 27.07, 27.02, 26.98, 26.76, 25.89, 22.06, 12.44. IR v (Diamond, cm$^{-1}$): 3272, 1652, 1532, 1107. mp 79-81° C. Anal. Calcd for C$_{45}$H$_{73}$F$_2$N$_9$O$_9$: C, 58.61; H, 7.98; N, 13.67. Found: C, 59.29; H, 7.96; N, 13.47. MS (ESI) m/z found 887.2 (M+H)$^+$, 909.3 (M+Na)$^+$.

6'β-Naltrexamine Hydrochloride Salt (4.2HCl)

The title compound was prepared following the reported procedure[39] in 62% yield for two steps (lit., [39] 71%). NMR (400 MHz, DMSO-d$_6$): δ 9.58 (s, 1H, exchangeable), 8.91 (brs, 1H, exchangeable), 8.43 (m, 3H, exchangeable), 6.80 (d, J=8.0 Hz, 1H), 6.67 (d, J=8.0 Hz, 1H), 6.40 (brs, 1H), 4.68 (d, J=7.2 Hz, 1H), 3.90 (d, J=4.8 Hz, 1H), 3.33 (m, 2H), 3.04 (dd, J=6.0 Hz, J$_2$=18.8 Hz, 2H), 2.90-2.70 (m, 2H), 2.50-2.40 (m, 2H), 1.99 (q, J=12.5 Hz, 1H), 1.82 (d, J=14.4 Hz, 1H), 1.78-0 (m, 1H), 1.46 (d, J=8.8 Hz, 1H), 1.32 (m, 1H), 1.06 (m, 1H), 0.67 (m, 1H), 0.59 (m, 1H), 0.51 (m, 1H), 0.41 (m, 1H).

5,15-Dioxo-3,17-dioxa-diazanonadecane-1,19-dioic acid (5)

To the solution of 1,7-diaminoheptane (1.3 g, 10 mmol) in THF (4 mL) at 0° C. was added diglycolic anhydride (2.44 g, 21 mmol) in one portion. The resultant mixture was stirred at the same temperature for 15 min and allowed to warm to ambient temperature and stirred overnight. After removed THF under reduced pressure, the residue was crystallized by EtOAc/hexane to give 3.470 g white solid as first crop, in 96% yield. $^1$H NMR (400 MHz, DMSO-d$_6$): δ12.78 (brs, 2H), 7.81 (t, J=5.70 Hz, 2H), 4.10 (s, 4H), 3.94 (s, 4H), 3.08 (q, J=6.76 Hz, 4H), 1.41 (m, 4H), 1.25 (m, 6H). $^{13}$C NMR (100 MHz, CD$_3$OD): δ 171.47, 168.60, 70.12, 67.85, 38.07, 28.98, 28.36, 26.24. IR v (Diamond, cm$^{-1}$): 3306, 1699, 1646, 1548, 1247, 1151, 1136, 711. mp 64-67° C. MS (ESI) m/z found 363.5 (M+H)$^+$.

4,4-Difluoro-cyclohexanecarboxylic acid {1-(4-amino-phenyl)-3-[3-(3-isopropyl-5-methyl-[1,2,4] triazol-4-yl)-8-aza-bicyclo[3,2,1]oct-8-yl]-propyl}-amide (6)

On ice-water bath, to the solution of 20 (165 mg, 0.262 mmol) in DCM (5 mL) was added TFA (0.5 mL) dropwise. The resultant mixture was allowed to warm to ambient temperature within 15 min and stirred at the same temperature for 1.5 h. The mixture was cooled to 0° C., and saturated Na$_2$CO$_3$ was added. The aqueous layer was adjusted to pH=12, and taken up with DCM (20 mL×3). The combined organic layers were washed with brine, dried over Na$_3$SO$_4$, evaporated and dried in vacuum to afford 131 mg white solid, which is pure enough for the next step, in 95% yield. $^1$H NMR (400 MHz, CDCl$_3$): δ 7.05 (d, J=8.28 Hz, 2H), 6.62 (d, J=8.24 Hz, 2H), 6.38 (brs, 1H), 4.98 (q, J=7.17 Hz, 1H), 4.27 (m, 1H), 3.36 (m, 2H), 2.78 (seq, J=6.84 Hz, 1H), 2.48 (s, 3H), 2.39 (m, 2H), 2.26-2.02 (m, 8H), 1.94-1.73 (m, 6H), 1.70-1.50 (m, 5H), 1.36 (d, J=6.72 Hz, 6H); $^{13}$C NMR (100 MHz, CDCl$_3$): δ 173.28, 159.23, 150.75, 145.98, 131.65, 127.67, 122.74 (J $^{13}$C-$^{19}$F 239 Hz), 115.34, 58.98, 58.42, 51.59, 48.16, 47.38, 42.95, 35.59, 35.50, 34.84, 32.91 (J $^{13}$C-$^{19}$F 24 Hz), 26.84, 26.78, 26.06 (J $^{13}$C$^{19}$F 9.7 Hz), 25.93, 21.75, 13.21. mp 109-110° C. IR v (Diamond, cm$^{-1}$): 3334, 3230, 1636, 1517, 1105, 1031, 962, 831. MS (ESI) m/z found 529.6 (M+H)$^+$.

(4-{1-Amino-3-[3-(3-isopropyl-5-methyl-[1,2,4]-triazol-4-yl)-8-aza-bicyclo[3,2,1]oct-8-yl]-propyl}-phenyl)-carbamic acid tort-butyl ester (7)

On ice-water bath, a solution of 19 (764 mg, 1.538 mmol) in dry THF (10 mL) was added dropwise to a suspension of LiAlH$_4$ (292 mg, 7.692 mmol) in dry THF (10 mL). The resultant mixture was stirred at the same temperature for 15 min and then 3 h at ambient temperature. The mixture was cooled in an ice bath again, and the complex was decomposed by dropwise addition of 2.4 mL H$_2$O, 2.4 mL 4 N NaOH, and 4.8 mL H$_2$O cautiously. The resulting white suspension was continued to stir for 1 h at ambient temperature, then filtered. The filtrate cake was washed with THF (20 mL×3), diethyl ether (20 mL×3). The combined filtrates were concentrated under reduced pressure and the residue was purified by silica gel using DCM/MeOH (6/1) to give 523 mg white solid, in 71% yield. $^1$H NMR (400 MHz, CD$_3$OD): δ7.39 (d, J=8.52 Hz, 2H), 7.28 (d, J=8.60 Hz, 2H), 4.38 (m, 1H), 3.95 (t, J=6.90 Hz, 1H), 3.42 (m, 2H), 3.25 (seq, J=5.83 Hz, 1H), 2.45 (s, 3H), 2.43 (m, 1H), 2.42-2.32 (m, 1H), 2.24-2.15 (m, 2H), 2.05-1.96 (m, 3H), 1.94-1.81 (m, 1H), 1.73 (m, 4H), 1.51 (s, 9H), 1.33 (d, J=6.84 Hz, 6H). $^{13}$C NMR (100 MHz, CD$_3$OD): δ 161.38, 155.32, 152.56, 140.28, 139.81, 128.02, 120.01, 80.86, 60.17, 60.07, 55.62, 49.97, 38.02, 36.37, 36.30, 28.76, 27.13, 26.98, 26.76, 22.05, 12.39. mp 103-105° C. IR v (Diamond, cm$^{-1}$): 3252, 1713, 1522, 1240, 1159, 838. MS (ESI) m/z found 483.7 (M+H.

4,4-Difluoro-cyclohexanecarboxlic acid (8)

The title compound was prepared as described by Mackenzie et al[48], except that the ester was purified by silica gel using EtOAc/hexane (80/1) as eluent. The total yield is 52%. $^1$H NMR (400 MHz, CDCl$_3$): δ 2.48 (m, 1H), 2.16-2.09 (m, 2H), 2.06-2.02 (m, 2H), 1.94-1.83 (m, 4H). $^1$H NMR (400 MHz, CDCl$_3$): δ −94.45-95.09 (d, 1F), −99.19-99.80 (d, 1F). mp 98.5-99.5° C. (lit., [48] 105.9° C.).

3-(3-Isopropyl-5-methyl-[1,2,4]-triazol-4-yl)-exo-8-aza-bicyclo[3.2.1]octane (10)

The title compound and its precursors were synthesized following the same procedure by Haycock-Lewandowski et al.[41a]. The crude product (free base) was crystallized from hexane to give 1.2 g 10, in 97% yield. $^1$H NMR (400 MHz, CDCl$_3$): δ 4.33 (seq, J=6.01 Hz, 1H), 3.74 (m, 2H), 3.02 (seq, J=6.86 Hz, 1H), 2.53 (s, 3H), 2.18 (dt, J$_1$=12.6 Hz, J$_2$=2.66 Hz, 2H), 1.94 (m, 2H), 1.76 (m, 4H), 1.39 (d, J=6.88 Hz, 6H). mp 190-191° C.

3-(4-Bromo-phenyl)-acrylic acid isopropyl ester (12)

To the solution of 4-bromocinnacid (1.135 g, 5 mmol) in isopropanol (50 mL) was added several drops of concentrated sulfuric acid. The mixture was heated to reflux for 48 hours. After cooled down, the residue was worked up with ethyl acetate. The ethyl acetate layer was washed with sat. NaHCO$_3$ aqueous solution, dried over Na$_2$SO$_4$. After filtration and concentration, the resulting crude product was purified by silica column using hexane and ethyl acetate (from 100:1 to 75:1 then 50:1) as eluent to give 1.08 g white solid, in 80% yield. $^1$H NMR (400 MHz, CDCl$_3$): δ 7.59 (d, J=16.0 Hz, 1H), 7.51 (d, J=8.48 Hz, 2H), 7.38 (d, J=8.44 Hz, 2H), 6.40 (d, J=16.0 Hz, 1H), 5.14 (seq, J=6.26 Hz, 1H), 1.31 (d, J=6.24 Hz, 6H); $^{13}$C NMR (100 MHz, CDCl$_3$): δ 166.38, 143.04, 133.63, 132.26, 129.53, 124.51, 119.70, 68.14, 22.07. mp 64-66° C. IR v (Diamond, cm$^{-1}$): 1703, 1637, 1304, 1172, 1104, 981, 817. MS (ESI) m/z found 268.9 (M+H)$^+$, 271.1 (M+2+H)$^+$.

3-(4-Amino-phenyl)-acrylic acid isopropyl ester (13)

The mixture of 12 (1.53 g, 5.68 mmol), Pd$_2$(dba)$_3$ (260 mg, 5% mmol), P(t-Bu)$_3$ (0.23 mL, 1 M in toluene, 4% mmol) in dry toluene (30 mL) was stirred under N$_2$ protection for 15 min. Then a solution of LHMDS in toluene (6.2 mL, 1 M in toluene, 6.2 mmol) was added dropwise. After stirred at ambient temperature overnight, the resultant dark color suspension was added 1 N hydrochloric acid (8 mL) slowly. The resulting mixture was stirred at ambient temperature for 2 hours. Then the suspension was filtered through celite and the filtrate was diluted with dichloromethane (70 mL). The organic layer was washed with saturated NaHCO$_3$ aqueous solution, brine, and dried over Na$_2$SO$_4$. After filtered and concentrated, the crude product was purified by silica gel column using hexane and ethyl acetate (2:1) as eluent to give 1.03 g light yellow solid, in 90% yield. $^1$H NMR (400 MHz, CDCl$_3$): δ 7.58 (d, J=15.9 Hz, 1H), 7.35 (d, J=8.48 Hz, 2H), 6.65 (d, J=8.56 Hz, 2H), 6.22 (d, J=15.9 Hz, 1H), 5.12 (seq, J=6.24 Hz, 1H), 3.91 (brs, 2H), 1.30 (d, J=6.24 Hz, 6H); $^{13}$C NMR (100 MHz, CDCl$_3$): δ 167.20, 148.56, 144.55, 129.80, 124.88, 114.84, 114.35, 67.32, 22.00. mp 78-80° C. IR v (Diamond, cm$^{-1}$): 3417, 3335, 1673, 1592, 1513, 1264, 1168, 1104, 980, 823. MS (ESI) m/z found 206.2 (M+H)$^+$.

3-(4-tort-Butoxycarbonylamino-phenyl)-acrylic acid isopropyl ester (14)

The solution of 13 (1.351 g, 6.58 mmol) and Boc$_2$O (1.58 g, 7.24 mmol) in dry tetrahydrofuran (30 mL) was heated to reflux overnight. After cooled down and concentrated, the residue was crystallized from DCM/hexane to give 1.711 g white solid, in 85% yield. $^1$H NMR (400 MHz, CDCl$_3$): δ 7.60 (d, J=16.0 Hz, 1H), 7.46 (d, J=8.68 Hz, 2H), 7.38 (d, J=8.64 Hz, 2H), 6.55 (brs, 1H), 6.32 (d, J=16.0 Hz, 1H), 5.13 (seq, J=6.25 Hz, 1H), 1.52 (s, 9H), 1.30 (d, J=6.24 Hz, 6H); $^{13}$C NMR (100 MHz, CDCl$_3$): δ 166.77, 152.41, 143.81, 140.30, 129.17, 129.00, 118.33, 117.03, 80.95, 67.63, 28.29, 21.95. mp 159-159.5° C. IR v (Diamond, cm$^{-1}$): 3307, 1725, 1688, 1586, 1521, 1150, 1106, 981, 830. MS (ESI) m/z found 306.2 (M+H)$^+$.

3-[Benzyl-(1-phenyl-ethyl)-amino-3-(4-tert-butoxycarbonylamino-phenyl)-propionic acid isopropyl ester (15)

On ice-water bath, under N$_2$ protection, the solution of R-(+)-N-benzyl-α-methylbenzylamine (1.88 mL, 9.02 mmol) in dry THF was added n-butyllithium (3.47 mL, 2.5 M in hexane) dropwise. The resulting purple solution was stirred for 30 minutes, then cooled down to −78° C., the solution of 14 (1.06 g, 3.47 mmol) in dry THF was added dropwise. Then the dark red solution was stirred for 2 hours at −78° C. Saturated ammonium chloride aqueous was added to quench the reaction. The resultant yellow solution was allowed to warm to ambient temperature within 30 min. After worked up with ethyl acetate, the organic layer was dried, concentrated. The residue was crystallized with ethyl acetate to give 20 mg 15 as colorless crystal. The filtrate was then concentrated and dried on vacuum. Purification of the crude compound by silica gel column chromatography gave mixtures of the excess R-(+)-N-benzyl-α-methylbenzylamine and the product. Hence, the following procedure was performed to transfer the excess amine to the amide to facilitate the purification process. Benzyl chloride (644 μL, 5.55 mmol) was added dropwise into a mixture of the above filtrate and triethylamine (1.543 mL, 11.1 mmol) in 30 mL CH$_2$Cl$_2$ at 0° C. After stirred for 2 hours, the reaction mixture was washed with brine. The organic layer, containing the product 15 and N-benzyl-N-(1-phenyl-ethyl)-benzamide, was dried, concentrated and used for next step without further purification. $^1$H NMR (400 MHz, CDCl$_3$): δ7.40 (d, J=7.2 Hz, 2H), 7.35-7.15 (m, 12H), 6.43 (brs, 1H), 4.79 (seq. J=6.25 Hz, 1H), 4.38 (dd, J=5.2 Hz, J$_2$=9.66 Hz, 1H), 3.97 (q, J=6.75 Hz, 1H), 3.66 (s, 2H), 2.56 (dd, J$_1$=5.12 Hz, J$_2$=14.68 Hz, 1H), 2.50 (dd, J$_1$=14.58 Hz, J$_2$=9.82 Hz, 1H), 1.51 (s, 9H), 1.25 (d, J=6.76 Hz, 3H), 1.05 (d, J=6.24 Hz, 3H), 1.00 (d, J=6.20 Hz, 3H); $^{13}$C NMR (100 MHz, CDCl$_3$): δ 171.36, 152.77, 144.15, 141.63, 137.37, 136.34, 128.75, 128.13 (×2), 128.00, 127.84, 126.83, 126.55, 118.16, 80.47, 67.51, 59.06, 57.05, 50.82, 37.71, 28.37, 21.62, 16.46. mp 172-174° C. IR v (Diamond, cm$^{-1}$): 1724, 1595, 1522, 1154, 1105, 1051, 697. MS (ESI) m/z found 517.5 (M+H)$^+$.

3-[Benzyl-(1-phenyl-ethyl)-amino-3-(4-tert-butoxycarbonylamino-phenyl)-propionic acid (16)

To the above mixture of crude product 15 and N-benzyl-N-(1-phenyl-ethyl)-benzamide in methanol (30 mL) and water (15 mL) was added lithium hydroxide (831 mg, 34.7 mmol). The resulting suspension was heated to reflux for 48 hours. After cooled downed, the mixture was concentrated to remove methanol. The water layer was taken up with CH$_2$Cl$_2$ (30 mL×3). The organic layer was dried and concentrated. The residue was purified by silica gel column using hexane and ethyl acetate (2:1) as eluent to give 1.406 g white solid, in 85% yield for two steps. $^1$H NMR (400 MHz, CDCl$_3$): δ7.44 (d, J=8.52 Hz, 2H), 7.37-7.22 (m, 12H), 6.55 (brs, 1H), 4.43 (dd, J$_1$=4.46 Hz, J$_2$=11.32 Hz, 1H), 4.15 (q, J=6.87 Hz, 1H), 3.98 (d, J=13.68 Hz, 1H), 3.64 (d, J=13.68 Hz, 1H), 2.92 (dd, J$_1$=11.34 Hz, J$_2$=16.94 Hz, 1H), 2.41 (dd, J$_1$=4.48 Hz, J$_2$=16.96 Hz, 1H), 1.54 (s, 9H), 1.28 (d, J=6.88 Hz, 3H); $^{13}$C NMR (100 MHz, CDCl$_3$): 174.39, 152.82, 141.25, 138.44, 137.70, 132.56, 129.22, 128.80, 128.62, 128.60, 128.19, 127.81, 127.53, 118.52, 80.86, 57.96, 57.82, 50.61, 36.29, 28.34, 15.68. mp 93-95° C. IR v (Diamond, cm$^{-1}$): 3307, 1699, 1594, 1081, 698. MS (ESI) m/z found 475.6 (M+H)$^+$.

(4-{1-[Benzyl-(1-phenyl-ethyl)-amino]-3-[3-(3-isopropyl-5-methyl-[1,2,4]-triazol-4-yl)-8-aza-bicyclo [3,2,1]oct-8-yl]-3-oxo-propyl}-phenyl)-carbamic acid tort-butyl ester (17)

The title compound was prepared according to the general amide coupling procedure by reacting acid 16 with amine 10 in DCM for 4 h. The crude product was crystallized using DCM/hexane to give 986 mg white solid as first crop, in 73% yield. $^1$H NMR (400 MHz, CDCl$_3$): δ 7.88 (d, J=8.32 Hz, 1H), 7.68 (d, J=8.28 Hz, 1H), 7.46 (d, J=7.60 Hz, 2H), 7.41-7.35 (m, 10H), 7.33-7.12 (m, 14H), 6.91 (brs, 1H), 6.66 (brs, 1H), 4.68 (m, 1H), 4.62 (m, 1H), 4.53 (dd, J=5.54 Hz, J$_2$=8.10 Hz, 1H), 4.40-4.28 (m, 3H), 4.03-3.96 (m, 2H), 3.82-2 (m, 6H), 2.76 (m, 2H), 2.54 (m, 4H), 2.21 (s, 3H), 2.11 (s, 3H), 2.06-1.96 (m, 4H), 1.96-1.55 (m, 12H), 1.51 (s, 9H), 1.50 (s, 9H), 1.30 (m, 12H), 1.28-1.24 (m, 6H); $^{13}$C NMR (100 MHz, CDCl$_3$): δ 167.31, 166.99, 158.87, 152.80, 150.35, 144.43, 142.17 (142.05), 137.78, 136.61, 136.32, 80.46, 61.06, 59.34, 56.53 (56.40), 53.82 (53.43), 51.11 (50.80), 50.56 (50.49), 46.67, 38.87 (38.27), 37.60 (37.46), 35.67, 28.34, 26.86 (26.61), 25.79, 21.63 (21.56), 14.59, 13.80, 12.99. mp 128-130° C. IR v (Diamond, cm$^{-1}$): 2966, 1721, 1637, 1545, 1436, 1242, 1165, 742, 705. MS (ESI) m/z found 691.5 (M+H)$^+$.

(4-{1-Amino-3-[3-(3-isopropyl-5-methyl-[1,2,4]triazol-4-yl)-8-aza-bicyclo[3,2,1]oct-8-yl]-3-oxyl}-phenyl)-carbamic acid tert-butyl ester (19)

A solution of 17 (500 mg, 0.725 mmol) in methanol (35 mL) was treated with palladium carbon (100 mg, 10 wt %), and the resultant slurry was shaken under an atmosphere of hydrogen at 60 psi for 4 days at ambient temperature. The reaction mixture was filtered through celite. The filtrate cake was washed with methanol and the combined filtrates were concentrated and purified by silica gel using DCM/MeOH (20/1) as eluent to give 304 mg white solid 19, in 84% yield. $^1$H NMR (400 MHz, CDCl$_3$): δ 7.34 (d, J=5.88 Hz, 8H), 6.46 (brs, 2H), 4.88 (m, 2H), 4.57-4.47 (m, 4H), 4.34-1.23 (m, 2H), 2.93 (seq, J=7.03 Hz, 2H), 2.73-0 (m, 4H), 2.46 (s, 3H), 2.36 (s, 3H), 2.33-5 (m, 8H), 1.85-1.71 (m, 8H), 1.52 (s, 18H), 1.40-1.37 (m, 12H); $^{13}$C NMR (100 MHz, CDCl$_3$): δ 167.71 (167.41), 158.99 (158.93), 152.86, 150.51 (150.38), 139.43, 137.83 (137.73), 126.95 (126.86), 118.94 (118.88), 80.56, 53.89 (53.71), 52.36 (52.07), 50.85 (50.80), 46.85 (46.76), 43.77 (43.58), 37.67, 35.95 (35.88), 28.64 (28.56), 28.36, 26.97 (26.92), 25.92, 21.73, 21.66 (21.63), 13.13 (13.08). mp 121-122.5° C. IR v (Diamond, cm$^{-1}$): 3273, 1713, 1609, 1521, 1413, 1158, 1028, 837. MS (ESI) m/z found 497.3 (M+H)$^+$.

(4-{1-[(4,4-Difluoro-cyclohexancarbonyl)-amino-3-[3-(3-isopropyl-5-methyl-[1,2,4]triazol-4-yl)-8-aza-bicyclo[3,2,1]oct-8-yl]-propyl}-phenyl)-carbamic acid tart-butyl ester (20)

The title compound was prepared according to the general amide coupling procedure by reacting acid 8 with amine 7 in DCM for 4 h. The crude product was purified by silica gel using DCM/MeOH (18/1) to give 269 mg white solid, in 85% yield. $^1$H NMR (400 MHz, CDCl$_3$): δ 7.34 (d, J=8.40 Hz, 2H), 7.11 (d, J=8.48 Hz, 2H), 6.67 (brs, 1H), 6.54 (d, J=7.56 Hz, 1H), 5.07 (q, J=7.01 Hz, 1H), 4.29 (m, 1H), 3.37 (m, 2H), 2.98 (seq, J=6.48 Hz, 1H), 2.49 (s, 3H), 2.40 (t, J=6.62 Hz, 2H), 2.26-3 (m, 5H), 2.06-1.94 (m, 6H), 1.93-1.63 (m, 8H), 1.51 (s, 9H), 1.38 (d, J=6.76 Hz, 6H); $^{13}$C NMR (100 MHz, CDCl$_3$): δ 173.24, 159.12, 152.82, 150.56, 137.75, 136.34, 127.11, 122.51 (J$^{13}$C-$^{19}$F 250 Hz), 118.92, 80.63, 58.87, 58.18, 51.61, 47.78, 47.28, 42.86, 35.43, 35.29, 34.66, 32.79 (J$^{13}$C-$^{19}$F 25.5 Hz), 28.32, 26.80, 26.76, 25.94 (J$^{13}$C-$^{19}$F 8 Hz), 25.85, 21.64, 13.11. mp 234-235° C. IR v (Diamond, cm$^{-1}$): 3272, 1716, 1650, 1236, 1159, 1106, 963, 836. MS (ESI) mz found 629.6 (M+H)$^+$.

(7-Amino-heptyl)-carbamic acid benzyl ester (21)

On an ice-water bath, to the solution of 1,7-diaminoheptane (1.433 g, 11 mmol) in CH$_2$Cl$_2$/MeOH (125 mL/125 mL) was added the solution of CbzCl (1.71 g, 10 mmol) in CH$_2$Cl$_2$ (250 mL) dropwise within 12 h while keeping the temperature below 5° C. The mixture was allowed to stir at the same temperature for another half of an hour before concentrated under reduced pressure to remove most of the MeOH. Water (150 mL) was then added, and the aqueous layer was adjusted to pH=2 using 6 N HCl. The layers were separated. The aqueous layer was washed with DCM (50 mL×3), then adjusted to pH=12 with 10 N NaOH and extracted with DCM (50 mL×3). The combined organic layers were dried over Na$_2$SO$_4$, concentrated and purified by flash column using DCM/MeOH (9/1) to give 856 mg white solid in 32% yield. $^1$H NMR (400 MHz, CDCl$_3$): δ 7.35-7.29 (m, 5H), 5.09 (s, 2H), 4.73 (brs, 1H), 3.18 (q, J=6.64 Hz, 2H), 2.67 (t, J=6.94 Hz, 2H), 1.55-1.44 (m, 2H), 1.44-0 (m, 2H), 1.32 (m, 6H). $^{13}$C NMR (100 MHz, CDCl$_3$): δ 156.40, 136.70, 128.50, 128.09, 128.06, 66.55, 42.18, 41.06, 33.71, 29.91, 29.09, 26.76, 26.68. mp 78-80° C. IR v (Diamond, cm$^{-1}$): 3327, 1686, 1532, 1263, 1144. MS (ESI) found 264.8 (M+H)$^+$.

[(7-Benzyloxycarbonylamino-heptylcarbamoyl)-methoxy]acetic acid (22)

To the solution of 21 (350 mg, 1.324 mmol) in THF (4 mL) was added diglycolic anhydride (161 mg, 1.39 mmol) in one portion. The resultant mixture was stirred at ambient temperature for 12 h. After removed THF under reduced pressure, the residue was crystallized by EtOAc/hexane to give 429 mg white solid as first crop, in 85% yield. $^1$H NMR (400 MHz, DMSO-d$_6$): δ12.79 (brs, 1H), 7.81 (t, J=5.52 Hz, 1H), 7.34-7.29 (m, 5H), 7.21 (t, J=5.46 Hz, 1H), 5.00 (s, 2H), 4.10 (s, 2H), 3.94 (s, 2H), 3.08 (q, J=6.56 Hz, 2H), 2.97 (q, J=6.28 Hz, 2H), 1.42-1.37 (m, 4H), 1.24 (m, 6H). $^{13}$C NMR (100 MHz, CDCl$_3$): 171.43, 168.53, 156.06, 137.30, 128.27, 127.65, 70.18, 67.88, 65.04, 40.22, 38.08, 29.65, 29.00, 28.38, 26.28, 26.14. mp 74-74.5° C. IR v (Diamond, cm$^{-1}$): 3374, 3331, 1726, 1688, 1608, 1548, 1249, 1236, 1135, 956, 701. MS (ESI) found 381.4 (M+H)$^+$.

6'β-(3,13-Dioxo-1-phenyl-2,15-dioxa-4,12-diazaheptadecanamido)morphinan (23)

The title compound was prepared according to the general amide coupling procedure by reacting acid 22 with amine 4.2HCl in DMF overnight. The crude product was purified with chromatography using CH$_2$Cl$_2$/MeOH (40/1) as eluent to give 339 mg white solid, in 76% yield. $^1$H NMR (400 MHz, DMSO-d$_6$): δ 9.01 (brs, 1H), 8.21 (d, J=8.36 Hz, 1H), 8.01 (t, J=5.60 Hz, 1H), 7.37-7.30 (m, 5H), 7.19 (m, 1H), 6.58 (d, J=8.04 Hz, 1H), 6.52 (d, J=8.04 Hz, 1H), 4.99 (s, 2H), 4.88 (brs, 1H), 4.59 (d, J=7.64 Hz, 1H), 3.94 (s, 2H), 3.93 (s, 2H), 3.53-3.45 (m, 1H), 3.18-7 (m, 2H), 3.01-2.94 (m, 4H), 2.60-2.56 (m, 2H), 2.38-2.28 (m, 2H), 2.15 (dt, J$_1$=4.89 Hz, J$_2$=12.29 Hz, 1H), 1.98 (m, 1H), 1.79 (m, 1H), 1.46-1.37 (m, 6H), 1.26 (m, 8H), 0.84 (m, 1H), 0.46 (m, 2H), 0.12 (m, 2H); $^1$H NMR (400 MHz, CDCl$_3$): δ 7.57-0.57 (d, J=9.24 Hz, 1H), 7.35-7.32 (m, 5H), 6.90 (t, J=5.66 Hz, 1H), 6.72 (d, J=8.12 Hz, 1H), 6.55 (d, J==8.16 Hz, 1H), 5.09 (s, 2H), 4.88 (m, 1H), 4.44 (d, J=5.48 Hz, 1H), 4.02 (m, 4H), 3.24 (m, 2H), 3.18 (AB, J=6.64 Hz, 2H), 3.10 (d, J=5.84 Hz, 1H), 3.03 (d, J=18.48 Hz, 1H), 2.62 (m, 2H), 2.36 (m, 2H), 2.19 (m, 2H), 1.79 (m, 1H), 1.64 (m, 1H), 1.54-1.48 (m, 7H), 1.32-1.26 (m, 7H), 0.80 (m, 1H), 0.53 (m, 2H), 0.13 (m, 2H); $^{13}$C NMR (100 MHz, CDCl$_3$): δ 168.63, 168.45, 156.51, 143.19, 139.38, 136.64, 130.56, 128.53 (×2), 128.10, 124.66, 119.23, 117.77, 92.27, 77.23, 70.89, 70.13, 66.63, 62.38, 59.40, 49.41, 47.20, 43.88, 41.02, 39.04, 31.87, 29.85, 29.50, 28.92, 28.81, 26.78, 26.55, 23.17, 22.61, 9.41, 4.00, 3.81. mp>300° C. IR v (Diamond, cm$^{-1}$): 3670, 1700, 1560, 1136. MS (ESI) m/z found 705.5 (M+H)$^+$.

6'β-{2-[2-(7-aminoheptylamino)-2-oxoethoxy]acetamido}morphinan (24)

A solution of 23 (120 mg, 0.167 mmol) in methanol (20 mL) was hydrogenated in the presence of 10% Pd/C (12 mg)

under a $H_2$ atmosphere (60 psi) at room temperature for 48 h. The mixture was filtered, and the filtrate was concentrated and purified by silica gel with DCM/MeOH (7/1) to give 24 as white foam (110 mg, 99% yield). $^1$H NMR (400 MHz, DMSO-$_6$): δ8.22 (d, J=8.40 Hz, 1H), 8.03 (t, J=5.74 Hz, 1H), 6.58 (d, J=8.04 Hz, 1H), 6.52 (d, J=8.12 Hz, 1H), 4.59 (d, J=7.36 Hz, 1H), 3.94 (s, 2H), 3.93 (s, 2H), 3.56-3.48 (m, 1H), 3.19-9 (m, 2H), 3.10 (d, J=5.52 Hz, 1H), 2.97 (d, J=18.8 Hz, 1H), 2.70 (m, 2H), 2.61-2.55 (m, 2H), 2.39-2.28 (m, 2H), 2.18-2.10 (m, 1H), 1.98 (dt, 3.56 Hz, $J_2$=11.92 Hz, 1H), 1.84-1.74 (m, 1H), 1.47-4 (m, 6H), 1.32-1.23 (m, 8H), 0.86 (m, 1H), 0.47 (m, 2H), 0.11 (m, 2H); $^1$H NMR (400 MHz, CD$_3$OD): δ6.62 (d, J=8.08 Hz, 1H), 6.55 (d, J=8.12 Hz, 1H), 4.51 (d, J=7.56 Hz, 1H), 4.06 (m, 2H), 4.05 (m, 2H), 3.76 (m, 1H), 3.26 (t, J=7.08 Hz, 2H), 3.10 (d, J=5.96 Hz, 1H), 3.07 (d, J=20.64 Hz, 1H), 2.66 (m, 2H), 2.58 (m, 2H), 2.40 (m, 2H), 2.27-2.11 (m, 2H), 1.90 (m, 1H), 1.60-1.51 (m, 6H), 1.49-1.32 (m, 8H), 0.85 (m, 1H), 0.54 (m, 2H), 0.16 (m, 21-1); $^{13}$C NMR (100 MHz, CD$_3$OD): δ 171.54, 171.38, 143.90, 142.52, 132.41, 125.06, 120.09, 118.88, 92.80, 71.74, 71.60, 71.55, 63.77, 60.32, 52.54, 48.93, 47.95, 45.28, 40.07, 32.05, 31.27, 30.43, 30.28, 28.38, 27.92, 25.51, 23.55, 22.12, 10.36, 4.49, 4.27. mp 83-85° C. IR v (Diamond, cm$^{-1}$): 3278, 3075, 1652, 1548, 1128, 1035. MS (ESI) found 571.6 (M+H)$^+$.

19-(6'β-morphinanamino)-5,15-19-trixox-3,17-di-oxa-6,14-diazanonadecan-1-oic acid (25)

To the solution of 24 (113 mg, 0.198 mmol) in DMF (2 mL) was added diglycolic anhydride (23 mg, 0.198 mmol) within 15 min. The resultant mixture was stirred at ambient temperature for 2 h. After removal of DMF under reduced pressure, the residue was crystallized by EtOAc/hexane to give 112 mg light yellow solid as first crop, in 82% yield. $^1$H NMR (400 MHz, DMSO-d$_6$): δ 9.22 (brs, 1H), 8.28 (d, J=8.32 Hz, 1H), 8.06 (t, J=5.62 Hz, 1H), 7.99 (m, 1H), 6.65 (d, J=8.12 Hz, 1H), 6.59 (d, J=8.12 Hz, 1H), 4.68 (d, J=7.80 Hz, 1H), 4.06 (s, 2H), 3.95 (s, 2H), 3.94 (m, 4H), 3.56-3.47 (m, 1H), 3.24-3.06 (m, 6H), 2.89-2.83 (m, 2H), 2.65 (m, 1H), 2.33-2.28 (m, 2H), 1.87-1.78 (m, 1H), 1.59 (m, 1H), 1.49-1.40 (m, 6H), 1.27 (m, 8H), 0.98 (m, 1H), 0.58-2 (m, 2H), 0.30 (m, 2H); $^1$H NMR (400 MHz, CD$_3$OD): δ6.72 (d, 18.20 Hz, 1H), 6.70 (d, J=8.40 Hz, 1H), 4.65 (d, J=7.80 Hz, 1H), 4.07 (s, 2H), 4.06 (s, 2H), 3.98 (s, 2H), 3.93 (s, 2H), 3.77-3.71 (m, 2H), 3.31-3.22 (m, 4H), 3.14-2.99 (m, 3H), 2.94-2.89 (m, 1H), 2.78 (dd, $J_1$=7.34 Hz, $J_2$=13.30 Hz, 1H), 2.59-2.46 (m, 2H), 2.03-1.92 (m, 1H), 1.73-1.61 (m, 2H), 1.59-1.50 (m, 6H), 1.37 (m, 6H), 1.06 (m, 1H), 0.77-0.63 (m, 2H), 0.42 (m, 2H); $^{13}$C NMR (100 MHz, CD$_3$OD): δ 177.25, 172.58, 171.61, 171.56, 143.81, 142.81, 131.26, 128.73, 120.70, 119.42, 92.23, 72.25, 71.67, 71.58, 71.47, 71.39, 64.21, 59.23, 52.37, 49.30, 47.97, 40.10, 39.96, 31.20, 30.26, 30.21, 29.95, 29.76, 27.81, 27.79, 24.91, 24.24, 7.78, 5.67, 3.68. mp 193° C. dec. IR v (Diamond, cm$^{-1}$): 3271, 3069, 1732, 1651, 1548, 1125, 1033. MS (ESI) m/z found 687.4 (M+H)$^+$.

Methylcarbamoylmethoxy-acetic acid (26)

The title compound was prepared using the same procedure as described by Zheng et al.[30b], except that white solid instead of oil was obtained. $^1$H NMR (400 MHz, DMSO-d$_6$): δ 12.77 (brs, 1H), 7.77 (brs, 1H), 4.10 (s, 2H), 3.94 (s, 2H), 2.62 (d, J=4.8 Hz, 3H). $^{13}$C NMR (100 MHz, DMSO-d$_o$): δ 171.32, 169.08, 70.09, 67.77, 25.11. mp 33-33.5° C.

(7-{2-[(4-{1-[(4,4-Difluoro-cyclohexanecarbonyl)-amino]-3-[3-(3-isopropyl-5-methyl-[1, 2,4]triazol-4-yl)-8-aza-bicyclo[3.2.1]oct-8yl]-propyl}-phenylcar-bamoyl)-methoxy]-acetyl amino}-heptyl)-carbamic acid benzyl ester (27).

The title compound was prepared according to the general amide coupling procedure by reacting acid 22 with amine 6 in DMF overnight. The crude product was purified with chromatography using CH$_2$Cl$_2$/MeOH (13/1) as eluent to give 260 mg white foaming, in 72% yield. $^1$H NMR (400 MHz, CDCl$_3$): δ8.96 (s, 1H), 7.57 (d, J=8.48 Hz, 2H), 7.35-7.27 (m, 5H), 7.24 (d, J=8.48 Hz, 2H), 6.75 (m, 1H), 6.70 (m, 1H), 5.12-5.08 (m, 3H), 4.91 (m, 1H), 4.29 (m, 1H), 4.14 (s, 2H), 4.09 (s, 2H), 3.40 (m, 1H), 3.37 (m, 1H), 3.30 (q, J=6.68 Hz, 2H), 3.15 (q, J=6.71 Hz, 2H), 2.99 (m, 1H), 2.48 (s, 3H), 2.43 (t, J=6.48 Hz, 2H), 2.30-4 (m, 6H), 2.01-1 (m, 8H), 1.70-1.46 (m, 9H), 1.376 (d, J=6.80 Hz, 3H), 1.373 (d, J=6.84 Hz, 3H), 1.35-1.31 (m, 6H); $^{13}$C NMR (100 MHz, CDCl$_3$): δ 173.50, 168.64, 167.15, 159.17, 156.55, 150.59, 138.31, 136.66, 136.51, 128.54, 128.12, 128.00, 127.12, 120.51, 77.24, 71.66, 71.50, 66.60, 58.90, 58.30, 51.68, 47.77, 47.24, 42.83, 40.98, 39.14, 35.33, 34.59, 32.82 (J$^{13}$C-$^{19}$F 25.7 Hz), 29.82, 29.36, 28.71, 26.75 (J$^{13}$C-$^{19}$F 10 Hz), 26.48, 25.87, 21.65, 13.15. mp 65-67° C. IR v (Diamond, cm$^{-1}$): 3273, 1656, 1529, 1515, 1251, 1106, 697. MS (ESI) m/z found 891.9 (M+H)$^+$.

4,4-Difluoro-cyclohexanecarboxylic acid {1-(4-{2-[(7-amino-heptylcarbamoyl)-methoxy]-acety-lamino}-phenyl)-3-[3-(3-isopropyl-5-methyl-[1,2,4] triazol-4-yl)-8-aza-bicyclo[3.2.1]oct-8-yl]-propyl}-amide (28)

A solution of 27 (260 mg, 0.291 mmol) in methanol (15 mL) was hydrogenated in the presence of 5% Pd/C (26 mg) under a $H_2$ atmosphere (60 psi) at room temperature for 48 h. The mixture was filtered, and the filtrate was concentrated to give 28 as white foaming (113 mg, 51% yield). $^1$H NMR (400 MHz, CDCl$_3$): δ 8.80 (s, 1H), 7.58 (d, J=8.48 Hz, 2H), 7.25 (d, J=8.48 Hz, 2H), 6.61 (d, J=7.48 Hz, 1H), 6.47 (m, 1H), 5.10 (q, J=7.00 Hz, 1H), 4.30 (m, 1H), 4.17 (s, 2H), 4.12 (s, 2H), 3.40-0 (m, 4H), 2.98 (seq, J=6.90 Hz, 1H), 2.68 (t, J=6.84 Hz, 2H), 2.48 (s, 3H), 2.43 (t, J=6.62 Hz, 2H), 2.26-2.12 (m, 5H), 2.08-3 (m, 16H), 1.44 (qu, J=6.72 Hz, 2H), 1.383 (d, J=6.76 Hz, 3H), 1.382 (d, J=6.80 Hz, 3H); 1.34-0 (m, 6H); $^1$H NMR (400 MHz, CD$_3$OD): δ7.60 (d, J=8.52 Hz, 2H), 7.33 (d, J=8.56 Hz, 2H), 5.03 (t, J=7.34 Hz, 1H), 4.39 (m, 1H), 4.20 (s, 2H), 4.12 (s, 2H), 3.41 (m, 2H), 3.30-3.21 (m, 3H), 2.69 (t, J=7.32 Hz, 2H), 2.50 (s, 3H), 2.46-2.41 (m, 2H), 2.40-2.30 (m, 1H), 2.30-2.05 (m, 2H), 2.05-2.03 (m, 4H), 2.02-1.96 (m, 2H), 1.89-1.65 (m, 10H), 1.60-1.45 (m, 4H), 1.36-4 (m, 12H); $^{13}$C NMR (100 MHz, CDCl$_3$): δ 176.59, 171.68, 170.07, 161.41, 152.60, 140.39, 138.07, 128.21, 123.91 (J$^{13}$C-$^{19}$F 239 Hz), 121.88, 71.95, 71.75, 60.69, 60.19, 52.41, 43.69, 42.03, 40.07, 36.77, 36.16, 33.90 (J$^{13}$C-$^{19}$F 24 Hz), 33.87 (J $^{13}$C-$^{19}$F 24 Hz), 32.28, 30.38, 30.11, 27.86, 27.78, 27.20 (1 $^{13}$C-$^{19}$F 9 Hz), 27.05 (J$^{13}$C-$^{19}$F 9 Hz), 26.76, 22.07, 12.45. mp 100-102° C. IR v (Diamond, cm$^{-1}$): 3256, 1651, 1538, 1515, 1261, 1103, 743. MS (ESI) found 757.9 (M+H)$^+$.

Calcium Mobilization Assay

The ligands were first tested with various doses (in the range of 0.1 nM to 1 μM) for possible agonist activity. The protocol was the same for the following antagonism study, except no CCL5 (RANTES) was added. MOLT-4/CCR5 cells were plated in black 96-well plates with transparent bottom (Greinier Bio-one) at 100,000 cells per well in 50:1 HBSS: HEPES assay buffer. They were incubated for 1 hour at 37° C. and 5% $CO_2$ with control buffer or varying concentration of ligand for a total volume of 130 μL per well. Cells were then incubated with 50 μL of Fluo-4-AM loading buffer (40 μL 2 μM Fluo-4 dye, 100 μL 2.5 mM probenacid, in 5 mL assay buffer) for an additional hour. Then 20 μL. 200 nM RANTES solution in assay buffer or assay buffer alone were added to the wells right before changes in $Ca^{2+}$ concentration were monitored by RFU for 90 seconds using a microplate reader (FlexStation3, Molecular Devices). Peak values were obtained using SoftMaxPro software (Molecular Devices) and non-linear regression curves were generated using Prism (GraphPad) to calculate $IC_{50}$ values.

The Mu Opioid Receptor Binding and Functional Assay
MOR/CHO cell culture and membrane homogenate preparation followed literature report[52].

Opioid Receptor Binding:
Saturation binding was performed by incubating membranes for 90 minutes at 30° C. with 0.5-15 nM [$^3$H]naloxone in assay buffer in a 0.5 mL volume. Non-specific binding were determined with 5 μM naltrexone. For competition assays, membranes were incubated as above with 2 nM [$^3$H]naloxone and various concentrations of unlabeled ligand, to determine competitor $IC_{50}$ for MOR. The reaction was terminated by rapid filtration through Whatman GF/B glass fiber filters, followed by 3 washes with 3 mL ice-cold Tris buffer. Bound radioactivity will be determined by liquid scintillation spectrophotometry at 45% efficiency for [$^3$H].

[$^{35}$S]GTPγS Binding:
Membranes (10 μg protein) were incubated in assay buffer at 30° C. for 90 min with various drugs, 10 μM GDP (cells) and 0.1 nM [$^{35}$S]GTPγS in 0.5 mL total volume for appropriate times. Basal binding was assessed in the absence of agonist, and nonspecific binding was measured with 10 μM unlabeled GTPγS. The reaction was terminated by rapid filtration as described above. Bound radioactivity was determined by liquid scintillation spectrophotometry at 95% efficiency.

Data Analysis:
For competition binding assay (agonists or antagonists), Hill plots linear regression analysis and the Cheng-Prusoff equation were applied to determine the $IC_{50}$ and $K_i$ values. In [$^{35}$S]GTPγS binding assays, agonist concentration effect curves were fit by non-linear regression to obtain $E_{max}$ and $EC_{50}$ values; antagonist inhibition of agonist-stimulated [$^{35}$S] GTPγS binding was analyzed by Hill analysis and $AD_{50}$ values were corrected to $K_i$ values using the Cheng-Prusoff equation. All analyses were using Prism 4.0.

Example 2

Significant Drug Interactions Between Maraviroc and Morphine in Astrocytes: Implications for a New Therapeutic Against neuroAIDS in Drug Abusing Populations Abstract
Opiates have been previously reported to enhance the ability of CCR5 (R5)-tropic HIV-1 strains to infect macrophages through the upregulation of CCR5 receptor expression. Moreover, the μ-opioid receptor (MOR) and CCR5 have been shown to undergo bidirectional heterologous sensitization. To explore whether opiates affect the actions of CCR5 HIV-1 entry inhibitors, the effects of morphine on the CCR5 antagonist maraviroc, as well as a bivalent derivative of maraviroc linked to naltrexone (described in Example 1), on HIV-1 entry was evaluated in primary human astrocytes. HIV-1 entry was monitored in astrocytes transiently transfected with a LTR construct containing a luciferase reporter gene under control of a promoter for the HIV-1 transactivator protein Tat. The effect of maraviroc and the bivalent ligand±morphine on CCR5 surface expression and cytokine release was also explored. The data shows that maraviroc inhibits HIV-1 entry into astrocytes, while morphine negates the effects of maraviroc leading to a significant increase in viral entry. It is also demonstrated that utilizing maraviroc in the form of a bivalent ligand has a more potent inhibitory effect on R5-tropic viral entry in astrocytes compared to maraviroc alone. More importantly, the inhibitory effects of the bivalent compound were not compromised by morphine. Moreover, exposure to maraviroc or the bivalent compound decreased the release of pro-inflammatory cytokines and restricted HIV-1-dependent increases in CCR5 expression. The results indicate that opiate abuse might limit the antiretroviral effects of maraviroc, which could lead to accelerated brain neuropathogenesis. Thus, the coordinated blockade of MOR and CCR5, using novel bivalent compounds, is an appropriate therapeutic strategy in drug-abusing HIV-infected populations.

Introduction
A novel approach to targeting these protein complexes is through the use of newly synthesized bivalent ligands to target the reputed dimers/oligomers. Example 1 describes the synthesis of one exemplary ligand. The impact of morphine on the inhibitory effects of maraviroc on HIV-1 entry in primary human astrocytes was investigated. MOR is known to undergo extensive alternative splicing, and it is known that increased numbers of MOR splice variants expressed in astrocytes as compared to that in microglia. We explored the potential inhibitory effects of a bivalent ligand carrying the MOR antagonist, naltrexone, and the CCR5 antagonist, maraviroc, on HIV-1 viral entry, and the impact of morphine on this small molecule bivalent antagonist to repress viral invasion. We observed a more effective antiviral entry effect using the bivalent compound in astrocytes as compared to microglia at the concentrations used in our study. A possible explanation for this discrepancy between cell types may relate to the concentrations used, suggesting that higher concentrations of ligand may be required for inhibition of HIV-1 entry into microglia than astrocytes, but also to the different splice variants present in astrocytes and not in microglia. Therefore, the studies were conducted using astrocytes. Additional reasons for using this cell type include the fact that astrocytes represents a major population of non-neuronal cells in the brain that comprise about 25-50% of the total brain volume, these cells are latently infected with HIV-1 and represent a good reservoir for the virus, but most importantly, astroglia play a key role in the neuropathogenesis of HIV-1. The data shows that morphine impairs the effect of maraviroc and increases the susceptibility of HIV-1 entry into astrocytes, suggesting that morphine could cause viral treatment failure leading to accelerated neuropathogenesis in the brain of infected drug abusers. Exposure to maraviroc in the form of the bivalent ligand caused a significant decrease in HIV-1 viral entry when compared to exposure to maraviroc alone or maraviroc plus naltrexone, indicating that the bivalent ligand works better when the two antagonists are linked. The data shows that the novel bivalent ligand used for viral inhibition is more effective than maraviroc alone and is a useful strategy to limit bystander effects on other cell types from infected astroglia, particularly in populations susceptible to drug abuse.

Materials and Methods
Reagents

Morphine sulfate was obtained from the National Institute on Drug Abuse (NIDA; Drug Supply System, Bethesda, Md.). Naltrexone and the HIV-1 co-receptor antagonist, maraviroc, were purchased from Sigma-Aldrich (St. Louis, Mo.). The bivalent compound was provided by Dr. Yang Zhang in the Department of Medicinal Chemistry at Virginia Commonwealth University.

Cell Culture and Treatments

Primary human astrocytes (ScienCell catalog #1901) were cultured in 24-well plates and transfected with the plasmid pBlue3'LTR-luc (NIH AIDS Research and Reference Reagent Program) using Lipofectamine 2000 (Invitrogen) followed by infection with HIV-1. After 18-20 h cells were rinsed twice in 1×PBS then lysed in Cell Culture Lysis Reagent (Promega) and relative Tat protein expression was determined by measuring luciferase activity using the Luciferase Assay System (Promega; catalog #E1500). Light units were measured using a PHERAstar FS plate reader (BMG Labtech). The HIV-1 co-receptor antagonist, maraviroc, and bivalent compound were used at increasing concentrations of (10, 50, 100, 500 nM) 30-60 min prior to HIV-1 infection to selectively block viral entry.

HIV-1 Infection of Glial Cells

Primary human astroglial cells were infected by incubation with the neurotropic HIV-1 strain $SF_{162}$. A concentration of HIV-1 p24 50 pg/$10^6$ cells [9] was used, and a no virus condition served as a negative control. Viral stocks were quantified by assaying for HIV-1 p24 (Alliance p24 Antigen ELISA Kit; Advanced Bioscience, Kensington, Md.).

Flow Cytometry

MOR and CCR5 immunoreactivity were detected by direct immunofluorescence in astroglial cells by flow cytometric analysis. Cells were washed in phosphate-buffered saline (PBS)—0.1% bovine serum albumin (BSA) buffer and incubated with primary MOR antibody followed by a secondary antibody conjugated to allophycocyanin (APC) (Biolegend, Inc; catalog #408001) and Alexa Fluor® 488 conjugated anti-mouse CD195 (CCR5) antibody (Biolegend, Inc; catalog #107008) in permeabilization buffer (PBS-0.1% BSA-0.1% Triton X-100) at a 1:500 dilution. Fluorescence was measured from 10,000 gated cells per treatment in each experiment using a FACSCanto II flow cytometer (BD Biosciences, San Jose, Calif.). Auto-fluorescence was compensated by setting the detector voltage to the minimum level that discriminates between auto-fluorescence and specific immunofluorescence in both negative and positive controls. Isotype control antibodies were used to define settings in histogram plot analyses.

Confocal Microscopy

For direct visualization of viral entry, fluorescent HIV-1 particles were generated by co-transfection of a vector containing a full-length R5-tropic HIV-1 provirus (NIH AIDS Research & Reference Reagent Program, Division of AIDS, NIAID, NIH: pWT/BaL (catalog #11414) and Vpr-GFP into HEK-293T cells as described in [9]. Primary astroglial cells were infected with the HIV-1$_{Bal}$ Vpr-GFP particles in the absence or presence of 100 nM bivalent ligand for 18 to 20 h at 37° C., washed in PBS, fixed with 4% paraformaldehyde, and counterstained with DAPI. Cells were imaged using a Zeiss LSM 700 laser scanning confocal microscope equipped with a 63× (1.42 numerical aperture [NA]) objective, using 488-nm laser excitation with dichroic beam-splitter set at 492 nm to optimize GFP detection.

Cytokine Release

The protein levels of the cytokines TNF-α, IL-6, IL-1β and the chemokine RANTES were measured by ELISA (Quantikine kits; R&D Systems Minneapolis, Minn.).

Cytotoxicity Assay

Cell viability was assessed by measurement of both live and dead cells using dual (green/red) fluorescence labeling with AOPI analyzed with Cellometer Vision CBA (Nexcelom Bioscience LLC).

Data Analysis

Data were analyzed using analysis of variance (ANOVA) techniques (SYSTAT 11.0 for Windows, SYSTAT Inc.) followed by Duncan's post-hoc analyses. An alpha level of $p<0.05$ was considered significant for all statistical tests used. Data are presented as ±SEM.

Results

The Molecular Structure of the Bivalent Ligand

Figure 2A:
FIG. 2. A. Construction of a MOR—CCR5 dimer model B. Construction of a chemical probe that interacts with both the MOR and CCR5 receptors simultaneously.
Figure 2B:
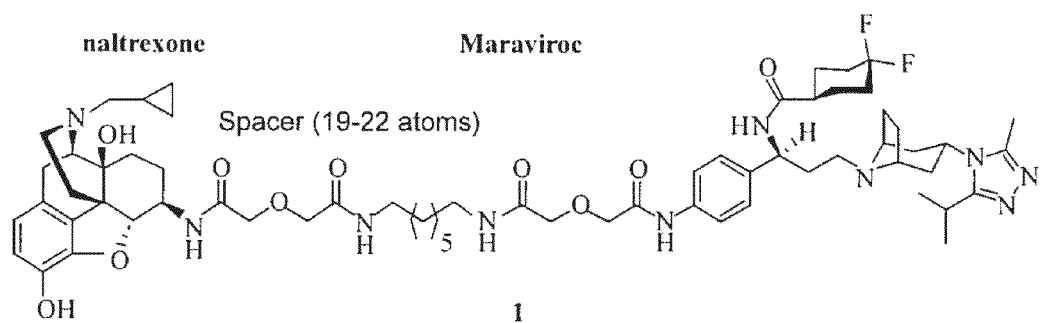

The bivalent ligand was designed and synthesized as described in Example 1. A dimeriization model of CCR5 and MOR is depicted in FIG. 2A, and the bivalent ligand itself if shown in FIG. 2B. Naltrexone, the MOR pharmacophore, has been successfully used to investigate the dimerization of opioid receptors and it is clinically used to treat opiate addiction and alcoholism. Both naltrexone and maraviroc show high affinity and reasonable selectivity toward MOR and CCR5, respectively. The locus on each pharmacophore for tethering two pharmacophores through a spacer has been shown to affect the binding affinities of the resulting bivalent ligands. The consensus of several studies is that a spacer 16 to 22 atoms in length is most beneficial for targeting GPCR dimers, ideally with 21 atoms when both pharmacophores are antagonists of their respective receptors. The rationale for design of such spacers (containing one alkyldiamine moiety and two diglycolic units) was to keep a favorable balance between hydrophobicity and hydrophilicity as well as to possess reasonable rigidity, high stability and low toxicity.

Antiviral Effect of Maraviroc and the Bivalent Ligand in Human Astroglial Cells

Figure 3A:
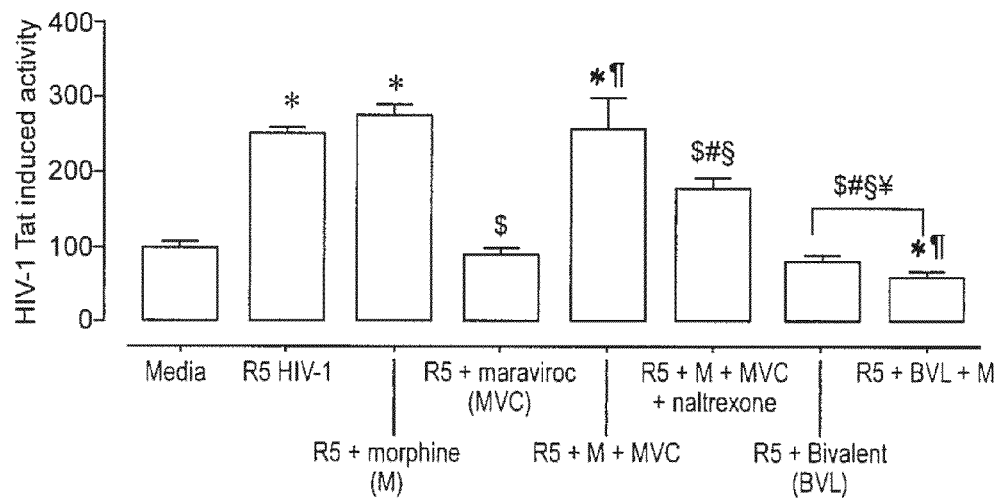
FIG. 3. The CCR5 antagonist maraviroc and a bivalent ligand derivative inhibit HIV-1 entry into astrocytes with differential attenuation by morphine. A. HIV-1 infection was monitored by Tat protein expression in human astrocytes transfected with the plasmid pBlue3'LTR-luc using the Luciferase Assay System (Promega). Cells were treated with maraviroc (MVC; 100 nM), morphine (M; 500 nM) or the bivalent ligand (BVL; 100 nM) followed by infection with HIV-1(R5) at a concentration of HIV-1 p24 50 pg/$10^6$ cells. Values are luminescence±SEM of 3-5 independent experiments at 18 h post-infection (*$p<0.005$ vs. un-infected cells; $^{\$}p<0.05$ vs. R5 HIV-1; $^{\#}p<0.05$ vs. R5+morphine (M); $^{\P}p<0.05$ vs. R5+maraviroc (MVC); $^{\S}p<0.05$ vs. R5+M+

HIV-1$_{SF162}$ infectivity of human astroglia was determined based on the relative amount of Tat protein expressed by the virus using a luciferase-based reporter assay. Reporters under the control of the long terminal repeat (LTR) viral promoter are a robust means of measuring HIV-1 infection, since the LTR is activated by HIV-1 Tat, which is only expressed by infected cells. We chose the 18-20 hour time point because we wished to be certain that entry of virus in the control experiments and opioid treated experiments had occurred. Additionally, we wanted to pick a time after morphine-MOR has internalized (~17 h) and when virus has completed a full cycle of replication (~24 h) to assess the efficacy of the viral entry inhibitor drugs and impact of morphine on the replicative capacity of the virus. After incubation with R5-tropic HIV-1$_{SF162}$ alone or in combination with morphine (M), relative Tat expression was significantly increased in human astrocytes (FIG. 3A). In fact, we observed a ~2.5- and 2.7-fold increase in Tat expression after infection with HIV-1 (R5) alone and R5 in combination with morphine (M), respectively. As expected, the HIV-1 entry inhibitor maraviroc (MVC) prevented virus from entering the cells and caused a 2.8-fold decrease in Tat expression when compared to exposure to virus alone, while MVC in combination with morphine completely abolished the antiviral effect of MVC, and caused a significant increase in viral entry with a 2.6-fold increase in the amount of Tat expressed. Surprised by this finding, we asked whether the presence of the MOR antagonist, naltrexone (NTX), in combination with MVC would counteract the effect of morphine, and indeed, Tat expression was significantly less in combination MVC with NTX plus morphine.

Figure 3B:
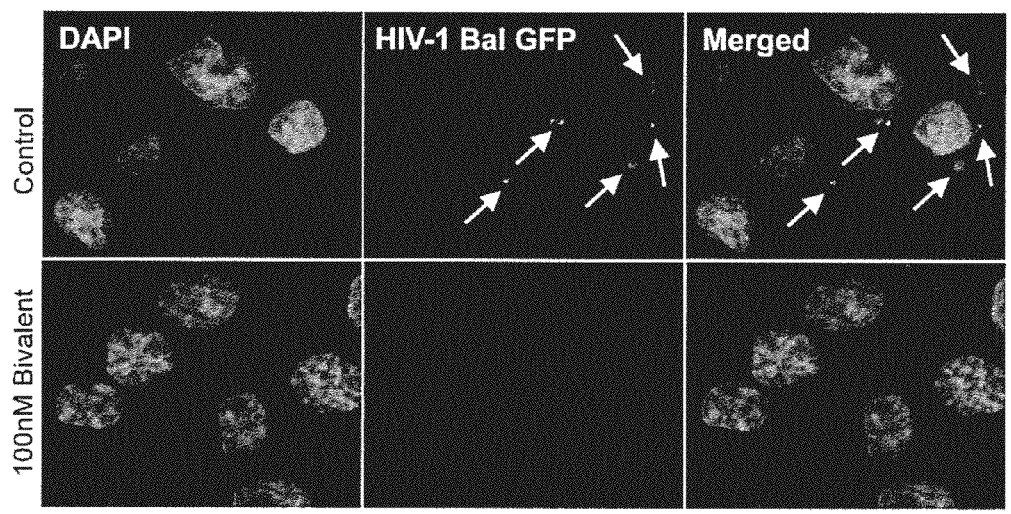

Next we tested the antiviral effect of a newly synthesized bivalent ligand as compared to its component parts and determined whether morphine influenced the effect of the bivalent ligand on HIV-1 viral entry as well. Addition of the bivalent ligand was extremely effective in inhibiting viral entry and caused a 4.4-fold decrease in Tat expression when compared to R5 HIV-1 alone and a 2.0-fold decrease when compared to R5 plus MVC. Likewise, the bivalent compound plus morphine caused a significant decrease in Tat expression that was 2.9-fold decreased when compared to R5 plus MVC and 4.4-fold decrease when compared MVC with NTX plus morphine. These results show that morphine impairs the antiviral function of maraviroc in human astroglia and that the newly synthesized bivalent ligand can function as a potent inhibitory drug in astrocytes regardless of morphine interactions. The data also show that exposure to maraviroc in the form of the bivalent ligand is more effective in viral inhibition as compared to exposure to maraviroc alone or maraviroc plus Naltrexone, indicating that the bivalent ligand works better when the two antagonists are linked together. To further demonstrate that HIV-1 entry into astroglial cells is inhibited by the bivalent compound, we inoculated these cells with R5-tropic HIV-1$_{Bal}$ tagged with Vpr-GFP and visualized GFP-tagged virions by confocal microscopy in the absence or presence of 100 nM of the bivalent ligand. Although most cells were not GFP positive, astroglial cells possessing internalized Vpr-GFP were clearly evident (FIG. 3B, where arrows indicate viral particles) and the presence of the bivalent ligand abolished viral entry (FIG. 3B; lower panel).

The Bivalent Compound Increases the Expression of CCR5 but not MOR in Human Astroglial Cells We quantitatively analyzed the effect of MVC and the bivalent compound on CCR5 and MOR expression levels in virally infected astrocytes by flow cytometry. Plots of APC vs. Alexa Fluor 488 histograms showed the isotype control and two-way CCR5 with MOR fluorescence intensity associated with astrocytes. Approximately 20,000 events were analyzed per treatment condition in each experiment and size discrimination was used as a crude method for viability determination. Based on the forward scatter (FSC) and side scatter (SSC), we concluded that the astrocyte population was not very homogenous, with a small percent of the total population expressing MOR while the majority of the cells expressed CCR5 and a subset of the population expressed both CCR5 and MOR (FIG. 4). Interestingly, the expression of MOR remained unchanged throughout each treatment, while the receptor level of CCR5 was significantly increased after exposure to infection. In fact, the CCR5 expression levels in astrocytes exposed to HIV-1 R5 alone or in combination with morphine had a 4.3- and a 3.3-fold increase, respectively, while co-exposure with maraviroc caused a 1.6-fold decrease in protein expression levels when compared to R5 HIV-1 infected cells. Likewise, exposure with bivalent ligand morphine caused a 1.8-fold decrease in CCR5 expression levels when compared to R5 HIV-1 alone. Interestingly, the number of astrocytes expressing both CCR5 and MOR significantly increased after infection with R5 HIV-1, while exposure with the bivalent ligand caused a 1.6-fold increase in receptor expression when compared to R5 HIV-1 alone.

The data show that astrocytes express MOR and chemokine CCR5 receptors and that the protein level of CCR5 was upregulated by HIV-1 and MOR activation.

Viral Inhibition Decreases the Release of Pro-Inflammatory Cytokines in Human Astroglial Cells.

In an effort to determine whether viral entry inhibitors reduce the inflammatory effect associated with viral infection, HIV-1-induced pro-inflammatory cytokines were measured in HIV-1 infected astrocytes treated with maraviroc and the bivalent ligand. After 18-20 h exposure, supernatant was removed and analyzed by ELISA to quantitatively analyze the release of the cytokines TNF-α, IL-1β and IL-6 and the chemokine RANTES. Release of IL-10 was below detection levels and not reported. Exposure to HIV-1 caused a significant increase in the release of TNF-α, IL-6 and RANTES that was anywhere between 1.5- to 3-fold higher when compared with media alone, while combination with morphine caused a further increase in IL-6 that was significantly more when compared to HIV-1-infected supernatant alone (FIG. 5). Infected astrocytes exposed to MVC had a 2.0-, 1.5- and a 3.2-fold decrease in TNF-α, IL-6 and RANTES release, respectively, when compared to R5 HIV-1 alone. Astrocytes treated with R5 plus MVC and morphine caused a 1.5- and 3.0-fold increase in IL-6 and RANTES, respectively, when compared to astrocytes treated with R5+MVC. Likewise, exposure with the bivalent ligand morphine caused a 2.0-, 1.6-, and 1.5-fold decrease in TNF-α, IL-6 and RANTES release, respectively, when compared to R5 HIV-1 alone. These results show that in addition to viral inhibition, the CCR5 antagonist can also serve as an anti-inflammatory agent in astrocytes. Interestingly, although the bivalent ligand was more effective than MVC in inhibiting viral entry, the compound was not significantly more effective in abolishing the HIV-1 induced inflammatory effect, which may account for the increase in chemokine receptor we observed.

Effect of Experimental Treatments on Cell Viability.

To determine whether HIV-1±morphine exposure affected astrocyte viability in the presence or absence of MVC or the bivalent compound, a cell death assay was performed at 24 h after treatment. While we observed a slight decrease in cell viability after exposure to MVC, it was not significantly different when compared to uninfected astrocytes. HIV-1±morphine with or without MVC or the bivalent ligand did not significantly affect the survival of astrocytes (FIG. 6).

Discussion

Convincing evidence that opiates worsen the pathophysiology of neuroAIDS in conjunction with growing concerns of drug-drug interactions between drugs of abuse and ART has lead to the development of new therapeutic strategies that target opioid abuse and HIV-1 co-morbidity. In this Example, we observed that (1) maraviroc inhibits HIV-1 entry into astrocytes, and (11) co-exposure with morphine negates the effects of maraviroc leading to a significant increase in viral entry. We also demonstrate that (III) the newly synthesized bivalent ligand carrying both a MOR and CCR5 antagonist has a more potent inhibitory effect on R5-tropic viral entry in astrocytes compared to maraviroc alone, and (IV) the inhibitory effects of the bivalent compound were not compromised by morphine. Although the exact mechanism by which morphine overrides maraviroc action is not known, it is well accepted that activation of MOR leads to up regulation of CCR5 in human host cells and facilitates HIV-1 infection and replication. These observations agree with our flow cytometry data (FIG. 4), in that CCR5 protein levels were significantly elevated in astrocytes after viral exposure alone or in combination with morphine. Exposure to maraviroc followed by viral infection caused a decrease in receptor levels, while co-exposure with morphine reversed the maraviroc effect and caused an increase in CCR5 protein. It is possible that the presence of morphine amplifies the levels of CCR5 to the point that the amount of maraviroc used is not sufficient to cover all the receptors present. In an attempt to clarify this observation, we used a higher concentration of maraviroc but detected increased toxicity to the cells. The "dimerization-oligomerization" concept for GPCRs has been widely accepted following revealing research of several groups on the $GABA_B$ receptor, and later with X-ray crystal structures. The dimerization/oligomerization of GPCRs poses a differentiated pharmacology from that of the monomers. Thus, opiates have been proposed to affect HIV-1 entry and infectivity via direct molecular interactions between MOR and CCR5 and through convergent downstream signaling. In this regard, a number of bivalent ligands have been synthesized to explore the underlying biology and pharmacological mechanisms of GPCR dimerization/oligomerization, as well as to develop prospective agents with enhanced affinity and/or selectivity to treat different disorders and diseases by targeting this "novel" mechanism. While we did observe a more effective antiviral entry effect using the bivalent compound, the antiviral effect with the bivalent ligand was only detected in astrocytes and not in microglia (data not shown) at the concentrations used in our study. This result suggests that higher concentrations of ligand may be required for inhibition of HIV-1 entry into microglia than astrocytes. The concentration of 100 nM was used for maraviroc and the bivalent ligand, because, as mentioned above, a higher concentration of maraviroc showed increased toxicity to the cells. Thus, as the bivalent ligand requires the presence of both MOR and CCR5 for maximal binding interactions, the expression of more variants of MOR in astrocytes may require less ligand for inhibition of viral entry into this cell type. Also of importance is the affinity of the naltrexone moiety of the bivalent ligand for different MOR splice variants as well as the affinity of different MOR variants for heterodimerzation with CCR5 [27]. The crystal structure of human MOR has recently been solved.

The newly synthesized ligand used in this report interacts simultaneously with MOR and CCR5 receptors, and besides the novelty of its chemical property, this chemical probe was never tested before for its function as an antiviral drug. Interestingly, because of its specificity to the inhibition of viral entry into astrocytes, the bivalent compound will be of particular importance to decrease viral reservoirs in astrocytes which could lead to less damage to the surrounding neurons from chronic infection. It will also serve as a useful In this Example, it is shown that an opiate can limit the antiretroviral effects of maraviroc, which likely leads to accelerated brain neuropathogenesis, and that the coordinated blockade of MOR and CCR5, using this novel bivalent compound, is a viable therapeutic strategy.

Example 3

Bivalent Ligands Specifically Target the Mu Opioid Receptor and the Chemokine Receptor CCR5 Functional Heterodimer in Both HIV-1 Infectious and Non-Infectious Cellular Systems Introduction Previously, a bivalent compound containing both a mu opioid receptor (MOR) and chemokine receptor CCR5 (CCR5) antagonist pharmacophore was synthesized in order to study the pharmacological profile of MOR CCR5 heterodimerization and its relation with neurodegenerative AIDS (see Example 1 for synthesis). Herein, studies of the structural-activity relationship between the bivalent compound and the heterodimer with both functional assays and HIV-1 fusion assays are described. A second bivalent compound (VZMC5; 2, FIG. 7) was synthesized, containing maraviroc (CCR5 antagonist) and naltrexone (MOR antagonist) moieties like the original bivalent compound (VZMC1; 1, FIG. 7); however, spacer attachment between the two moieties was switched from para to meta on maraviroc. VZMC2 was synthesized as described in Example, 1, except the starting material is 3-bromocinnacid instead of 4-bromocinnacid while the syntheses route and procedure was otherwise very similar.

Additional control compounds were synthesized to study how substitution on maraviroc affected CCR5 binding and functional activity, FIG. 8. Calcium mobilization assays were used to determine the functional activity of the compounds to both the MOR and the CCR5. Cell fusion assays that mimic HIV-1 invasion were then carried out to access VZMC1 and VZMC5 inhibition on cell fusion. Since the fusion assay may not reflect how native cells and HIV-1 interact, a HIV-1 infection assay using human astrocytes was used to assess how the compounds inhibited infection compared to maraviroc. In order to observe how the compounds interact with the CCR5-MOR heterodimer on the atomic level, computation methods such as molecular dynamics simulations was used.

Results and Discussion

Establishing a CCR5-MOR CHO Cell Line

Having a cell line that consistently expresses both CCR5 and MOR was essential for studying how the two receptors interact with each other using calcium mobilization assays and cell fusion assays. A previously established MOR Chinese hamster ovarian (CHO) cell line was transfected with a plasmid containing CCR5 tagged with a yellow fluorescent protein on its N-terminus (CCR5-YFP).[1] After 48 hours cells were sorted based upon the presence of the yellow fluorescent protein tag using a flow cytometer. Cells containing the tagged receptors were then cultured and used in the subsequent assays.

Calcium Mobilization Assays

Calcium mobilization is directly related to G protein-coupled receptor (GPCR) activation and therefore is a useful technique to study the functional activity of new ligands. Using the CCR5-MOR CHO cell line the activity at both receptors was studied for compounds 1-8. Before the assay cells were transfected with a chimeric G protein $G_{qi5}$ in order to boost the calcium signaling and couple to MOR signaling to calcium mobilization.[2] All compounds were tested for both their agonism and antagonism and none showed any agonism. Table 1 shows the $IC_{50}$'s for the compounds using either DAMGO (MOR agonist) or RANTES (CCR5 agonist) to stimulate calcium mobilization.

TABLE 1

Results from calcium mobilization assays using the CCR5-MOR CHO co-expressed cell line.

| Compound | MOR $IC_{50}$ (nM)[a] | CCR5 $IC_{50}$ (nM)[b] |
| --- | --- | --- |
| 1 | 29.99 ± 244 | 6242 ± 251 |
| 2 | 17.36 ± 5.74 | 14035 ± 345 |
| 3 | — | 8818 ± 870 |
| 4 | — | 6669 ± 544 |
| 5 | — | 54.84 ± 11.2 |
| 6 | — | 7025 ± 402 |
| 7 | — | 2202 ± 8.5 |
| 8 | 50.52 ± 4.83 | — |
| Naltrexone | 5.83 ± 2.52 | — |
| Maraviroc | — | 17.75 ± 4.28 |

[a]cells were stimulated with DAMGO,
[b]cells were stimulated with RANTES,
— denotes that the compound was not tested.

The results from MOR antagonism indicate that all of the compounds maintain their ability to antagonize DAMGO signaling. However, compared to naltrexone compounds 1, 2, and 8 have higher $IC_{50}$'s which indicates a loss in activity. The loss ranges from 3-fold to 10-fold compared to naltrexone. Interestingly, the bivalent compounds 1 and 2 are more potent than the control compound 8. The difference in activity could arise between the compounds due to 8 lacking the maraviroc portion of the full bivalent compounds. Since 1 and 2 have both antagonists present they can interact with both CCR5 and MOR concurrently which could synergistically lower their $IC_{50}$'s and thus increasing their binding affinity to the MOR receptors. Compound 8 lacks such synergism since it can only interact with MOR.

The CCR5 antagonism results from the calcium mobilization assays indicate that modification of maraviroc through the phenyl substituents is not well favored. Addition of an amino group at the para position, compound 5 is the only well tolerated change with only a 3-fold loss in activity. However, as the substituent starts to become bulkier, 3 and 4, there is a drastic decrease in activity of around 400-fold compared to maraviroc. The same is seen for the control compounds 6 and 7. While bivalent compound 1 also follows this trend of decreased activity, there is an even more dramatic decrease seen for 2. Overall, there is 800-fold decrease in activity for 2 compared to maraviroc. Therefore, for the bivalent compounds, para attachment is twice as favorable compared to meta attachment. Additionally, no clear synergism is seen for bivalent compounds 1 and 2 when compared to the control compounds 6 and 7. The lack of synergism may be due to the phenyl attachment of maraviroc not being well tolerated by CCR5. In all, the compounds maintain their antagonism at moderate level at either MOR or CCR5 despite the extensive modifications.

Cell Fusion Assay

While the calcium mobilization assay can assess the activity of the compounds at the receptor level it did not show the compounds' anti-HIV invasion activity. Cell fusion assays[3] provide a less dangerous alternative to working with the living virus and have been shown to mimic the HIV invasion process. FIG. 9 illustrates the general process for the cell fusion assay.

Two cell populations are used in the assay, which are called the target cells and effector cells accordingly. Fundamentally, the target cells act as the host cells that HIV infects and the effector cells act as the virus. The CCR5-MOR CHO cells were used as the basis for the target cells and were transiently transfected with CD4 and a luciferase reporter. Human embryonic kidney (HEK) cells were used as the effector cells and were transiently transfected with HIV-1 gp140 and a T7 polymerase. Once overlaid, CD4 and gp140 form a complex and interact with the CCR5-MOR heterodimer (or the CCR5 homodimer) and initiate the fusion process. Once fused, the luciferase gene reporter is transcribed and after 18 hours luminescence is measured. Adding a CCR5 antagonist, such as maraviroc, during the overlay process inhibits the fusion process and leads to a decrease in luminescence. Therefore, addition of the bivalent compounds may also inhibit the fusion process if the CCR5-MOR heterodimer plays a major role in the fusion process.

FIG. 10 is a representative cell fusion assay with and without morphine stimulation during the fusion process. Upon the addition of morphine and +CD4 effector cells there is a significant increase ($p<0.05$) in fusion compared to +CD4 effector cells alone. Addition of 1, 2, and maraviroc all significantly lowered cell fusion at concentrations of 3000 nM, 10000 nM, and 100 nM respectively. The inhibition effect of both 1 and 2 was amplified by 2-fold when morphine was present. At the concentrations shown, 1 is less effective than 2, but it has is equally effective at the higher 10000 nM that is shown for 2. Maraviroc's cell fusion inhibition was not amplified with the addition of morphine. This trend was seen in an additional three assays. The concentrations of compounds used in the assay indicate that maraviroc is more potent than either bivalent compound. However, these results do not agree with what is seen in a native system virus invasion assay consisting of astrocytes and HIV-1.

HIV-1 Invasion Assay

While the cell fusion assay mimics the native system it cannot compensate for the natural expression levels of CCR5 and MOR (and other proteins) that are seen in native systems. Primary human astrocytes were chosen because they are one of the primary sites of infection in neuroAIDS are astrocytes due to their localization on the blood brain barrier and they are the sites where opioids synergistically potentiate the pathophysiological effects of HIV-1 infection. FIG. 11 shows the effect that 1 and maraviroc have on the infection of astrocytes by HIV-1 with and without the presence of morphine stimulation.

Upon infection with R5 $HIV_{SF162}$ (with and without morphine) there was a significant increase Tat expression in astrocytes which coincides with virus invasion. When maraviroc is added, virus invasion is decreased as expected. However, when morphine is added alone with maraviroc its antiviral effects are completely abolished indicated by a significant 4-fold increase in Tat expression in the astrocytes. Treatment with naltrexone or a combination of naltrexone and maraviroc had no effect on virus invasion with and without morphine present. Addition of the bivalent compound 1 had a significant effect compared to maraviroc and maraviroc with morphine stimulation. Overall, there was a 3.3-fold decrease in virus entry compared to maraviroc alone and a 7-fold decrease when compared to maraviroc with morphine. Importantly, morphine stimulation had no effect on the bivalent compound's potency. Cytotoxicity assays (not shown) indicate neither maraviroc nor 1 had any toxicity in the astrocytes. The results show that in a native system the bivalent compound acts as a potent virus invasion inhibitor without deleterious effects caused by morphine stimulation.

Cell Fusion Assay Vs. Native System Inversion Assay

There is a disconnection between results from the cell fusion assay the astrocyte HIV-1 invasion assay. The differences between the assays can be explained through the relative expression levels seen in the cells. Using RT-PCR the mRNA expression levels of CCR5 and MOR mRNA was analyzed for both astrocytes and the CCR5-MOR CHO cells. FIG. 12 shows the results from PCR of two lots of primary human astrocytes with CCR5 being expressed 11-fold higher than MOR. The levels of MOR and CCR5 in the CCR5-MOR CHO cell line with CCR5 mRNA being expressed 24-fold higher than MOR.

There is a 2-fold difference in the ratio of MOR and CCR5 between the two cell lines with the CCR5-MOR CHO cell line having a much higher expression of CCR5 than MOR. Having a higher amount of CCR5 than MOR will lead to less heterodimers forming in the CCR5-MOR cell line than astrocytes. Since the bivalent compounds should preferentially bind to CCR5-MOR heterodimers there will be less heterodimers for it to bind to in the CCR5-MOR CHO cells than compared to astrocytes; therefore, its effects will be diminished in the CCR5-MOR CHO cells since there are less heterodimers.

Dynamic Simulation Studies

Previously a model of the chemokine receptor CCR5 (CCR5) mu opioid receptor (MOR) heterodimer was built using the recently crystallized MOR dimer as the template (FIG. 2A). In order to ascertain how the bivalent compound interacts with the heterodimer it is docked into the model using GOLD. Further modeling is needed since the docking is done with the protein movement constrained. Advanced computational methods such as molecular dynamic simulations rely on a statistical ensemble of the thermodynamics of the system and allow for motion of the system to be studied on an atomic scale. Therefore, by using molecular dynamics a more accurate picture of CCR5-MOR interaction and heterodimer-ligand interaction can be attained.

Several steps are needed in order to prepare the heterodimer-ligand complex for dynamic simulation: the complex is first added to a lipid bilayer and then solvated with a pre-defined water box with ions to more accurately simulate its native membrane environment. In all, the system built has 162385 atoms. A series of minimizations is then done in a step-wise manner to slowly equilibrate and energy minimize each component of the dimer-ligand-lipid-water-ion complex individually with the other components constrained. A second pre-equilibration is done over a short 0.5 ns time period with the entire system without any constraints. A much longer timescale production run (~100 ns) is then run to study the system. Due to the extensive nature of the computational requirement the calculation is still running and will take up to a month to finish. However, after an initial 10 ns of simulation the heterodimer-ligand complex stabilized and has several favorable interactions. FIG. 13 illustrates the overall changing in the root mean square distance (RMSD) of the dimer relative to its starting position before the start of molecular dynamics. Overall, the RMSD of the system stabilized after several nanoseconds which indicates the system is reaching equilibrium. Optimally, after an additional 90 ns of simulation those favorable interactions will stay intact and both ends of the bivalent ligand (1) will stay in the binding pocket(s) of the heterodimer.

CONCLUSION

Targeting the CCR5-MOR heterodimer is an efficacious antiviral treatment to treat neuroAIDS. Bivalent compound 1 has proven to be a potent inhibitor in both an artificial cell fusion assay mimicking HIV invasion and a native HIV invasion assay using live virus. Importantly, in the native cell HIV invasion assay maraviroc was unable to inhibit HIV infection in the presence of morphine in primary human astrocytes. However, compound was a more potent inhibitor than maraviroc in primary human astrocytes with and without morphine (3.3-fold higher virus inhibition than maraviroc without morphine, and 7-fold higher virus inhibition than maraviroc with morphine). This effect is also tissue specific: if primary human microglia are used, morphine fails to stimulate HIV-1 invasion (data not shown). Upon further analysis, it was found that the expression levels of MOR in microglia are much lower than in astrocytes. Thus, compound 1 provides a tissue-specific treatment for neuroAIDS where the known treatment, maraviroc, is less efficacious and fails to inhibit virus entry in the presence of morphine.

REFERENCES FOR EXAMPLE 3

1. Thompson, C. M.; Wojno, H.; Greiner, E.; May, E. L.; Rice, K. C.; Selley, D. E. Activation of G-proteins by morphine and codeine congeners: insights to the relevance of O- and N-demethylated metabolites at μ- and δ-opioid receptors. J. Pharmacol. Exp. Ther. 2004, 308, 547-554.
2. Conklin, B. R.; Farfel, Z.; Lustig, K. D.; Julius, D.; Bourne, H. R. Substitution of three amino acids switches receptor specificity of Gq to that of Gi alpha. Nature 1993, 363, 274-276.
3. Sakamoto, T.; Ushijima, H.; Okitsu, S.; Suzuki, E.; Sakai, K.; Morikawa, S.; Muller, W. E. Establishment of an HIV cell-cell fusion assay by using two genetically modified HeLa cell lines and a reporter gene. J. Virol. Methods 2003, 114, 159-166.

Example 4

A Bivalent Ligand Targeting the Putative Mu Opioid Receptor and Chemokine Receptor CCR5 Heterodimers: Binding Affinity Versus Functional Activities A bivalent ligand 1 (FIG. 14) that combines the pharmacophores of naltrexone (a MOR antagonist) and maraviroc (a CCR5 antagonist) into one molecule was designed and synthesized. Herein is reported the characterization of this novel molecular probe in for its binding affinity, $Ca^{2-}$ flux functional activity, and HIV-1 inhibition potency. Bivalent ligand 1 was first characterized in hMOR-expressed CHO cells in the competitive radioligand binding assay as described previously.[1,2] As shown in Table 1, bivalent ligand 1 retained moderate binding affinity to the MOR, as indicated by the two-digit nanomolar $K_i$ value. Monovalent ligand 2 displayed relatively high MOR affinity compared to the parent compound, naltrexone.

As $Ca^{2+}$ flux is associated with the activation of the MOR, the functional activity of bivalent ligand 1, monovalent ligand 2, and naltrexone was then evaluated in a $Ca^{2+}$ mobilization assay in hMOR—CHO cells transfected with chimeric $Ca^{2+}$ following a published protocol.[23] No agonism was observed for any of the tested compounds (data not shown). Thus, they were further assessed for their antagonist properties as the ability to inhibit DAMGO (a MOR agonist) induced $Ca^{2+}$ flux. As shown in Table 2, the potency of bivalent ligand 1 to antagonize DAMGO-induced $Ca^{2+}$ flux was modestly reduced (less than 5-fold) compared to that of naltrexone. Nevertheless, bivalent ligand 1 did fulfill the original design as a potent MOR antagonist with moderate binding affinity.

TABLE 2

MOR Radioligand binding assay and DAMGO stimulated $Ca^{2+}$ flux assay[a]

| Compound | Radioligand binding $K_i$ ± SEM (nM) | $Ca^{2+}$ inhibition $IC_{50}$ ± SEM (nM) |
|---|---|---|
| naltrexone | 0.7 ± 0.1 | 8.9 ± 0.9 |
| 1 | 51.8 ± 7.9 | 40.0 ± 4.8 |
| 2 | 9.2 ± 3.4 | 37.8 ± 4.4 |

[a][3H]naloxone was used as the radioligand in the binding assay. The values are the means ± S.E.M. of three independent experiments.

Afterwards, the pharmacological profile of bivalent ligand 1 at the chemokine receptor CCR5 was characterized similarly. The competitive radioligand binding assay was conducted in CCR5 rhesus macaque membrane preparations from Chem-1 cells. Monovalent ligand 3 and compound 4, an analogue of maraviroc, were tested along under the same condition. Introduction of the 4-NH2 group onto the phenyl ring of maraviroc, as seen in compound 4, caused approximately 65-fold decrease in the binding affinity, compared to maraviroc. The decrease of the binding affinity was even more profound for bivalent ligand 1 and monovalent ligand 3, as their $K_i$ values dropped to submicromolar range, respectively. Apparently a para-substitution on the phenyl ring of maraviroc, no matter its size, is detrimental for the CCR5 binding (Table 3).

Then the $Ca^{2+}$ functional activity of bivalent ligand 1 was evaluated in the $G_{qi5}$ transfected CCR5-MOLT-4 cells as described in the literature.[3] As expected, no CCR5 agonism was detected for the bivalent ligand 1 (data not shown). In the RANTES induced $Ca^{2+}$ flux inhibition assay (Table 3), the bivalent ligand 1 was approximately 60-fold less potent than maraviroc. A more significant potency decrease (nearly 300 times) was observed for the monovalent ligand 3, compared to maraviroc. In order to figure out the possible reasons for such a dramatic drop of their potency, two analogues (4 and 5, FIG. 14) of mavaviroc carrying gradient steric hindrance characters at the same substitution position were evaluated under the same condition. Compound 4 showed a modest reduction of the potency (Table 2). However, the inhibition potency of the N-t-Boc protected analogue 5 dropped to micromolar ($IC_{50}=1.57\pm0.18$ μM). It thus appeared that steric hindrance may play an essential role for the reduced potency, as seen in both the bivalent ligand 1 and the monovalent ligand 3. To further test this hypothesis, a monovalent ligand 6 (FIG. 14) with a 7-atom spacer was synthesized and assessed under the same conditions. The inhibition potency of the monovalent ligand 6 ($IC_{50}=7.91\pm0.76$ μM) was further reduced compared to analogue 5. This again suggested that steric hindrance generated through introducing substitutions onto the para-position of phenyl ring system in maraviroc is disadvantageous for its antagonism in $Ca^{2+}$ mobilization. Nonetheless, being a CCR5 antagonist, bivalent ligand 1 still met the basic requirements of the original design though its relatively lower binding affinity to the CCR5 was somehow less promising.

TABLE 3

CCR5 Radioligand binding assay and RANTES stimulated $Ca^{2+}$ flux assay[a]

| Compound | Radioligand binding $K_i \pm$ SEM (nM) | $Ca^{2+}$ inhibition $IC_{50} \pm$ SEM (nM) |
| --- | --- | --- |
| maraviroc | 0.24 ± 0.06 | 2.2 ± 0.3 |
| 1 | 239 ± 56 | 126 ± 28 |
| 3 | 151 ± 44 | 622 ± 36 |
| 4 | 15.3 ± 4.8 | 14.2 ± 1.9 |

[a] [$^{125}$I]MIP-1α was used as the radioligand in the binding assay. The values are the means ± S.E.M. of three independent experiments.

As the bivalent ligand 1 has been designed as a molecular probe to study the underlying mechanisms of opioid-enhanced NeuroAIDS by targeting the MOR—CCR5 heterodimerization, a luciferase-based HIV-1$_{SF162}$ infection assay measuring the relative transactivator of transcription (Tat) protein expression in human astrocytes was performed (FIG. 15). Tat is encoded by HIV-1 and is the first protein to be produced after HIV-1 infection. Thus, Tat expression level is directly proportioned to the extent of HIV-1 invasion. Astrocytes were chosen based on the following facts: first, astrocytes express both the MOR and the CCR5. Second, the human blood-brain barrier (BBB) is composed of interacting adjacent cerebral endothelial cells (CECs) and astrocytes, which makes astrocytes a readily accessible target during the course of HIV infection. Thirdly, during NeuroAIDS development astroglia are important cellular sites within the CNS where opioids synergistically potentiate the pathophysiological effects of HIV-1 infection.

FIG. 15 shows that the relative Tat expression was significantly increased in astrocytes after infection with R5 HIV-1$_{SF162}$ isolated from the CNS of AIDS patients. As expected, exposure to maraviroc (MVC, 100 nM) considerably inhibited viral entry by interrupting the role of CCR5 as a co-receptor of HIV-1. In contrast, naltrexone (NTX, 1.5 μM) did not show significant effect on Tat production. Not surprisingly, the blockage of virus infection by a simple mixture of maraviroc (100 nM) and naltrexone (1.5 μM) was similar to the effect from maraviroc alone. However, bivalent ligand 1 (100 nM) was significantly effective in inhibiting viral entry into human astrocytes, causing at least a two-fold decrease in Tat expression when compared to maraviroc alone, or the combination of maraviroc and naltrexone, respectively. The results thus indicated that the bivalent ligand 1 functions as a potent HIV-1 inhibitory agent in human astrocytes through interacting specifically with the putative MOR—CCR5 heterodimer.

During the development of CCR5 antagonists as anti-HIV agents, Lemoine et al. found that there was no definite correlation between the radioligand binding affinity and the antiviral activity. Meanwhile, a number of GPCR ligands have been proposed to show "functional selectivity: differences in ligand-induced intermediate conformational states, diversity of G proteins, scaffolding and signaling partners, and receptor oligomers may lead to different functions". Based on the results obtained from the current study for bivalent ligand 1 and maraviroc, a possible mechanism of their "functional selectivity" from the receptor dimerization prospective was proposed (FIG. 16). In the radioligand binding assay in the Chem-1 cells and Cat functional assay in MOLT-4 cells, the CCR5 receptor may exist as monomer or homodimers. The conformation of maraviroc may fit the binding pocket of the CCR5 monomer and/or the homodimer nicely to induce its function. Whereas in the HIV-1 invasion assay, CCR5 and MOR may form heterodimers in the human astrocytes, and the subsequent conformation change might enable the binding pocket of CCR5 to accommodate the bivalent ligand (the conformation of the CCR5 antagonist pharmacophore portion might also be changed due to the introduction of the spacer and the MOR antagonist portion) to induce the inhibition of viral entry. On the contrary, the bivalent molecule may not fit as well as maraviroc could into the binding pocket of the CCR5 monomer and/or homodimer. Similarly maraviroc may not recognize the CCR5 heterodimer binding pocket as well as the bivalent ligand could. As a result, maraviroc was observed to be much more potent than bivalent ligand 1 in the monocloned receptor competition binding assay and the $Ca^{2+}$ flux inhibition assay while bivalent ligand 1 apparently was more potent than maraviroc to inhibit HIV-1 infection in the invasion assay.

In conclusion, the bivalent ligand 1 acted as a CCR5 and a MOR dual antagonist with moderate binding affinity to both receptors compared to the parent pharmacophores. The steric hindrance generated from the introduction of the spacer to the molecule affected its binding and $Ca^{2+}$ function activity at the CCR5 more profoundly than it did at the MOR, whereas it was more potent than maraviroc in reducing Tat expression upon HIV-1 infection in human astrocytes. Thus, small molecule maraviroc and bivalent ligand 1 displayed a "functional selectivity" profile upon binding to the CCR5 under different circumstances. More importantly, bivalent ligand 1 was two times more potent than the mixture of maraviroc and naltrexone in HIV-1 entry inhibition. The results reported here indicate that the bivalent ligand blocks HIV-1 invasion into host cells by targeting specifically the putative MOR—CCR5 heterodimer.

ABBREVIATIONS USED IN EXAMPLE 4

AIDS, acquired immunodeficiency syndrome; BBB, blood-brain barrier; N-tert-Boc, N-tert-butoxycarbonyl; CECs, cerebral endothelial cells; CNS, central nervous system; CHO, Chinese hamster ovary; DAMGO, [D-Ala2-MePhe-4-Gly(ol)5]enkephalin; GPCRs, G-protein coupled receptors; HAART, highly active antiretroviral therapy; HAND, HIV-associated neurocognitive disorders; HIV, human immunodeficiency virus; MVC, maraviroc; MIP-1α, macrophage inflammatory protein-1α; MOR, mu opioid receptor; NTX, naltrexone; OST, opioid substitution therapy; RANTES, regulated on activation, normal T-cell expressed and secreted; Tat, transactivator of transcription.

REFERENCES FOR EXAMPLE 4

1. Li, G.; Aschenbach, L. C.; Chen, J.; Cassidy, M. P.; Stevens, D. L.; Gabra, B. H.; Selley, D. E.; Dewey, W. L.; Westkaemper, R. B.; Zhang, Y. Design, synthesis, and biological evaluation of 6α- and 6β-N-heterocyclic substituted naltrexamine derivatives as μ opioid receptor selective antagonists. *J. Med. Chem.* 2009, 52, 1416-1427.
2. Yuan, Y.; Li, G; He, H.; Stevens, D. L.; Kozak, P.; Scoggins, K. L.; Mitra, P.; Gerk, P. M.; Selley, D. E.; Dewey, W. L.; Zhang, Y. Characterization of 6α- and 6β-N-heterocyclic substituted naltrexamine derivatives as novel leads to development of mu opioid receptor selective antagonists. ACS Chem. Neurosci. 2011, 2, 346-351.
3. Conklin, B. R.; Farfel, Z.; Lustig, K. D.; Julius, D.; Bourne, H. R. Substitution of three amino acids switches receptor specificity of $G_q\alpha$ to that of $G_i\alpha$. *Nature* 1993, 363, 274-276.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

All references cited herein are hereby incorporated by reference in entirety.

We claim:

1. A bivalent ligand of Formula I,

Formula I

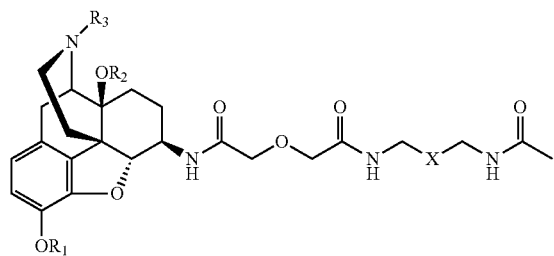

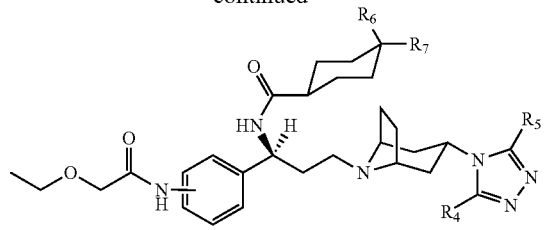

wherein $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;

$R_3$ may be present or absent and may be H; $H_2$; O; $C_{1-12}$alkyl; —$COOR_9$ where $R_9$ is $C_{1-12}$alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;

R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group; and X=a branched or unbranched, saturated or unsaturated carbon chain comprising from 1-20 carbon atoms, and may include a heteroatomic group;

as well as salts, protonated and unprotonated and stereoisomeric forms thereof.

2. The bivalent ligand of claim 1, wherein said bivalent ligand is

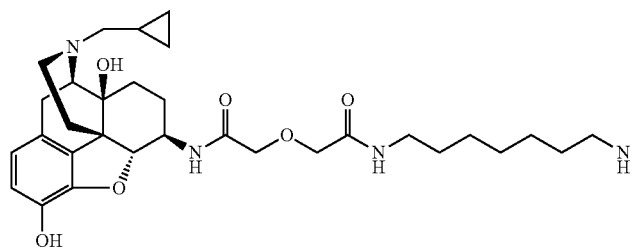

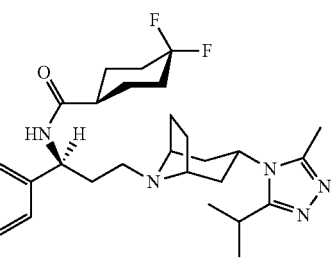

3. A pharmaceutical composition comprising at least one bivalent ligand of Formula I,

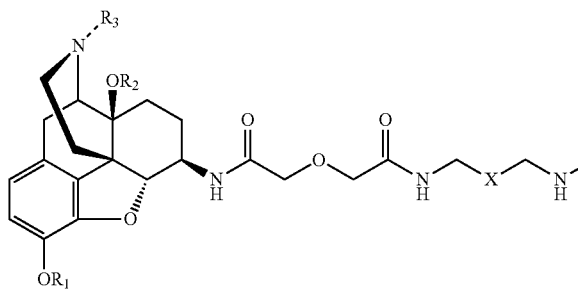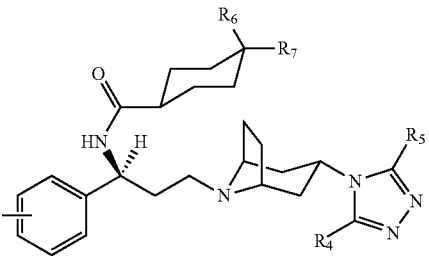

Formula I wherein
- $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;
- $R_3$ may be present or absent and may be H; $H_2$; O; alkyl; —$COOR_9$ where $R_9$ is $C_{1-12}$alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;
- $R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;
- R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group;
- X=a branched or unbranched, saturated or unsaturated carbon chain comprising from 1-20 carbon atoms, and may include a heteroatomic group;
- as well as salts, protonated and unprotonated and stereoisomeric forms thereof; and
- a physiologically compatible carrier.

4. The pharmaceutical composition of claim 3, wherein said at least one bivalent ligand is

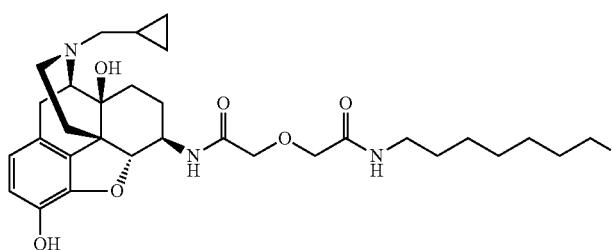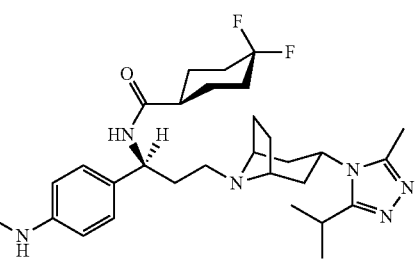

1

5. A method of treating neuroAIDS in a subject in need thereof, comprising
administering to said subject a therapeutically effective amount of at least one bivalent ligand of Formula I,

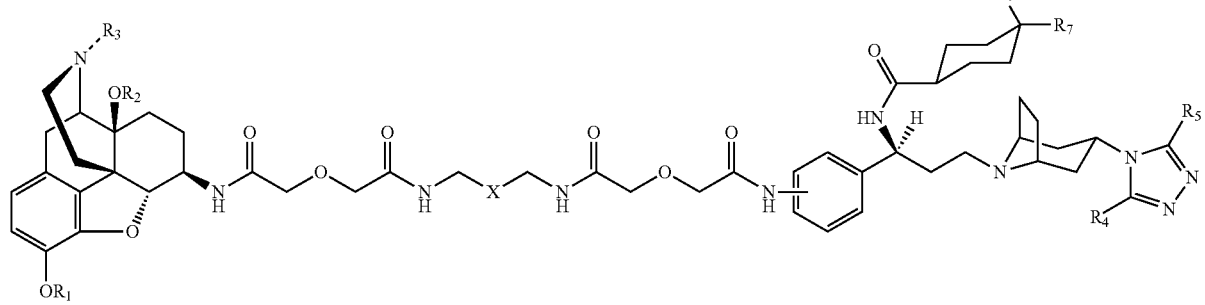

Formula I wherein
- $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;
- $R_3$ may be present or absent and may be H; $H_2$; O; $C_{1-12}$alkyl; —$COOR_9$ where $R_9$ is $C_{1-12}$alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;
- $R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;
- R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group; and
- X a branched or unbranched, saturated or unsaturated carbon chain comprising from 1-20 carbon atoms, and may include a heteroatomic group;

as well as salts, protonated and unprotonated and stereoisomeric forms thereof.

6. The method of claim 5, wherein said at least one bivalent ligand is

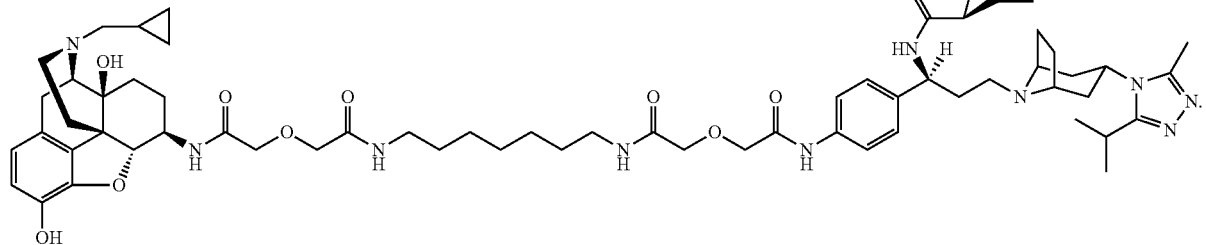

7. The method of claim 5, wherein said subject abuses or is addicted to opiates.

8. A method of blocking entry of a human immunodeficiency virus (HIV) into an astrocyte, comprising
exposing said astrocyte to at least one bivalent ligand of Formula I, Formula I

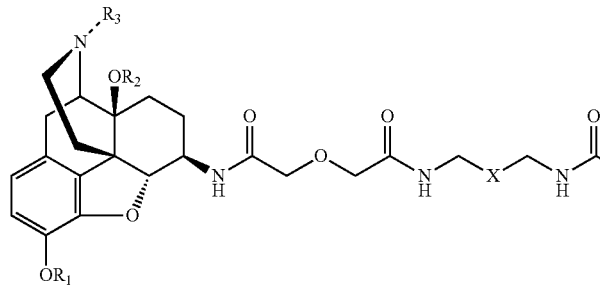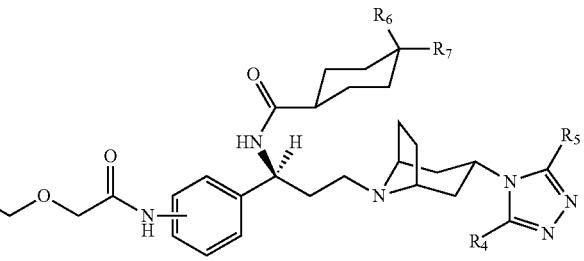

wherein $R_1$ and $R_2$ may be the same or different, and are independently selected from: H; a saturated or unsaturated, branched or unbranched, substituted or unsubstituted carbon group or chain comprising from 1-20 carbon atoms; $NO^-$; $NO^{-2}$; CO; $COR_8$ wherein $R_8$ is H or a saturated or unsaturated, branched or unbranched, substituted or unsubstituted carbon group or chain comprising from 1-20 carbon atoms; $SO_3^{-2}$; and $SO_4^{-2}$;

$R_3$ may be present or absent and may be H; $H_2$; O; $C_{1-12}$alkyl; —$COR_9$ where $R_9$ is $C_{1-12}$alkyl; $CR_{10}$ where $R_{10}$ is a cyclic or polycyclic saturated or unsaturated homo- or heterocyclic ring system comprising 1, 2, 3, 4, or more rings with from 3 to 7 atoms per ring in the system;

$R_4$ and $R_5$ may be present or absent; may be the same or different, and are independently selected from H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the triazole ring; and a heteroatomic group;

R6 and R7 may be the same or different, and are independently selected from: H; halogen; a saturated or unsaturated, branched or unbranched, substituted or unsubstituted carbon group or chain comprising from 1-20 carbon atoms; a cyclic or polycyclic saturated or unsaturated homo- or heterocyclic ring system comprising 1, 2, 3, 4, or more rings with from 3 to 7 atoms per ring in the system, which may be fused to one or more atoms of the hexane ring; and a heteroatomic group; and X=a branched or unbranched, saturated or unsaturated carbon chain comprising from 1-20 carbon atoms, and may include a heteroatomic group;

as well as salts, protonated and unprotonated and stereoisomeric forms thereof.

9. The method of claim 8, wherein said step of exposing is carried out in the presence of an opiate.

10. The method of claim 9, wherein said opiate is morphine.

* * * * *